(12) United States Patent
Geddes et al.

(10) Patent No.: US 8,569,502 B2
(45) Date of Patent: Oct. 29, 2013

(54) QUATERNARY NITROGEN HETEROCYCLIC COMPOUNDS FOR DETECTING AQUEOUS MONOSACCHARIDES IN PHYSIOLOGICAL FLUIDS

(71) Applicants: Chris D. Geddes, Bel-Air, MD (US); Ramachandram Badugu, Baltimore, MD (US); Joseph R. Lakowicz, Ellicott City, MD (US)

(72) Inventors: Chris D. Geddes, Bel-Air, MD (US); Ramachandram Badugu, Baltimore, MD (US); Joseph R. Lakowicz, Ellicott City, MD (US)

(73) Assignee: Chris Geddes, Bel-Air, MD (US)

(*) Notice: Subject to any disclaimer, the term of this patent is extended or adjusted under 35 U.S.C. 154(b) by 0 days.

(21) Appl. No.: 13/726,445

(22) Filed: Dec. 24, 2012

(65) Prior Publication Data
US 2013/0210158 A1    Aug. 15, 2013

Related U.S. Application Data

(60) Division of application No. 12/781,899, filed on May 18, 2010, now Pat. No. 8,338,602, which is a division of application No. 11/318,663, filed on Dec. 27, 2005, now Pat. No. 7,718,804, which is a continuation-in-part of application No. PCT/US2004/022717, filed on Jun. 28, 2004.

(60) Provisional application No. 60/483,202, filed on Jun. 27, 2003, provisional application No. 60/483,124, filed on Jun. 27, 2003.

(51) Int. Cl.
C07D 215/38    (2006.01)

(52) U.S. Cl.
USPC .......................................... 546/102; 546/104

(58) Field of Classification Search
USPC .................................................. 546/102, 104
See application file for complete search history.

(56) References Cited

U.S. PATENT DOCUMENTS

| | | | |
|---|---|---|---|
| 3,731,681 A | 5/1973 | Blackshear et al. | |
| 4,573,994 A | 3/1986 | Fischell et al. | |
| 4,923,375 A | 5/1990 | Ejlersen | |
| 5,075,556 A * | 12/1991 | Fan et al. | 250/459.1 |
| 5,583,163 A | 12/1996 | Muller | |
| 5,665,840 A | 9/1997 | Pohlmann et al. | |
| 5,712,356 A | 1/1998 | Bothe et al. | |
| 5,849,841 A | 12/1998 | Muhlebach et al. | |
| 5,957,890 A | 9/1999 | Mann et al. | |
| 6,165,408 A | 12/2000 | Steinmann | |
| 6,221,303 B1 | 4/2001 | Steinmann | |
| 6,303,687 B1 | 10/2001 | Muller | |
| 6,479,587 B1 | 11/2002 | Stockinger et al. | |
| 6,681,127 B2 | 1/2004 | March | |
| 6,850,786 B2 | 2/2005 | March | |
| 6,980,842 B2 | 12/2005 | March et al. | |
| 7,906,293 B2 * | 3/2011 | Mattingly et al. | 435/7.1 |
| 2004/0087842 A1 | 5/2004 | Lakowicz et al. | |
| 2005/0015237 A1 | 1/2005 | Debili | |
| 2008/0096281 A1 | 4/2008 | Geddes et al. | |

FOREIGN PATENT DOCUMENTS

| | | |
|---|---|---|
| EP | 0 655 470 B1 | 5/1999 |
| EP | 0 712 867 B1 | 7/1999 |
| EP | 0 958 315 B1 | 6/2001 |
| EP | 0 932 635 B1 | 7/2001 |
| EP | 0 961 941 B1 | 4/2002 |
| WO | WO 00/31550 | 6/2000 |
| WO | WO01/74968 | 10/2001 |
| WO | WO02/46752 | 6/2002 |

OTHER PUBLICATIONS

Chris D. Geddes; Optical halide sensing using fluorescence quenching: theory, simulations and applications—a review; Measurement Science and Technology; 2001; vol. 12, pp. R53-R88; 10P Publishing Ltd., UK.

N Gupta et al.; Tear glucose estimation-an alternative to blood glucose est.; Journal of the Indian Medical Association; 1996; vol. 94, No. 10; p. 391.

Mia Bielecki et al.; A fluorescent glucose sensor binding covalently to all five hydroxy groups of a-D-glucofuranose. A reinvestigation.; J. Chem. Soc., Perkin Trans. 2; 1999; pp. 449-455.

Nicolas DiCesare et al.; Evaluation of Two Synthetic Glucose Probes for Fluorescence-Lifetime-Based Sensing; Analytical Biochemistry; 2001; vol. 21; pp. 154-160; Academic Press.

Nicolas DiCesare et al.; Charge transfer fluorescent probes using boronic acids for monosaccharide signaling; Journal of Biomedical Optics; Oct. 2002; vol. 7, No. 4; pp. 538-545.

Rong Chen et al.; Analysis of tear fluid by CE/LIF: A noninvasive approach for glucose monitoring; Journal of Capillary Electrophoresis.; 1993; vol. 3, Issue 5; pp. 243-248.

N.J. Van Haeringen; Clinical Biochemistry of Tears; Survey of Opthamology; Sep.-Oct. 1981; vol. 26, No. 2, pp. 84-96.

(Continued)

*Primary Examiner* — D M Seaman
(74) *Attorney, Agent, or Firm* — Marianne Fuierer; Moore & Van Allen, PLLC

(57) ABSTRACT

Quaternary nitrogen heterocyclic boronic acid-containing compounds are described, which are sensitive to glucose and fructose, as well as a variety of other physiologically important analytes, such as aqueous chloride and iodide, and a method of using the compounds. Also disclosed is a contact lens doped with the quaternary nitrogen heterocyclic boronic acid-containing compound, and a method of using the doped contact lens to measure the concentration of analyte in tears under physiological conditions.

13 Claims, 41 Drawing Sheets

(56) References Cited

OTHER PUBLICATIONS

Leah Tolosa et al.; Optical assay for glucose based on the luminescnence decay time of the long wavelength dye Cy5TM; Sensors and Actuators; 1997; B, 45; pp. 93-99; Elsevier Science S.A.

Wayne F. March et al.; Intraocluar Lens Glucose Sensor; Diabetes Technology & Therapeutics; 2000; vol. 2, No. 1; pp. 27-30.

Sujatha Jayaraman et al,. Quenching mechanism of quinolinium-type chloride-sensitive fluorescent indicators; Biophysical Chemistry; 2000; vol. 85; pp. 49-57; Elsevier Science B.V.

Tony D. James et al.; Novel Saccharide-Photoinduced Electron Transfer Sensors Based on the Interaction of Boronic Acid and Amine; Journal of American Chemical Society; 1995; vol. 117, No. 35; pp. 8982-8987; American Chemical Society.

Nicolas DiCesare et al.; Chalcone-anaolgue fluorescent prfobes for sacchardies signaling using the boronic acid group; Tetrahedron Letters; 2002; vol. 43; pp. 2615-2618; Elsevier Science Ltd.

Nicolas DiCesare et al.; New Color Chemosensors for monosaccharides Based on Azo Dyes; Organic Letters; 2001; vol. 3, No. 24; pp. 3891-3893; American Chemical Society.

Nicolas DiCesare et al.; Spectral Properties of Fluorophores Combining the Boronic Acid Group with Electron Donor or Withdrawing Groups. Implication in the Development of Fluorescence Probes for Saccharides; J. Phys. Chem. A; 2001; vol. 105, No. 28; pp. 6834-6840; American Chemical Society.

B.N Das et al.; Tear Glucose Estimation—An Alternative to Blood Glucose Estimation; Journal of the Indian Medical Association; Apr. 1995; vol. 93, No. 4; pp. 127-128.

Leah Tolosa et al.; Lifetime-Based Sensing of Glucose Using Energy Transfer with a Long Lifetime Donor; Analytical Biochemistry; 1997; vol. 250; pp. 102-108; Academic Press.

Sherryl A. Perez et al.; Determination of carbohydrates as their dansylhydrazine derivatives by capillary electrophoresis with laser-induced fluorescence detection; Electrophoresis; Feb. 1996; vol. 7, Issue 2; pp. 352-358.

Zhe Jin et al.; Determination of Glucose in Submicroliter Samples by CE-LIF Using Precolumn or On-Column Enzymatic Reactions; Analytical Chemistry; Apr. 1997; vol. 69, No. 7; pp. 1326-1331; American Chemical Society.

Tony D. James et al.; A Glucose-Selective Molecular Fluorescence Sensor; Angewandte Chemie International Edition in English; Nov. 1994; vol. 33, Issue 21; pp. 2207-2209.

Chris D. Geddes et al.; New Indolium and Quinolinium Dyes Sensitive to Aqueous Halide Ions at Physiological Concentrations; Journal of Heterocyclic Chemistry; Jul.-Aug. 1999; vol. 36, No. 4; pp. 949-951; HeteroCorporation.

Chris D. Geddes et al.; Chloride-Sensitive Fluorescent Indicators; Analytical Biochemistry; 2001; vol. 293; pp. 60-66; Academic Press.

* cited by examiner

F = Fluorophore

A

B

US 8,569,502 B2

QUATERNARY NITROGEN HETEROCYCLIC COMPOUNDS FOR DETECTING AQUEOUS MONOSACCHARIDES IN PHYSIOLOGICAL FLUIDS

CROSS-REFERENCE TO RELATED APPLICATIONS

This application is a divisional application of U.S. patent application Ser. No. 12/781,899, filed on May 18, 2010, now U.S. Pat. No. 8,338,602, which was a divisional application of U.S. patent application Ser. No. 11/318,663 filed on Dec. 27, 2005, now U.S. Pat. No. 7,718,804, which was a Continuation-in-Part application of PCT Application No. PCT/US04/22717, filed on Jun. 28, 2004, which in turn claims priority to U.S. Provisional Application Nos. 60/483,124 and 60/483,202 filed on Jun. 27, 2003, respectively, the contents of which are incorporated by reference herein for all purposes.

BACKGROUND OF THE INVENTION

1. Field of the Invention

The invention relates to fluorophores and more particularly to highly fluorescent and analyte sensitive boronic acid containing fluorophores and for methods of using same for measuring analyte concentrations, such as glucose in physiological fluids, such as the blood and tears, in a continuous and non-invasive manner. The invention further relates to ophthalmic devices comprising the fluorophores, which interact with the analyte to be measured providing an optical signal being indicative of the analyte level in an ocular fluid.

2. Background of the Related Art

Individuals suffering from diabetes mellitus have an abnormally high blood sugar level, generally because the pancreas does not secrete sufficient amounts of the active hormone insulin into the bloodstream to regulate carbohydrate metabolism. If an abnormally high blood sugar level, known as a hyperglycemic condition, is allowed to continue for prolonged periods, the individual will suffer from the chronic complications of diabetes, including retinopathy, nephropathy, neuropathy and cardiovascular disease. Presently, approximately 150 million people worldwide are affected by diabetes. Studies indicate that diabetic patients who are able to maintain near normal glycemic control greatly reduce the likelihood of these direct complications. Therefore, several tests have been developed to measure and control the glycemic condition.

One common medical test to control glycemic condition is the direct measurement of blood glucose levels. Blood glucose levels fluctuate significantly throughout a given day, being influenced by diet, activity, and treatment. Depending on the nature and severity of the individual case, some patients must measure their blood glucose levels up to seven times a day. Methods of glucose analysis include electrochemistry, near infrared spectroscopy, optical rotation, colorimetry, fluorimetry, and the enzyme-based method, the latter being the most commonly used. Unfortunately, the enzyme-based method has several disadvantages, including the requirement of "finger pricking," which is highly invasive and often inconvenient. It is known that many diabetic patients often skip the analysis step, i.e., drawing blood, and administer an estimated dose of insulin, which can lead to substantial fluctuations in insulin levels over time. Further, the enzyme-based method is not continuous, thus putting the patient at risk of unacceptably high or low glucose levels.

In recent years, various non-invasive and minimally-invasive technologies have been proposed in the academic and patent literature to monitor glucose levels in the blood, ocular fluid, e.g., tears, aqueous humor or interstitial fluid. For example, the GlucoWatch® non-invasively monitors glucose levels in the interstitial fluid every ten minutes for up to thirteen hours. However, the GlucoWatch® manufacturers expressly state that the GlucoWatch® is designed to merely supplement conventional blood glucose monitoring.

U.S. Pat. No. 6,681,127 discloses an ophthalmic lens, including a chemical sensor, to determine the amount of an analyte, e.g., glucose, in an ocular fluid. Such ophthalmic lens includes a receptor moiety, which can bind either a specific analyte, e.g., glucose, or a detectably labeled competitor moiety. The amount of detectably labeled competitor moiety which is displaced from the receptor moiety by the analyte is measured and provides a means of determining analyte concentration in the ocular fluid. A disadvantage of this method includes the potential that other compounds are present in the fluid that are capable of displacing the competitor moiety, thereby giving a false analyte concentration.

It is well known in the glucose monitoring arts that tear glucose levels directly track blood glucose levels, however, the concentration of glucose in tears, e.g., 50-500 µM, is about ten times lower than the corresponding blood glucose level (Van Haeringen, N. J., *Surv. Ophthalmol.*, 29(2), 84-96 (1981); Gasser, A. R., et al., *Am. J. Ophthalmol.*, 65(3), 414-420 (1968); Das, B. N., et al., *J. Indian Med. Assoc.*, 93(4), 127-128 (1995); Chen, R., et al., *J. Capillary Electrophor.*, 3(5), 243-248 (1996); Perez, S. A., *Electrophoresis*, 17(2), 352-358 (1996); Jin, Z., *Anal. Chem.*, 69(7), 1326-1331 (1997)). Accordingly, to determine the concentration of glucose in tears requires a methodology that is highly sensitive relative to standard blood glucose methods. To date, attempts to monitor tear glucose concentrations have been invasive and applied non-continuous methodologies.

Therefore, there is a continuing need for new methods of determination of monosaccharide, e.g., glucose and fructose that are sensitive enough to quantitatively determine monosaccharide levels in tears and other bodily fluids under physiological conditions. These methods should be continuous, non-invasive and uncomplicated, thereby ensuring the diabetic actively monitors their blood glucose levels.

Correspondingly, there is a need for methods of determination of levels of a variety of other analytes in tears and other bodily fluids under physiological conditions, for applications including monitoring of patient stability, medication compliance, exposure of individuals to environmental contaminants and toxins, etc.

SUMMARY OF THE INVENTION

The present invention generally relates to highly fluorescent and glucose sensitive boronic acid containing fluorophores which are sensitive to glucose and fructose, as well as a variety of other physiologically important analytes, such as aqueous chloride, iodide, fluoride and cynanide; methods of using such fluorophores compounds. Preferably, the highly fluorescent and glucose sensitive boronic acid containing fluorophores comprise quaternary nitrogen heterocyclic boronic acid-containing compounds. Further, the present invention relates to using these sensitive fluorophores in glucose sensing ophthalmic devices, e.g., off-the-shelf disposable plastic contact lenses that are coated or impregnated with novel glucose sensitive fluorophores.

In one aspect the present invention relates to novel quaternary nitrogen heterocyclic boronic acid-containing compounds including:

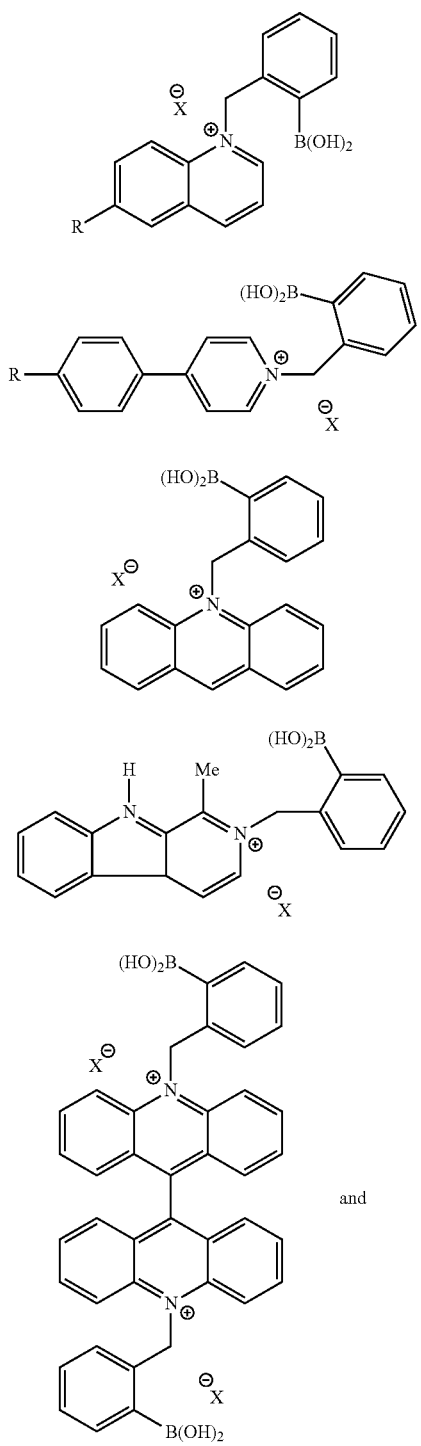

(A)

(B)

(C)

(D)

(E)

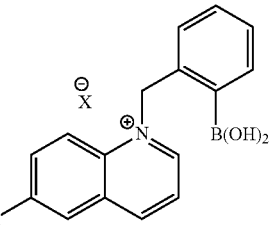

(F)

wherein X is chloride, bromide or iodide and R is selected from the group consisting of H, straight chain or branched $C_1$-$C_4$ alkyl group, $C_1$-$C_4$ alkoxy group, aryl group, hydroxyl, cyano, sulfonyl, and $NR^1R^2$, wherein $R^1$ and $R^2$ may be the same as or different from one another and is independently selected from the group consisting of H and $C_1$-$C_4$ alkyl groups.

In yet another aspect, the present invention relates to an optical device, wherein the optical device comprises at least one fluorophore, wherein the fluorophore comprises a boronic acid group and an electron-donor group and wherein the boronic acid group acts as an electron-withdrawing group until interaction with a sugar thereby causing a decrease in the $pK_a$ of the boronic acid and spectral changes due to reduced charge-transfer. Preferably, the fluorophore is a quaternary nitrogen heterocyclic boronic acid-containing compound including:

(A)

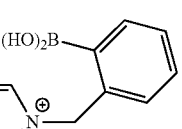

(B)

(C)

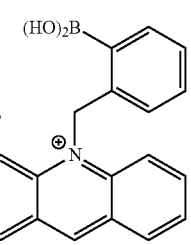

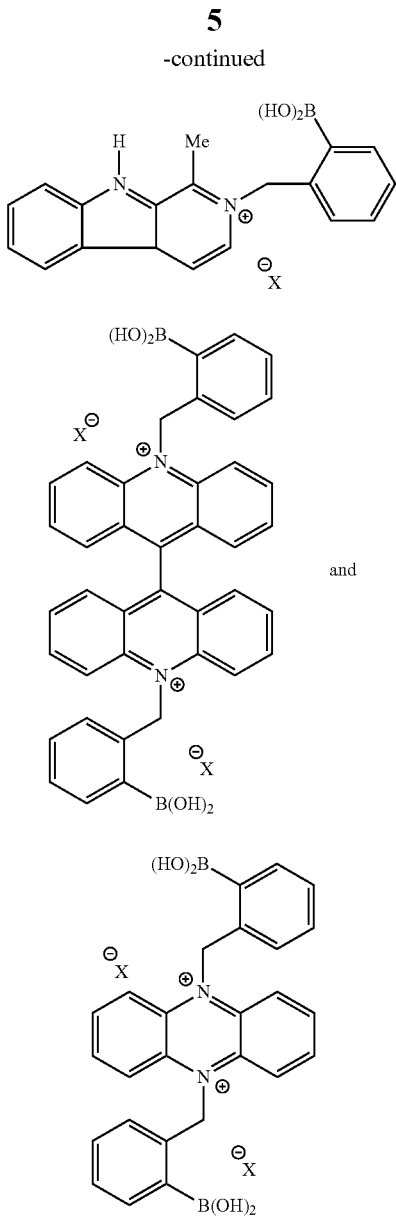

wherein X is chloride, bromide or iodide and R is selected from the group consisting of H, straight chain or branched $C_1$-$C_4$ alkyl group, $C_1$-$C_4$ alkoxy group, aryl group, hydroxyl, cyano, sulfonyl, and $NR^1R^2$, wherein $R^1$ and $R^2$ may be the same as or different from one another and is independently selected from the group consisting of H and $C_1$-$C_4$ alkyl groups.

Additional fluorophores that exhibits the necessary reduced charge transfer spectral change include:

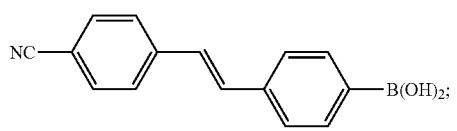

Preferably, the optical device is a contact lens that is used to measure the concentration of glucose in tears under physiological conditions, wherein the contact lens includes at least one of the following compounds:

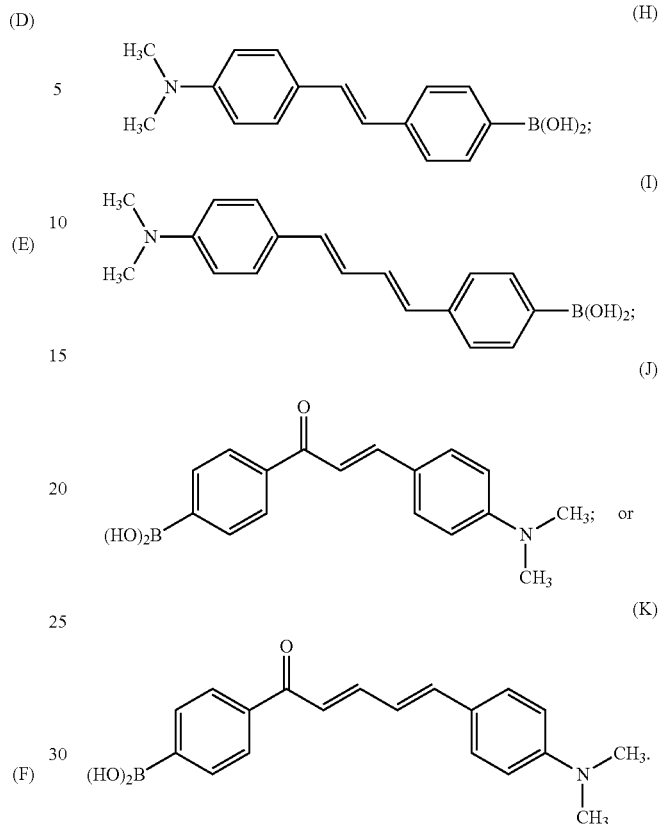

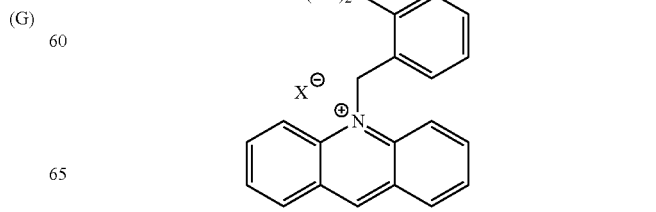

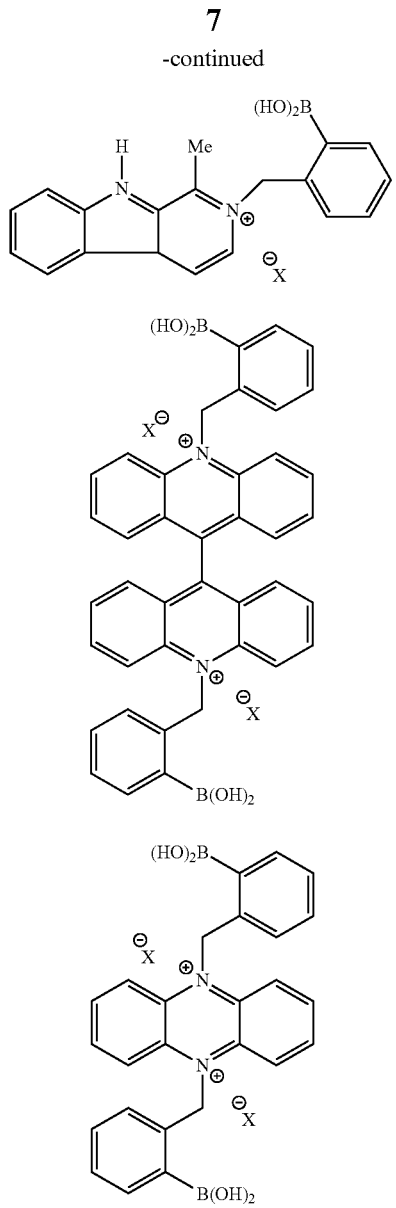

wherein X is chloride, bromide or iodide and R is selected from the group consisting of H, straight chain or branched $C_1$-$C_4$ alkyl group, $C_1$-$C_4$ alkoxy group, aryl group, hydroxyl, cyano, sulfonyl, and $NR^1R^2$, wherein $R^1$ and $R^2$ may be the same as or different from one another and is independently selected from the group consisting of H and $C_1$-$C_4$ alkyl groups;

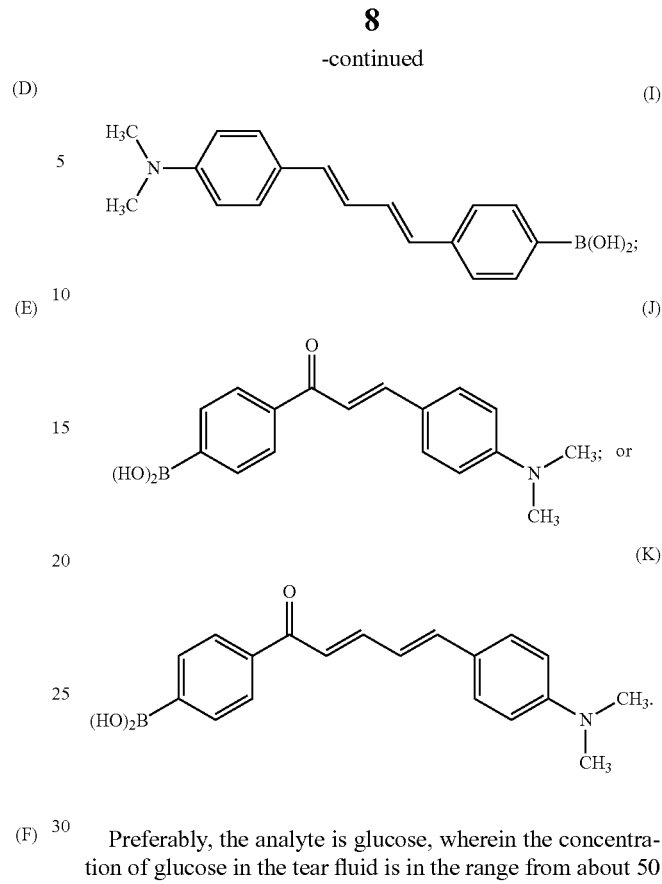

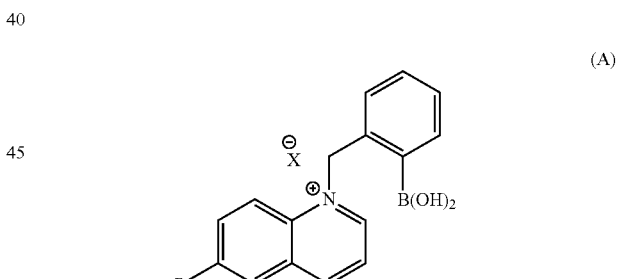

Preferably, the analyte is glucose, wherein the concentration of glucose in the tear fluid is in the range from about 50 um to about 500 um.

In still another aspect, the present invention relates to a method of measuring the concentration of an analyte in a physiological fluid, said method comprising:

(a) contacting a fluorescence compound selected from the group consisting of:

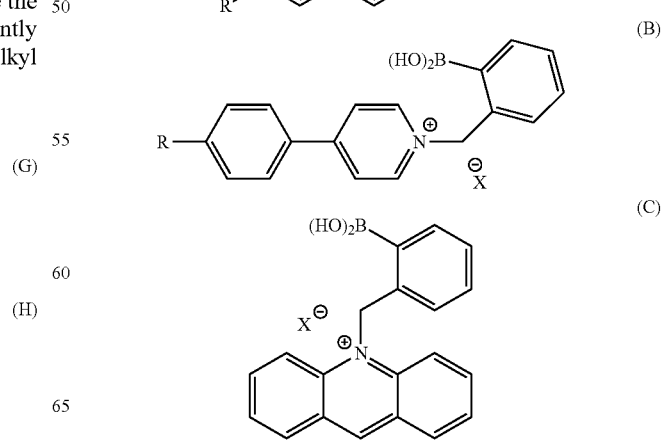

-continued

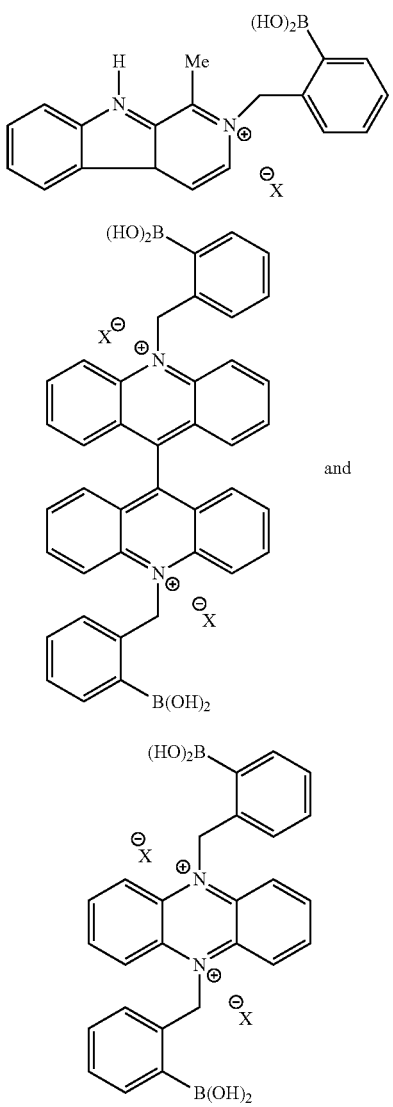

(D)
(E)
and
(F)

wherein X is chloride, bromide or iodide and R is selected from the group consisting of H, straight chain or branched $C_1$-$C_4$ alkyl group, $C_1$-$C_4$ alkoxy group, aryl group, hydroxyl, cyano, sulfonyl, and $NR^1R^2$, wherein $R^1$ and $R^2$ may be the same as or different from one another and is independently selected from the group consisting of H and $C_1$-$C_4$ alkyl groups,
with the physiological fluid for sufficient time to at least partially interact or react with the analyte; and
(b) measuring continuously the optical signal of the fluorescence compound in the presence of the analyte for a sufficient time to determine the concentration of analyte in the physiological fluid.

In the alternative, the quaternary nitrogen heterocyclic boronic acid-containing fluorophores may be used for analysis of other analytes, including but not limited to fluoride, chloride, iodide and cynanide.

In yet another aspect, the present invention relates to an ophthalmic sensor comprising:
a polymer matrix that accepts a sufficient amount of a fluorescence compound within at least the outer surfaces of the polymer matrix, wherein the fluorescence compound inter- acts or reacts with an analyte to provide an optical signal which is indicative of the analyte concentration in an ocular fluid and wherein the fluorescence compound is at least one member selected from the group consisting of:

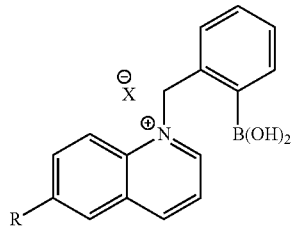

(A)

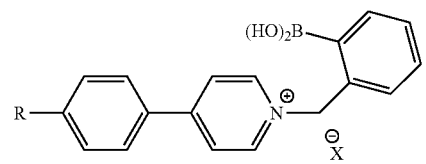

(B)

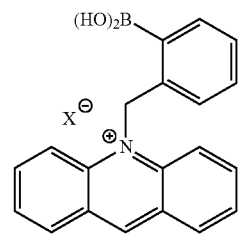

(C)

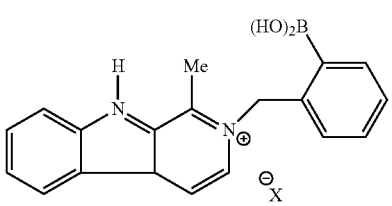

(D)

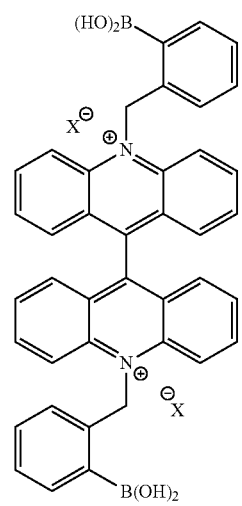

(E)

(F)

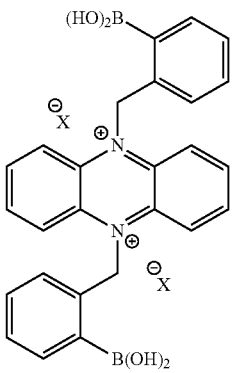

wherein X is chloride, bromide or iodide and R is selected from the group consisting of H, straight chain or branched $C_1$-$C_4$ alkyl group, $C_1$-$C_4$ alkoxy group, aryl group, hydroxyl, cyano, sulfonyl, and $NR^1R^2$, wherein $R^1$ and $R^2$ may be the same as or different from one another and is independently selected from the group consisting of H and $C_1$-$C_4$ alkyl groups;

(G)

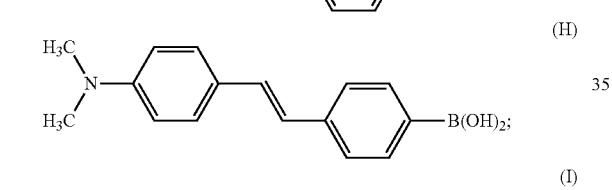

(H)

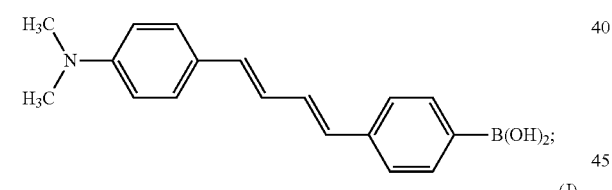

(I)

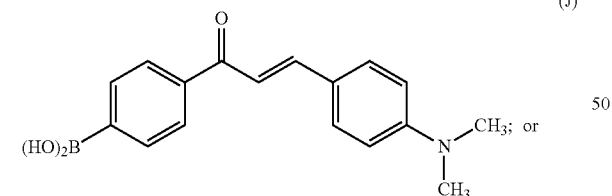

(J)

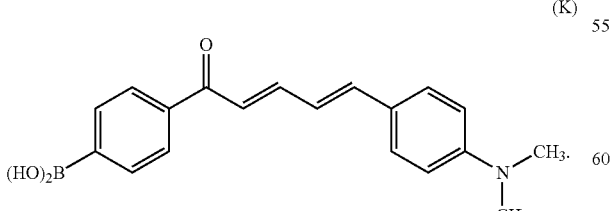

(K)

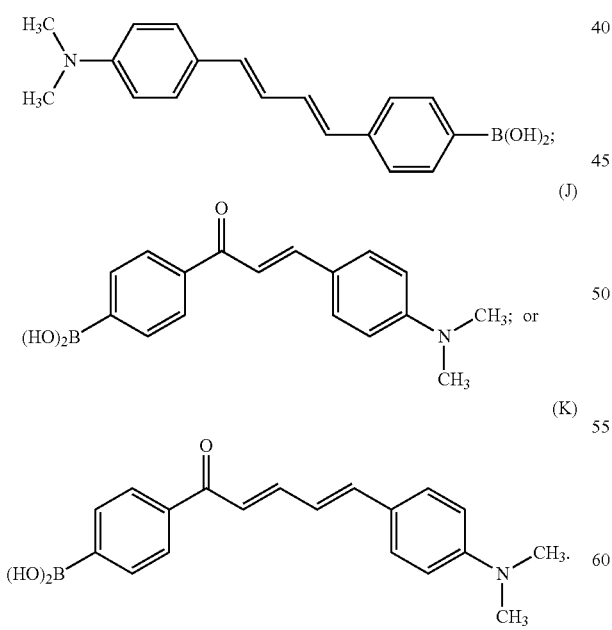

(a) contacting a fluorescence compound selected from the group consisting of:

(A)

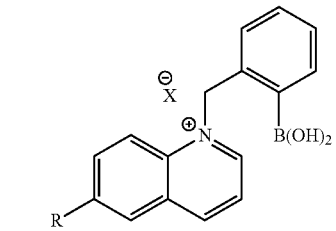

(B)

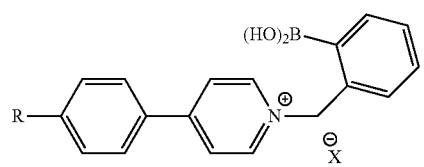

(C)

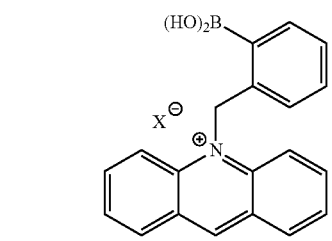

(D)

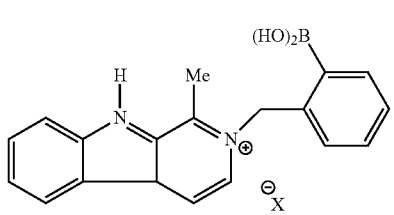

(E)

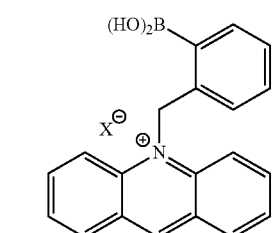

and

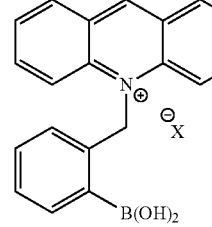

In a further aspect, the present invention relates to a method of measuring the concentration of glucose in ocular fluid, said method comprising:

-continued

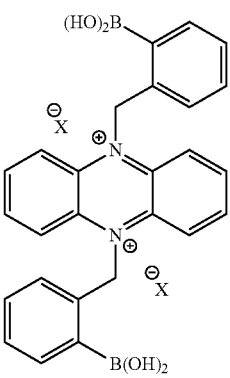
(F)

wherein X is chloride, bromide or iodide and R is selected from the group consisting of H, straight chain or branched $C_1$-$C_4$ alkyl group, $C_1$-$C_4$ alkoxy group, aryl group, hydroxyl, cyano, sulfonyl, and $NR^1R^2$, wherein $R^1$ and $R^2$ may be the same as or different from one another and is independently selected from the group consisting of H and $C_1$-$C_4$ alkyl groups, with the ocular fluid for sufficient time to at least partially interact or react with the glucose to provide an optical signal which is indicative of the glucose concentration in the ocular fluid.

The optical signal may include any change in fluorescence, such as changes in fluorescence lifetime, intensity, emission maxima, absorption maxima, anisotropy and any measure of a parameter associated with fluorescence spectroscopy.

In another aspect, the present invention relates to including a second sensing analyte compound to measure another analyte such as including sensing compounds that measure the concentration of chlorides.

A further aspect of the invention relates to a compound selected from the group consisting of:

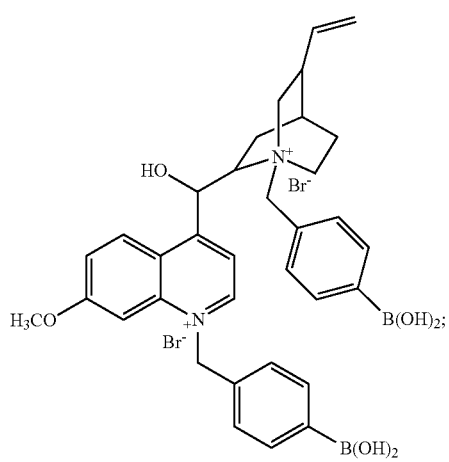
(L)

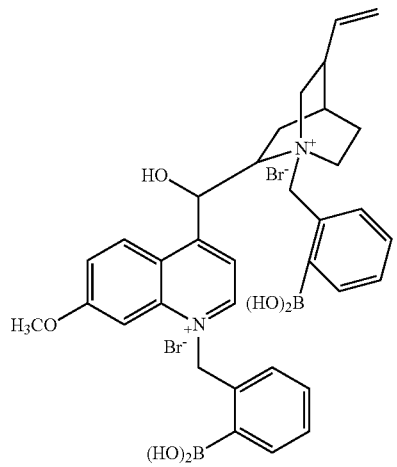
(M)

; and

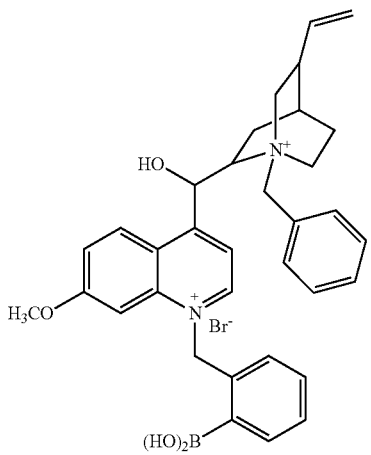
(N)

.

In another aspect, the invention relates to an analyte sensor comprising a heterocyclic quaternary nitrogen compound containing at least one heterocyclic quaternary ring nitrogen that is linked through a phenyl ring with a boronic acid group —$B(OH)_2$.

A further aspect of the invention relates to a method of determining level of an analyte at a locus containing or susceptible to presence of said analyte, such method comprising exposing to said locus an analyte sensor including a heterocyclic quaternary nitrogen compound containing at least one heterocyclic quaternary ring nitrogen that is linked through a phenyl ring with a boronic acid group —$B(OH)_2$, and determining from an optical fluorescence signal of said heterocyclic quaternary nitrogen compound the level of the analyte at such locus.

Other features and advantages of the invention will be apparent from the following detailed description, drawings and claims.

DETAILED DESCRIPTION OF PREFERRED EMBODIMENTS

Figure 1:
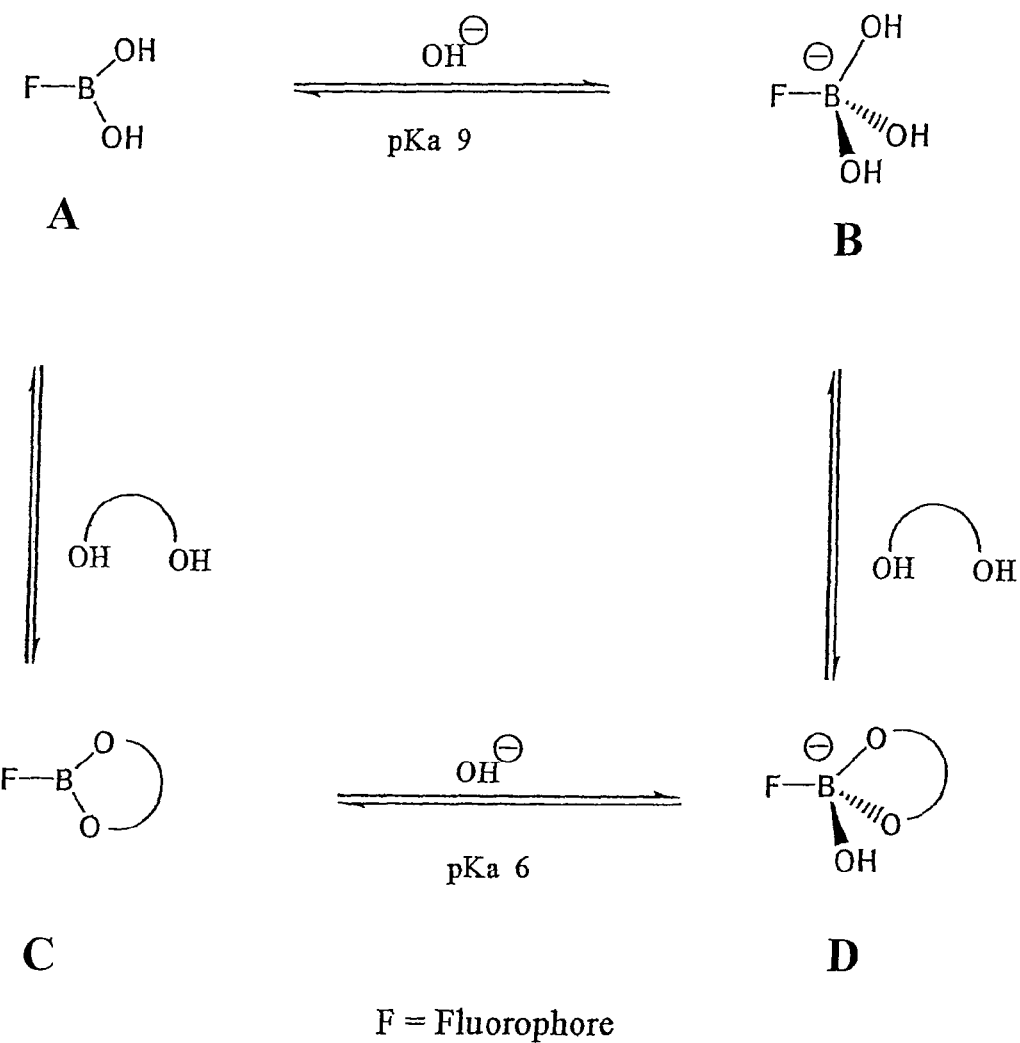
FIG. 1 shows the equilibrium reactions for the boronic acid/sugar interaction.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. As employed throughout the disclosure, the following terms shall be understood to have the following meanings.

"Biocompatible," as used herein, refers to any material or a surface of a material or an article which does not deteriorate appreciable and does not induce a significant immune response or deleterious tissue reaction, e.g., toxic reaction or significant irritation, over time when implanted into or placed adjacent to the biological tissue of a subject.

An "ophthalmic device," as used herein, refers to a contact lens (hard or soft), a corneal inlay, or implantable ophthalmic devices used in, on or about the eye or ocular vicinity.

An "ophthalmic sensor," as used herein, comprises the molecular sensing moiety and the ophthalmic device.

An "implantable ophthalmic device," as used herein, refers to an ophthalmic device, which is used in, on or about the eye or ocular vicinity. Exemplary implantable ophthalmic devices include, without limitation, an intraocular lens, a subconjunctival lens, an intracorneal lens, and a shunt or implant, e.g., a stent or a glaucoma shunt, that can rest on the cul de sac of an eye.

The term "contact lens," as used herein, is intended to encompass any hard or soft lens used on the eye or ocular vicinity for vision correction, diagnosis, sample collection, drug delivery, wound healing, cosmetic appearance, e.g., eye color modification, or other ophthalmic applications. It can be a daily-disposable contact lens, a daily-wear contact lens, or an extended-wear contact lens.

"Ophthalmically compatible," as used herein, refers to a material or surface of a material which may be in intimate contact with the ocular environment for an extended period of time without significantly modifying the ocular environment.

"Ocular environment," as used herein, refers to ocular fluids, e.g., tear fluid, and ocular tissue, e.g., the cornea, and/or conjunctiva that may come into intimate contact with a contact lens.

"Fluorophore," as used herein, is intended to encompass a chemical or biochemical molecule or fragments thereof that is capable of interacting or reacting specifically with an analyte of interest in a sample to provide one or more optical signals. Exemplary fluorophores include without limitation derivatives of phenyl boronic acid.

As used herein, "aryl" is intended to be broadly construed as referring to carbocyclic (e.g., phenyl, naphthyl), as well as heterocyclic aromatic groups (e.g., pyridyl, thienyl, furanyl, etc.), and encompassing unsubstituted as well as substituted aryl groups, wherein the substituents of substituted aryl groups may include any sterically acceptable substituents which are compatible with such aryl groups and which do not preclude the efficacy of the co-solvent compound for its intended utility. Examples of substituents for substituted aryl groups include one or more of halogen (e.g., fluoro, chloro, bromo, and iodo), amino, amido, $C_1$-$C_4$ alkyl, $C_1$-$C_4$ alkoxy, nitro, trifluoromethyl, hydroxy, hydroxyalkyl containing a $C_1$-$C_4$ alkyl moiety, etc.

"Changes in fluorescence," as used herein, encompasses changes in fluorescence lifetime, intensity, emission maxima, absorption maxima, anisotropy, and any measurable parameter associated with fluorescence spectroscopy.

"Ratiometric sensing," as used herein, encompasses comparative fluorescence intensities in the form of a ratio, whereby the numerator and denominator were measured at the same emissive wavelength (if single emission band) or different emissive wavelengths (if dual emission bands or observed red or blue shifts).

Boronic acid molecular sensing moieties for sensing monosaccharides have been described in the literature (James, T. D., et al., *Agnew. Chem. Int. Ed. Engl.*, 33, 2207 (1994); James, T. D., et al., *J. Am. Chem. Soc.*, 117, 8982 (1995); Bielecki, M., et al., *J. Chem. Soc. Perkin Trans.*, 2, 449 (1999); Dicesare, N., et al., *Anal. Biochem.*, 294, 154-160 (2001); Dicesare, N., et al., *J. Photochem. Photobiol. A*, 143, 39-47 (2001); Dicesare, N., et al., *Org. Lett.*, 3(24), 3891-3893 (2001); Dicesare, N., et al., *Tetrahedron Lett.*, 43, 2615-2618 (2002)), the contents of which are incorporated herein by reference for all purposes.

Boronic acid, —B(OH)$_2$ (represented by A in FIG. 1), is a weak Lewis acid which reversibly interacts with strong bases, e.g., hydroxyl groups, according to the reaction scheme shown in FIG. 1, to form anionic borates, —B(OH$_3$)$^-$ (represented by B in FIG. 1). The pK$_a$ of the boronic acid/anionic borate equilibrium is typically about 9.

Boronic acids also have a strong affinity for, and covalently bond with, diols, e.g., glucose, to form boronic acid diester groups (represented by C in FIG. 1), which reversibly interact with hydroxyl groups to form anionic boronate diester groups (represented by D in FIG. 1). The pK$_a$ of the boronic acid diester/boronate diester equilibrium is approximately 6, which is attributed to the increased Lewis acidity of the boronic acid diester complex. This large decrease in the pK$_a$ of the boronic acid diester complex relative to the uncomplexed boronic acid permits the detection of sugars at neutral pH because substantial optical changes are observed, e.g, the fluorescence intensity changes with pH. However, if the pH of the bodily fluid environment is less than neutral, the boronic acid molecule is preferably modified with a group such as an electron withdrawing or donation to increase sensitivity to sugars in a lower pH environment.

The invention described herein generally relates to novel fluorophore sensing moieties for detecting/measuring analytes, in particular glucose, in a body fluid and a method for using said novel molecular sensing moieties. The fluorophore sensing moieties interact or react with the analyte to provide an optical signal, which is indicative of the analyte concentration in a body fluid. Preferably, the fluorophores can be sensed using different platforms, including fluorescence intensity, lifetime based, anisotropy and ratiometric sensing. The fluorophores may be used with fluorescence quenchers, enhancers and Forster energy-transfer compounds. "Quenchers" are well known in the art and may be any compound that reduces the fluorescence intensity of the fluorophore. "Enhancers" of fluorescence include, but are not limited to, noble metal surfaces that result in increased fluorescence emission. Compounds useful for energy transfer are any compounds that can absorb the instant fluorophore's emission and fluoresce at a different wavelength.

Examples of optical signals include changes in the optical properties, including, but not limited to, a change in color, changes in intensity (absorbance or fluorescence) at the same or different wavelengths, a spectral (absorption or emission) shift, changes in lifetime of luminescence (fluorescence, phosphorescence, and the like). A change in color can be observed by the naked eye and can be used in qualitative or semi-quantitative assays.

A preferred embodiment of the invention includes a fluorescent phenyl boronic acid compound, wherein the fluorophore moiety comprises a heterocyclic quaternary nitrogen (a ring nitrogen) linked through a phenyl ring with the boronic acid moiety. Preferably, the fluorescent boronic acid compound is sensitive to the binding of monosaccharides, e.g., glucose and fructose, as well as chloride and iodide.

Measurement of monosaccharide, chloride or iodide concentration can be based upon measuring any change of fluorescence, described herein. Measurements may be performed with the fluorophore compound free in solution, contained in a matrix or bound to a substrate. Any variation are also possible, as the fluorescent boronic acid-containing compounds may be bound to other compounds in solution, such as to an antibody or protein. A substrate may be a bead in solution to which the fluorescent compound is bound. Thus the fluorophores of the present invention may be used in a diagnostic kit for measuring the concentration of monosaccharides in bodily fluids.

Additionally, the invention relates to a biocompatible sensor for detecting/measuring analytes, in particular glucose, in tears and a method of using said biocompatible sensor. The biocompatible sensor of the invention may comprise, consist essentially of, or consist of an ophthalmic device including a polymer matrix and the fluorophore in and/or on the polymeric matrix. Preferably, the ophthalmic device is an off-the-shelf, disposable plastic contact lens.

For the purpose of defining this invention, the most preferred lens is a contact lens, particularly a soft contact lens that may be used on a daily basis or for extended wear. A soft hydrogel lens is the lens most commonly worn for extended wear applications, and a poly(vinyl alcohol) (PVA) lens is most commonly worn for disposable daily use.

If the lens is an extended wear type, preferably, the polymer from which the lens is derived is formed from polymerizing a monomer from the class of hydroxy esters of acrylic acid or methacrylic acid. The preferred monomer is hydroxyethyl-methacrylate (HEMA). Advantageously, a crosslinking agent is added to the monomer composition from which the polymeric lens is derived to enhance the mechanical strength of the lens and consequently its handling properties. Crosslinking agents that can be used are polyfunctional monomers, such as ethylene glycol dimethacrylate (EGDMA).

In the event a daily disposable lens is preferred for a sensing device, a preferred group of lens-forming materials are prepolymers that are water-soluble and/or meltable. It would be advantageous that a lens-forming material comprises primarily one or more prepolymers that are preferably in a substantially pure form, e.g., purified by ultrafiltration. Examples of preferred prepolymers include, but are not limited to: water-soluble crosslinkable poly(vinyl alcohol) prepolymers as described in U.S. Pat. Nos. 5,583,163 and 6,303,687, which are incorporated by reference herein in their entireties; water-soluble vinyl group-terminated polyurethane, which is obtained by reacting an isocyanate-capped polyurethane with an ethylenically unsaturated amine (primary or secondary amine) or an ethylenically unsaturated monohydroxy compound; derivatives of polyvinyl alcohol, polyethyleneimine or polyvinylamine, which are disclosed in U.S. Pat. No. 5,849,841, which is incorporated by reference herein in its entirety; a water-soluble crosslinkable polyurea prepolymer as described in U.S. Pat. No. 6,479,587, which is incorporated by reference herein in its entirety; crosslinkable polyacrylamide; crosslinkable statistical copolymers of vinyl lactam, MMA and a co-monomer, which are disclosed in EP 655,470 and U.S. Pat. No. 5,712,356; crosslinkable copolymers of vinyl lactam, vinyl acetate and vinyl alcohol, which are disclosed in EP 712,867 and U.S. Pat. No. 5,665,840; polyether-polyester copolymers with crosslinkable side chains which are disclosed in EP 932,635; branched polyalkylene glycol-urethane prepolymers disclosed in EP 958,315 and U.S. Pat. No. 6,165,408; polyalkylene glycol-tetra (meth)acrylate prepolymers disclosed in EP 961,941 and U.S. Pat. No. 6,221,303; and crosslinkable polyallylamine gluconolactone prepolymers disclosed in WO 00/031550.

The lens can be lathe cut from a polymeric lens blank, or it can be polymerized in a mold shaped in the form of a lens, with or without the presence of an inert diluent. In either case, the hydrogel lens is desirably swollen in water so that the composition of the lens is at least 30 weight percent water.

The lens can be impregnated with the fluorophores of the present invention using conventional methods. For example, the lens can be immersed in a solvent which swells the lens and dissolves the fluorophore. The preferred solvents are volatile, short chain alcoholic solutions, e.g. ethanol. The solution is preferably a dilute aqueous solution with the concentration of the fluorophore ranging from about 0.1 to about 25 weight percent, but preferably around 1 to about 10 weight percent. The lens is left in the aqueous solution for a time sufficient for the fluorophore to penetrate and subsequently allow for the lens to equilibrate. Typically, this period of time can range between 2 to 3 hours. Afterwards, the lens is removed from solution, and the solvent is removed by simply allowing the lens to dry in air.

Alternatively, the lens can be impregnated by stirring the lens for at least several minutes in a suspension of molten fluorophore in water or buffered saline.

It is also possible to coat the surface of the lens with the fluorophore. This may be particularly desirable when the lens is a hard lens or a soft hydrophobic lens. The coating of the outer surfaces of these lenses can be accomplished using conventional methods, such as by spraying, dipping or coating with a roller. The resulting coating is optically clear, resistant to most solvents and to temperature changes, and does not delaminate, flake or crack. The coating typically is about ten microns or less in thickness, although the thickness of the coating may be varied by well-known techniques.

The invention further provides methods for making compositions including the fluorophores of the present invention, and applying them to contact lens or similar substrates to form a coating or layer of the fluorophore thereon. The method for making the composition generally comprises providing a solution, dispersion or suspension of the fluorophore and applying the solution to the substrate to form the matrix. The coating may be attached to and/or immobilized on the contact lens by any appropriate method, including covalent bonding, ionic interaction, coulombic interaction, hydrogen bonding, crosslinking (e.g., as crosslinked (cured) networks) or as interpenetrating networks, for example. If a crosslinked coating is desired, the fluorophore first is combined with a crosslinking agent. Typically, both the fluorophore and the crosslinker will be in liquid form (e.g., in a solution, dispersion or suspension), and the two solutions are combined, forming a liquid mixture. The fluorophore (with or without a crosslinker) can be applied to the substrate of choice by any suitable means for applying a liquid coating. If a crosslinker is present, the fluorophore solution may be subjected to crosslinking conditions, that may include thermal curing, ultraviolet curing, chemical curing or other curing methods.

The amount of the fluorophore which is effective as a sensitive sensing agent will depend on numerous factors. However, this amount can be readily determined empirically. For most instances, and particularly when it is desired to determine the level of glucose, the amount of fluorophore impregnated in the lens or coated on its surface should range from about 1 to about 10.0 percent of the weight of the lens or in amount sufficient to react with at least the highest concentration of glucose suspected in the tears of the testing individual.

Advantages of the preferred ophthalmic sensing device, e.g., a disposable contact lens, is the non-invasive nature of the contact lens and the sensing of the change in optical signal, which makes it an attractive method for monitoring physiological conditions, whether in response to illness or drug compliance.

An ophthalmic lens according to embodiments of the invention can be used in an analyte sensor system. The analyte sensor system comprises an ophthalmic lens and a detector configured to detect the intensity of fluorescence of the novel phenyl boronic acid-doped contact lens in the presence of analyte. For example, the detector may include a fluorophotometer. Construction of such devices is well known in the art.

Light with wavelengths which will excite the fluorescent label can be provided, for example, by a laser or a light source, such as a light-emitting diode. A fluorophotometer suitable for use with embodiments of the invention can be constructed using a light-emitting diode from Power Technology, Inc. (Little Rock, Ark.) (see March et al., *Diabetes Technol. & Ther.*, 2, 27-30 (2000)).

The detector can be a free-standing device, a table-top device, or a hand-held device. For convenience, the detector can be a miniaturized device and may be worn or carried as a personal accessory, for example, mounted in the frame of a pair of eyeglasses, clipped to an article of clothing, such as a shirt or sweater, hung around the neck, worn around the wrist, or clipped to a belt or a key ring.

If desired, the analyte sensor system also can comprise a transmitter configured to transmit a signal representing whether the analyte is detected and/or an amount of the analyte that is detected. A device configured to vary the concentration of the analyte in a body fluid or tissue, such as an infusion pump or other pump, may receive the signal and may vary the concentration response to the signal. The signal from the analyte sensor system may comprise a continuous or discontinuous telemetry signal generated by the detector. The pump may, in response to the signal, adjust the levels of the analyte in the body by providing the user with the appropriate amount of a regulator moiety, such as insulin. Infusion pumps are well known in the art for delivering a selected medication to a patient including humans and other animals in accordance with an administration schedule which can be preselected or, in some instances, preprogrammed. Pumps for use in this invention can be worn externally or can be directly implanted into the body of a mammal, including a human, to deliver a specific medication such as insulin to the mammal in controlled doses over an extended period of time. Such pumps are well known and are described, for example, in U.S. Pat. Nos. 5,957,890, 4,923,375, 4,573,994, and 3,731,681.

It has been determined that the pH of disposable plastic contact lenses is approximately 6.1 and unbufferable, and that the polarity of said lens approximates that of methanol. As such, this substantially reduces the dynamic range for sensing.

Because of the necessity of measuring analyte, e.g., glucose, changes in fluids at or below physiological pH, i.e., pH ~5-8, preferably 6-8, the $pK_a$ of the molecular sensing moiety is preferably lowered relative to published boronic acid fluorophores (BAFs), which typically have a $pK_a \gg 7$ when in the boronate diester, i.e., glucose-bound, form, and therefore are not sensitive to glucose concentration changes below physiological pH. Towards that end, the $pK_a$ of phenyl boronic acid was lowered by choosing appropriate substituents for the phenyl boronic acid molecule. For example, the addition of an electron withdrawing group and optionally an electron donating group to the phenyl boronic acid molecule reduces and increases the $pK_a$ of the boronic acid diester form, respectively. Knowing this, novel phenyl boronic acid derivatives were synthesized, which have lower glucose-bound $pK_a$ values than previously published phenyl boronic acid derivatives, said novel phenyl boronic acid compounds being superiorly sensitive to analyte, e.g., glucose, concentration changes at or below physiological pH.

Figure 2:
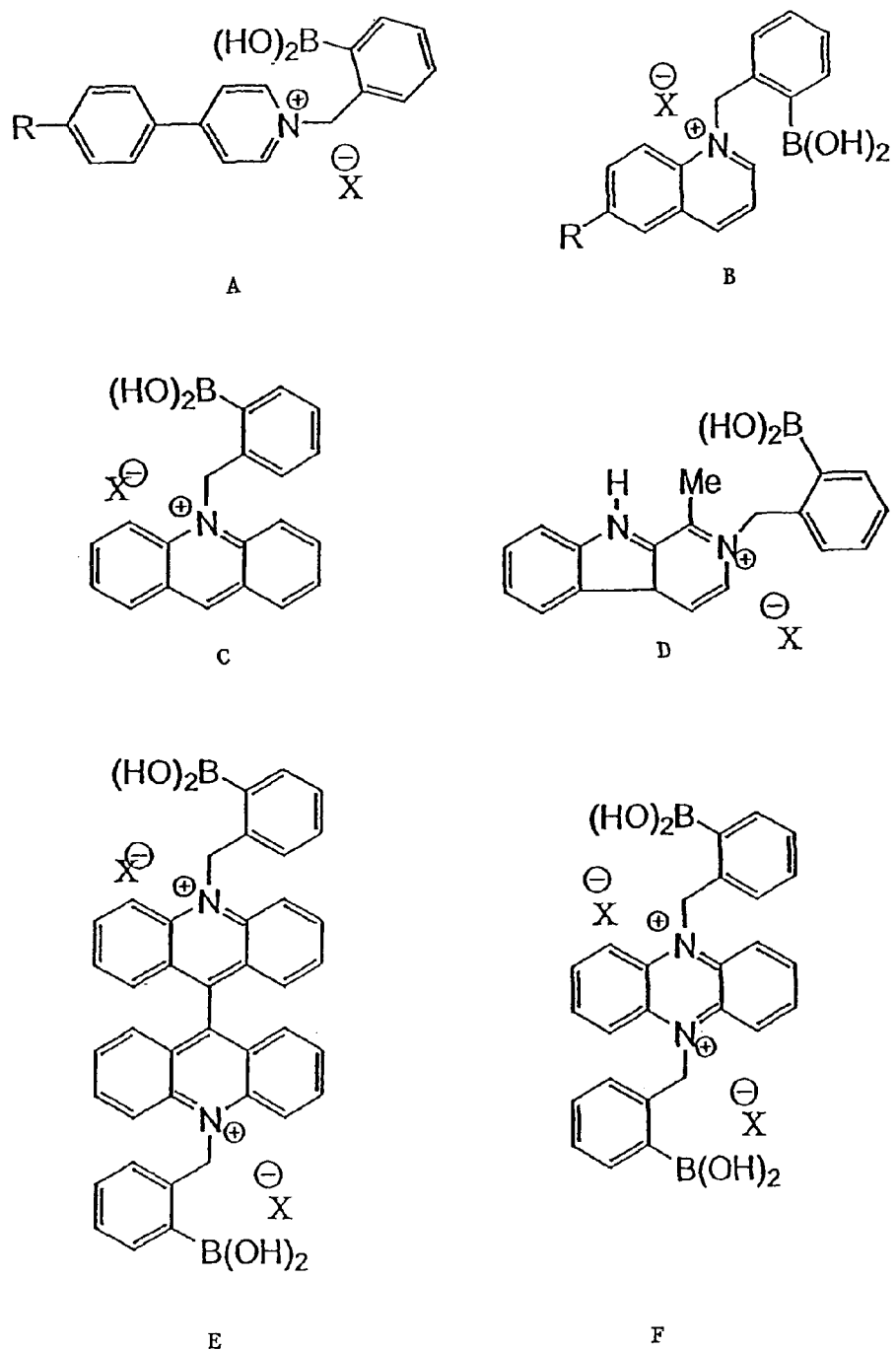
FIG. 2 shows several novel quaternary nitrogen heterocyclic boronic acid-containing fluorophores.

The novel phenyl boronic acid compounds described herein comprise a quinolinium moiety as a fluorescent indicator and a boronic acid moiety as a chelating group. Referring to FIG. 2, representations of the novel phenyl boronic acid compounds described herein are shown, each having a quinolinium backbone. In the compounds of FIG. 2, X is Cl$^-$, Br$^-$ or I$^-$ and R is selected from the group consisting of H, straight chain or branched $C_1$-$C_4$ alkyl group, $C_1$-$C_4$ alkoxy group, aryl group, hydroxyl, cyano, sulfonyl, and $NR^1R^2$, wherein $R^1$ and $R^2$ may be the same as or different from one another and is independently selected from the group consisting of H and $C_1$-$C_4$ alkyl groups. Further, although the boronic acid moiety in the compounds of FIG. 2 is shown in the ortho-position, the positioning of the boronic acid group may be meta- or para-relative to the quinolinium backbone.

Preferred quaternary nitrogen heterocyclic compounds include compound B of FIG. 2, wherein R is —CH$_3$, —OCH$_3$ or —NH$_2$ and X is Br.

Advantages of the novel phenyl boronic acid compounds described herein include, but are not limited to, excellent water solubility, simple one-step synthesis, long fluorescence lifetimes, charge stabilization, high quantum yields, increased glucose sensitivity, and compatibility with existing laser and light emitting diode excitation sources.

The method of using the novel phenyl boronic acid derivatives to determine blood monosaccharide, chloride or iodide concentrations can be provided in a kit, together with instructions for measuring the analyte concentrations. The invention provides kits which are intended for individual patient use, as well as kits for medical practitioners.

The ophthalmic lens according to the embodiments of the invention can also be provided in a kit, together with instructions for measuring analyte concentrations. The invention provides kits which are intended for individual patient use, in which the ophthalmic lens typically is a contact lens, as well as kits for medical practitioners, which can comprise any of the ophthalmic lenses or their equivalents described herein.

The invention in another aspect encompasses fluorescence compounds that contain reactive groups useful for covalent attachment to a polymeric matrix of an ophthalmic device, e.g., contact lens, or other substrate, and are capable of excellent response to glucose.

Such covalently attachable compounds contain a quaternary nitrogen heterocyclic nucleus and boronic acid functionality, as suitable for sensing glucose in the ophthalmic device or other substrate. The fluorescent nucleus of such compounds has a sugar bound pKa that is compatible with mildly acidic environments, such as are characteristic of contact lenses. The compounds are effective to transduce glucose levels in contact lenses, which have a polarity similar to methanol.

The covalently attachable fluorescence compounds respond to glucose at levels that are well over the physiological tear level. The reactive groups of such compounds enable the compounds to be covalently bonded to a contact lens, but they do not alter or influence the signaling of glucose. These reactive groups can be of any suitable type, as effective to form covalent bonds with the substrate, e.g., contact lens, material.

It will be appreciated that the fluorescence compounds should have a structure that avoids steric hindrance upon glucose binding, since the response is deteriorated by such steric hindrance.

In one specific embodiment, the reactive groups imparting covalent bonding function to the compound are allyl groups. In other embodiments, the reactive functionality imparting covalent bonding character to the fluorescence compound can be constituted by other ethylenically unsaturated groups or moieties, e.g., ethenyl or other pendant alkenyl functionality, acryloxy functionality, etc., as may be appropriate in view of the specific composition and character of the substrate to which the fluorescence compound is to be covalently bonded. In general, the reactive functionality can be any functionality that is reactive with the substrate to provide a covalently bound analyte-detecting composition that in the presence of the analyte produces an optical signal indicative of analyte level in the physiological fluid or other medium being monitored for the presence or concentration of the analyte.

By way of example, compounds covalently bondable to ophthalmic device, e.g., contact lens, substrates, can include one or more of the following compounds (L)-(N):

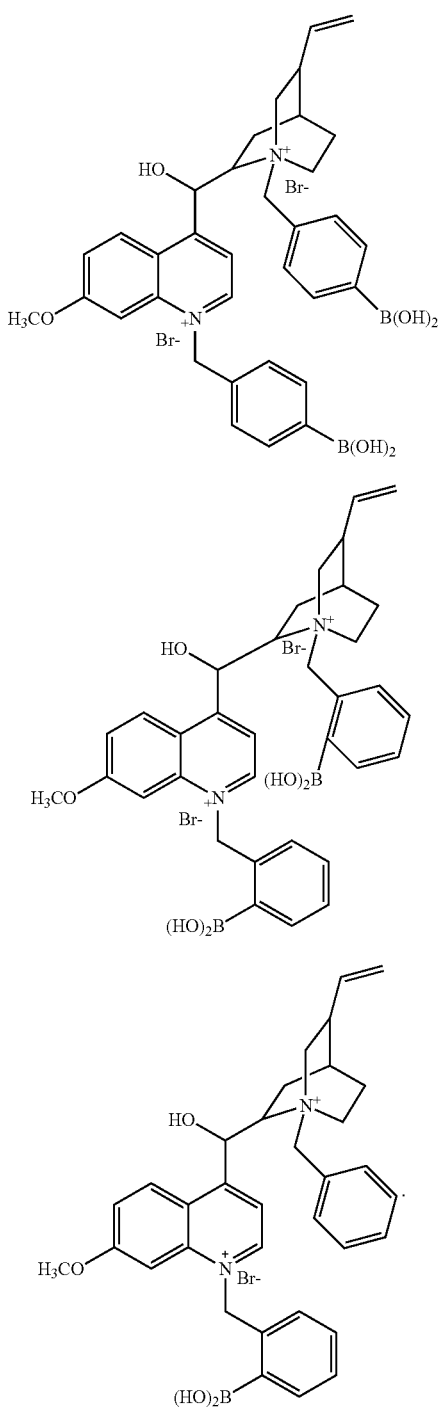

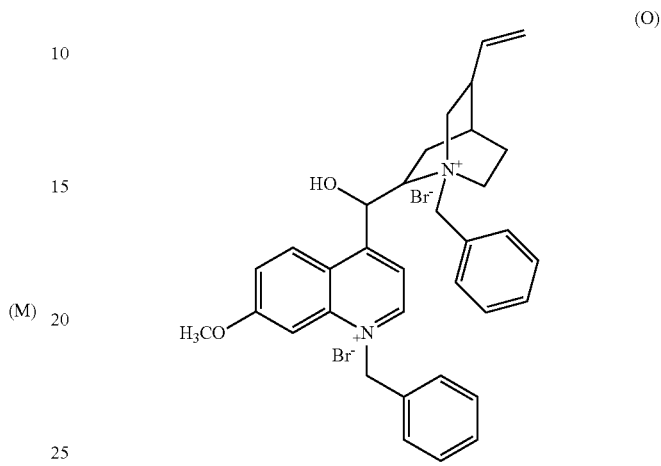

Compounds of such type are readily synthesized, within the skill of the art and without undue experimentation, to provide heterocyclic quaternary nitrogen molecules containing at least one heterocyclic quaternary nitrogen (a ring nitrogen) that is linked through a phenyl ring with a boronic acid group —B(OH)$_2$, e.g., with a benzyl group pendant from the heterocyclic quaternary nitrogen and having a boronic acid substituent on the phenyl ring of the benzyl group. Suitable compounds can include multiple heterocyclic quaternary nitrogens each having a benzyl moiety bonded thereto, with boronic acid substituents on one or more of the phenyl rings of such benzyl moieties. For example, in reference to the above illustrative compounds (L)-(N), the compounds can include two such benzyl moieties, with boronic acid substituents —B(OH)$_2$ on one or both phenyl rings of the respective benzyl moieties, in relation to the corresponding unboronated compound (O):

It will therefore be appreciated that the invention provides various classes of compounds that are effective for sensing of analytes in solution, e.g., blood, serum, urine, water, etc. Such compounds can be utilized as unanchored sensing molecules in the solution or other environments. Alternatively, such compounds can be immobilized on a substrate or be incorporated in support media for a wide variety of sensing applications.

Glucose-sensing contact lenses form a preferred embodiment of the invention, and are usefully employed by diabetics for monitoring insulin in a simple and non-invasive manner. In addition, monitoring of other physiological analytes in a contact lens having fluorophore compounds associatively incorporated in the polymeric matrix of the contact lens, or covalently bonded to such matrix, include, by way of example, and without limitation: monitoring lithium for patient stability and drug compliance; determining cholesterol levels in connection with treatment by cholesterol-lowering therapeutic agents; monitoring sodium and potassium levels for hypertension treatment; determining exposure to biological agents by tear analysis of military or first responder personnel in areas suspected or susceptible to incursion of adverse biological agents; sensing of cyanide by tear analysis of workers in the plastics industries who may encounter cyanide as a work-related toxin; and monitoring drug compliance in large clinical screens.

Various sensing applications within the scope of the present invention may utilize compounds that are highly specific in sensitivity to a target analyte species, as single compound uses that are analyte-specific in character. The invention also contemplates the use of single compounds that are sensitive to a wide variety of analytes and conditions, e.g., two or more of glucose, fructose, sodium, potassium, lithium, histamine, cholesterol, cyanide, fluoride, pH and other environmental conditions. Further, the invention contemplates the provision of multicomponent mixtures of sensing compounds, providing the capability for sensing of a spectrum of analyte target species.

The features and advantages of the invention are more fully shown with respect to the following illustrative examples and embodiments.

Methods and Materials

D-Glucose and D-fructose were purchased from Sigma and used as received. All solvents used were HPLC grade and purchased from Aldrich.

1. Preparation of o-, m- and p-N-(boronobenzyl)-6-methylquinolinium bromide (BMQBA) and N-benzyl-6-methylquinolinium bromide (BMQ)

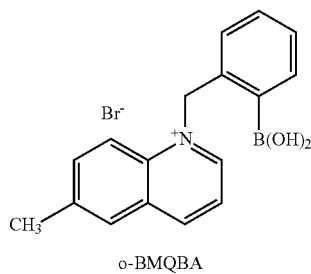 [SMILES: Cc1ccc2c(ccc[n+]2Cc2ccccc2B(O)O)c1 ; [Br-]]

o-BMQBA

The boronic acid containing fluorescent molecular sensing moieties o-, m- and p-BMQBA and the control compound MBQ were prepared using the following generic one step synthetic procedure, described herein for MBQ. Equimolar amounts of 6-methylquinoline and benzylbromide were dissolved in 10 mL dry acetonitrile in a 25 mL round bottomed flask equipped with a magnetic stirrer. The reaction mixture was allowed to stir under an inert atmosphere for 24 hrs at room temperature. During this time, a quantitative amount of quaternized salt was precipitated as a colorless solid. The solid product recovered by filtration was washed several times with dry acetonitrile and then dried under vacuum for 12 hrs. BMQ $^1$H NMR (D$_2$O) δ (ppm): 2.5 (s, 3H); 6.2 (s, 2H); 7.2-7.5 (m, 5H); 7.8 (d, 1H); 8.0 (m, 2H); 8.15 (d, 1H); 9.0 (d, 1H); and 9.3 (d, 1H). HRMS (FAB+, H$_2$O) m/e calculated: 234.1283 (M$^+$-Br). found: 234.1291 (M$^+$-Br).

The corresponding o-, m- and p-boronobenzyl bromides are employed instead of benzyl bromide to obtain the isomeric boronic acid derivatives o-, m- and p-BMQBA, respectively. o-BMQBA $^1$H NMR (D$_2$O) δ (ppm): 2.7 (s, 3H); 6.5 (s, 2H); 7.1 (s, 1H), 7.4-7.5 (m, 2H); 8.0-8.3 (m, 4H); 8.5 (d, 1H); 8.95 (d, 1H); and 9.2 (d, 1H). HRMS (FAB+, H$_2$O) m/e calculated: 346.1978 (M$^+$-Br). found: 346.1960 (M$^+$-Br). m-BMQBA $^1$H NMR (D$_2$O) δ (ppm): 2.5 (s, 3H); 6.2 (s, 2H); 7.3-7.5 (m, 2H), 7.6 (s, 1H); 7.7 (d, 1H); 7.9 (d, 1H); 8.0 (m, 2H); 8.2 (d, 1H); 9.0 (d, 1H) and 9.25 (d, 1H). HRMS (FAB+, H$_2$O) m/e calculated: 346.1978 (M$^+$-Br). found: 346.1988 (M$^+$-Br). p-BMQBA $^1$H NMR (D$_2$O) δ (ppm): 2.55 (s, 3H); 6.2 (s, 2H); 7.25 (d, 2H); 7.7 (d, 2H); 7.9 (t, 1H); 8.0-8.2 (m, 3H); 9.0 (d, 1H); and 9.25 (d, 1H). HRMS (FAB+, H$_2$O) m/e calculated: 346.1978 (M$^+$-Br). found: 346.1960 (M$^+$-Br).

2. Preparation of o-, m- and p-N-(boronobenzyl)-6-methoxyquinolinium bromide (BMOQBA) and N-benzyl-6-methoxyquinolinium bromide (BMOQ)

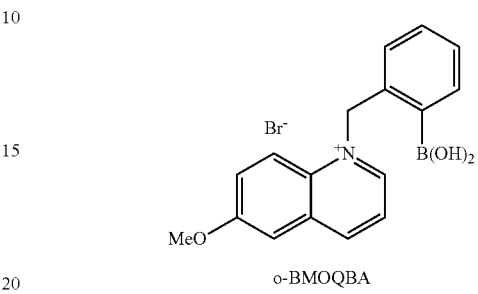

o-BMOQBA

The control compound BMOQ was conveniently prepared using the generic one-step procedure described above for the synthesis of BMQ, wherein 6-methoxyquinoline was used instead of 6-methylquinoline. BMOQ $^1$H NMR (CD$_3$OD) δ (ppm): 4.1 (s, 3H); 6.3 (s, 2H); 7.3-7.5 (m, 5H); 7.85 (m, 2H); 8.15 (t, 1H); 8.45 (d, 1H); 9.2 (d, 1H) and 9.4 (d, 1H). HRMS (FAB+, H$_2$O) m/e calculated: 250.1232 (M$^+$-Br). found: 250.1222 (M$^+$-Br).

The corresponding o-, m- and p-boronobenzyl bromides are employed instead of benzyl bromide to obtain the isomeric boronic acid derivatives o-, m- and p-BMOQBA, respectively. o-BMOQBA $^1$H NMR (CD$_3$OD) δ (ppm): 4.05 (s, 3H); 6.5 (s, 2H); 7.1 (s, 1H); 7.3-7.5 (m, 2H); 7.8-8.0 (m, 4H); 8.5 (t, 1H); 8.8 (d, 1H) and 9.1 (d, 1H). HRMS (FAB+, H$_2$O) m/e calculated: 362.1927 (M$^+$-Br). found: 362.1960 (M$^+$-Br). m-BMOQBA $^1$H NMR (CD$_3$OD) δ (ppm): 4.0 (s, 3H); 6.2 (s, 2H); 7.35-7.55 (m, 2H); 7.6-7.8 (m, 4H); 8.0 (t, 1H); 8.25 (d, 1H); 8.95 (d, 1H) and 9.15 (d, 1H). HRMS (FAB+, H$_2$O) m/e calculated: 362.1927 (M$^+$-Br). found: 362.1848 (M$^+$-Br). p-BMOQBA $^1$H NMR (CD$_3$OD) δ (ppm): 4.0 (s, 3H); 6.2 (s, 2H); 7.25 (d, 2H), 7.5-7.8 (m, 4H); 8.0 (t, 1H); 8.2 (d, 1H); 8.95 (d, 1H) and 9.15 (d, 1H). HRMS (FAB+, H$_2$O) m/e calculated: 362.1927 (M$^+$-Br). found: 362.1956 (M$^+$-Br).

3. Absorption and Emission Studies of BMQBA in the Presence and Absence of Monosaccharides The measurement of monosaccharides can be based upon measuring any of the changes in fluorescence of the disclosed fluorescent compounds, as readily determined by one skilled in the art. Measurements may be performed with the fluorophore free in solution, contained in a matrix or bound to a substrate or other compounds in solution, e.g., antibodies or proteins.

All steady state fluorescence measurements were performed in a 4×1×1 cm fluorometric plastic cuvette, using a Varian Cary Eclipse fluorometer, and all absorption measurements were performed using a Varian UV/VIS 50 spectrophotometer.

Stability ($K_S$ (mM$^{-1}$)) and dissociation ($K_D$) constants were obtained by fitting the titration curves with sugar to the relation:

$$I = \frac{I_{min} + I_{max} K_{S[sugar]}}{1 + K_{S[sugar]}}$$

where $I_{min}$ and $I_{max}$ are initial (no sugar) and final (plateau) fluorescence intensities of the titration curves and $K_D = (1/K_S)$.

Time-solved intensity decays were measured using reverse start-stop time-correlated single-photon timing (TCSPC) with a Becker and Hickl Gmbh 630 SPC PC card and unamplified MCP-PMT. Vertically polarized excitation at ~372 nm was obtained using a pulsed LED source (1 MHz repetition rate) and a dichroic sheet polarizer. The instrumental response function was ~1.1 ns fwhm. The emission was collected at the magic angle(54.7°) using a long pass filter (Edmund Scientific) which cut-off the excitation wavelengths.

The intensity decays were analyzed in terms of the multi-exponential model:

$$I(t) = \sum_i \alpha_i \exp(-t/\tau_i)$$

where $\alpha_i$ are the amplitudes and $\tau_i$ are the decay times, $\Sigma \alpha_i = 1.0$. The fractional contribution of each component to the steady-state intensity is given by:

$$f_i = \frac{\alpha_i \tau_i}{\sum_i \alpha_i \tau_i}$$

The mean lifetime of the excited state is given by:

$$\bar{\tau} = \sum_i f_i \tau_i$$

The values of $\alpha_i$ and $\tau_i$ were determined by non-linear least squares impulse reconvolution with a goodness-of-fit $\chi^2_R$ criterion.

Figure 3:
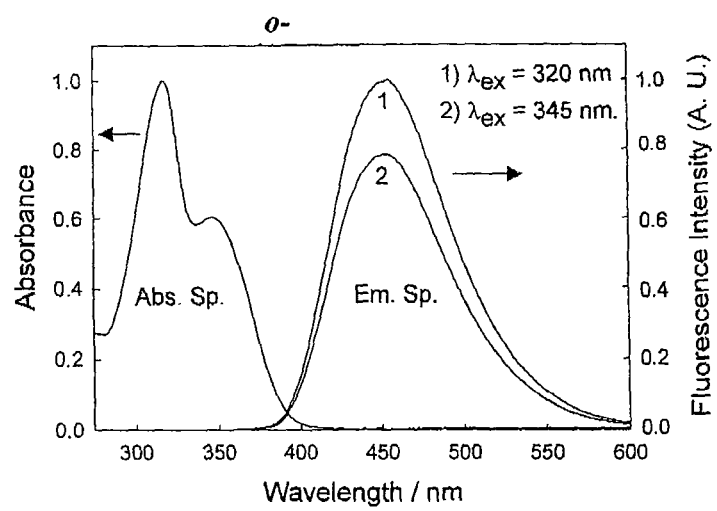
FIG. 3A shows the absorption and emission spectra of o-BMOQBA (N-(2-boronobenzyl)-6-methoxyquinolinium bromide) in $H_2O$. The spectra are also representative of the respective m- and p-isomers and the control compound BMOQ.
FIG. 3B shows the absorption and emission spectra of o-BMQBA (N-(2-boronobenzyl)-6-methylquinolinium bromide) in $H_2O$. The spectra are also representative of the respective m- and p-isomers and the control compound BMQ.
Figure 3:
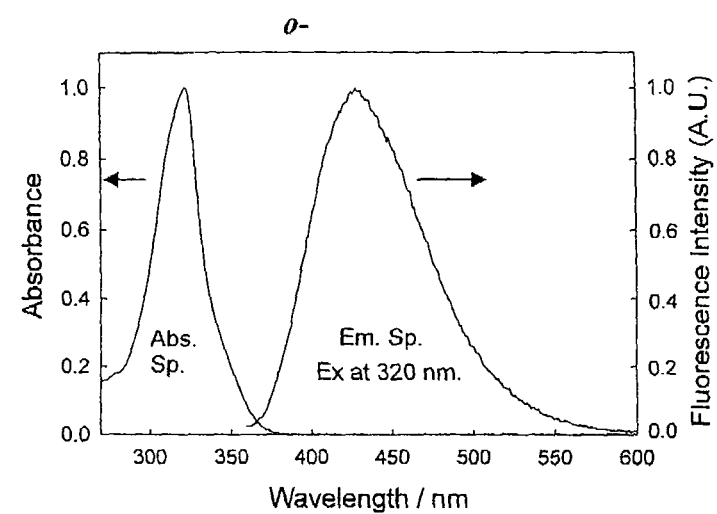

A representative absorption and emission spectra for o-BMQBA in water is shown in FIG. 3B, which corresponds to all three isomers and BMQ. BMQBA has a strong absorption band at ~320 nm, which can be assigned to n→π* transitions, and an excitation band at 427 nm, and as such, has a large Stokes shift of about 100 nm, which is ideal for fluorescence sensing. The quantum yield values of the BMQBA compounds in water relative to N-(3-sulfopropyl)-6-methoxyquinolinium (SPQ) ($\phi_f$=0.53 in water) are shown in Table 1. The low quantum yields and relatively short lifetime of the BMQBA and BMQ molecules can be attributed to a photo-induced electron transfer, whereby the phenyl ring acts as the donor and the quinolinium moiety acts as the acceptor.

TABLE 1

Spectral properties in water, $pK_a$ values in the presence and absence of 100 mM sugar, and dissociation constants of the molecular sensing moieties in pH 7.5 phosphate buffer with glucose and fructose.

|  | o-BMQBA | m-BMQBA | p-BMQBA | BMQ |
|---|---|---|---|---|
| $\lambda_{abs}$ (max)/nm | 319 | 322 | 322 | 322 |

TABLE 1-continued

Spectral properties in water, $pK_a$ values in the presence and absence of 100 mM sugar, and dissociation constants of the molecular sensing moieties in pH 7.5 phosphate buffer with glucose and fructose.

|  | o-BMQBA | m-BMQBA | p-BMQBA | BMQ |
|---|---|---|---|---|
| $\lambda_{em}$ (max)/nm | 427 | 427 | 427 | 427 |
| $\phi_f$ | 0.043 | 0.025 | 0.023 | 0.045 |
| $\tau_f$/ns (mean lifetime) | 4.01 | 3.72 | 2.10 | 2.59 |
| $pK_a$ (buffer) | 6.92 | 7.75 | 7.80 | — |
| $pK_a$ (buffer + glucose) | 6.18 | 6.85 | 6.95 | — |
| $pK_a$ (buffer + fructose) | 5.08 | 5.05 | 5.45 | — |
| $K_d$/mM (glucose) | 100 | 479 | 370 | — |
| $K_d$/mM (fructose) | 4.7 | 13.2 | 13.8 | — |

Figure 4:
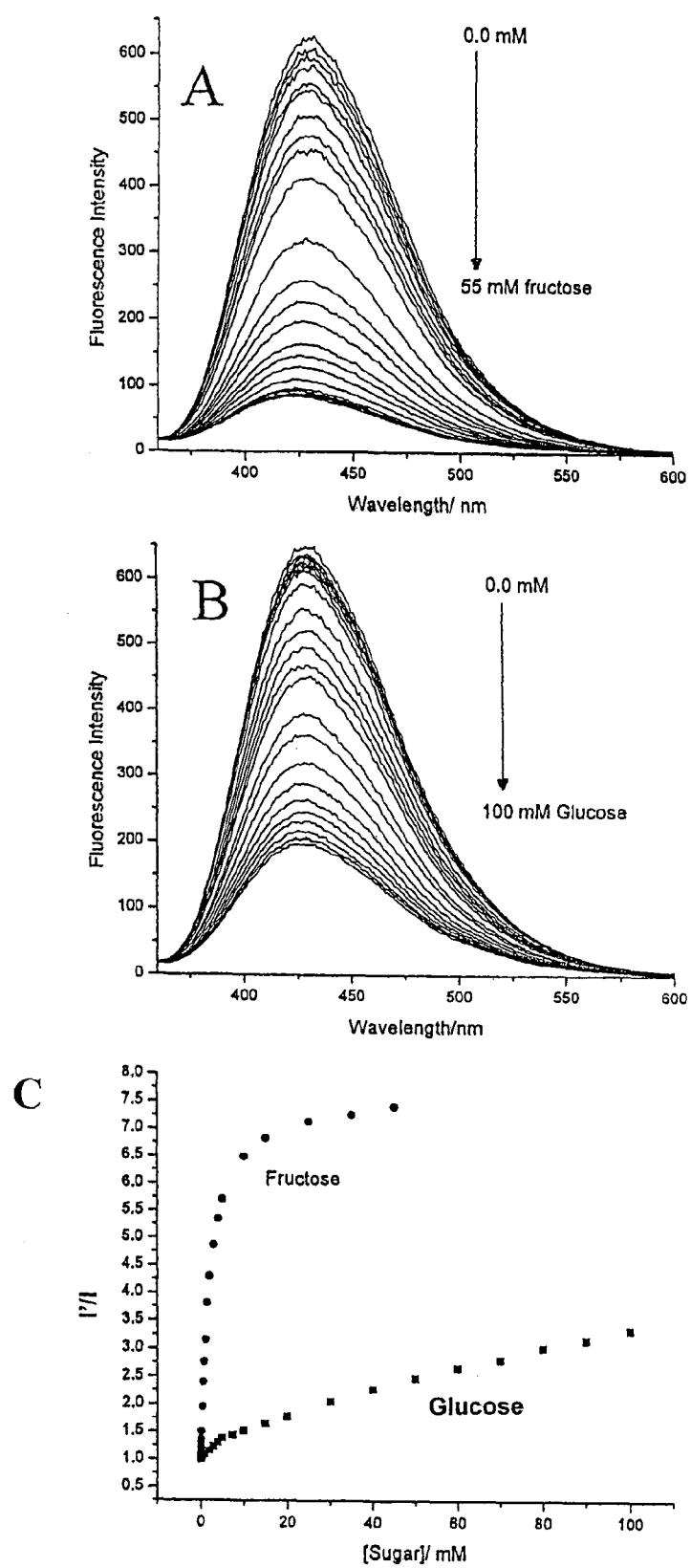
FIG. 4 shows the emission spectra of o-BMQBA in pH 7.5 phosphate buffer with (A) fructose, (B) glucose and (C) the intensity ratio at $\lambda$=427 nm in the absence, I', and presence, I, of the sugar, respectively.

The emission spectra of o-BMQBA in the presence of varying concentrations of fructose and glucose are shown in FIG. 4A and FIG. 4B, respectively. It can be seen that the fluorescence intensity of o-BMQBA in pH 7.5 phosphate buffer is inversely proportional to the glucose and fructose concentrations. Both m-BMQBA and p-BMQBA showed similar responses towards glucose, fructose and other monosaccharides. A plot of the intensity ratio, I'/I, at λ=427 nm, where I' and I represent the fluorescence intensities in the absence and presence of sugar, respectively, is shown in FIG. 4C. As expected, BMQBA shows a higher affinity for fructose than for glucose (James, T. D., et al., Agnew. Chem. Int. Ed. Engl., 33, 2207 (1994); James, T. D., et al., J. Am. Chem. Soc., 117, 8982 (1995); Bielecki, M., et al., J. Chem. Soc. Perkin Trans., 2, 449 (1999); Dicesare, N., et al., Anal. Biochem., 294, 154-160 (2001); Dicesare, N., et al., J. Photochem. Photobiol. A, 143, 39-47 (2001); Dicesare, N., et al., Org. Lett., 3(24), 3891-3893 (2001); Dicesare, N., et al., Tetrahedron Lett., 43, 2615-2618 (2002); Dicesare, N., et al., J. Phys. Chem. A, 105, 6834-6840 (2001)). It is noted that the concentration of fructose in blood is ~10 times lower than glucose, a relationship which is also thought to occur in tears (N. Dicesare, et. al., J. Bio. Med. Opt., 7(4), 538-545 (2002)). Hence, fructose is not thought to be a major interferent in physiological fluids.

Figure 5:
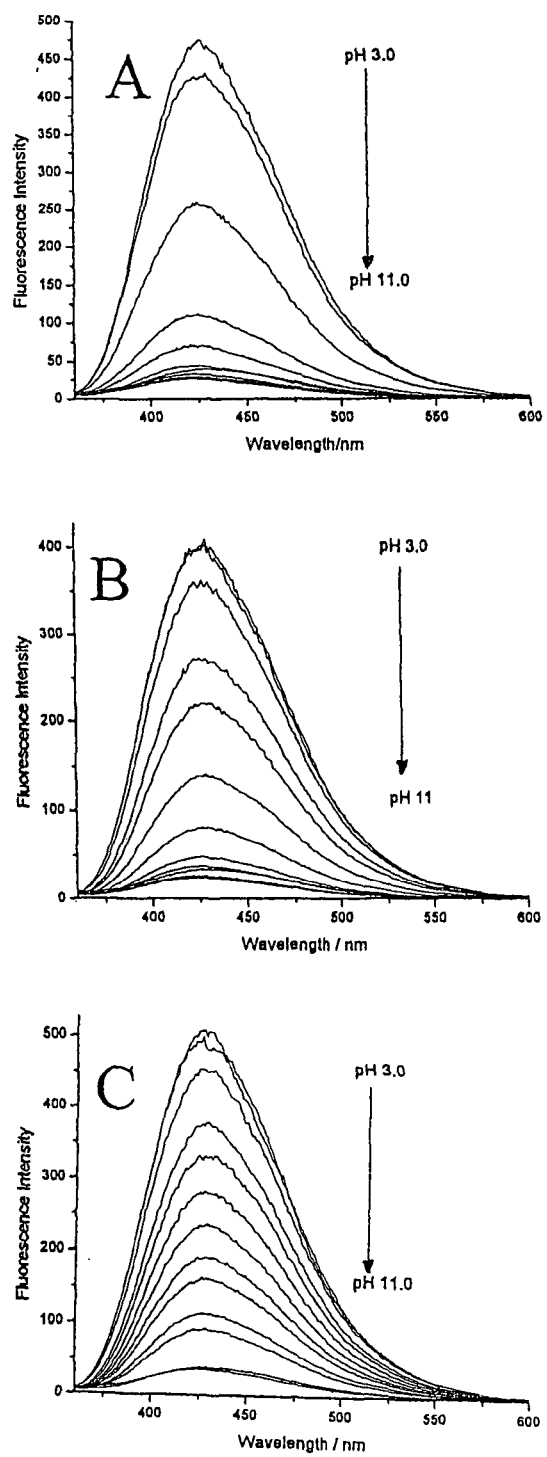
FIG. 5 shows the emission spectra of o-BMQBA in pH media with (A) 100 mM fructose, (B) 100 mM glucose and (C) buffer.
Figure 6:
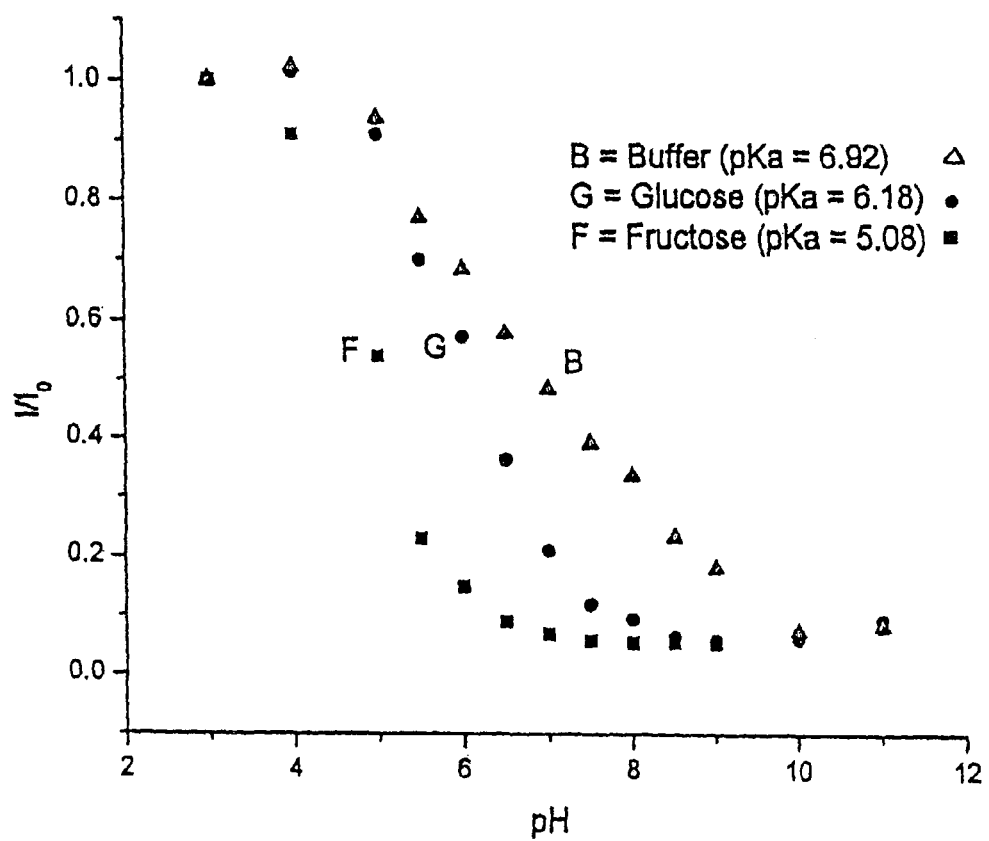
FIG. 6 shows the intensity ratio at $\lambda$=427 nm for o-BMQBA at specified pH values, I, relative to the intensity at pH 3.0, $I_o$, (in the absence of a sugar and in the presence of 100 mM of glucose or fructose).

The emission spectra of o-BMQBA at varying pH values in the absence of sugar (FIG. 5C) and in the presence of 100 mM fructose and 100 mM glucose (FIGS. 5A and 5B, respectively), show that the fluorescence intensity of o-BMQBA decreases with increasing pH (3→11), both with and without sugar. Notably, BMQ shows no change in intensity with pH change. A normalized plot of intensity at 427 nm as a function of pH is shown in FIG. 6, wherein I is the emission intensity at the specified pH and $I_o$ is the initial emission intensity at pH 3.0. Though not to be bound by theory, it is likely that the change in fluorescence intensity relative to pH value is attributed to the change in hybridization of the boron atom with increasing pH. At low pH values, the boronic acid group is an electron-deficient Lewis acid that is $sp^2$-hybridized and thus is trigonal planar. As the pH increases, the anionic form of the boronic acid begins to form, which corresponds to a more electron rich $sp^3$-hybridized boron atom and an octahedral shape. The change in the geometry of the boron atom induces the fluorescence spectral changes of the molecular sensing moieties.

The $pK_a$ values obtained from the normalized intensity plot of FIG. 6 are presented in Table 1. Based on previously reported $pK_a$ values for boronic acid compounds, these $pK_a$ values are the lowest reported for a phenyl boronic acid derivative. The quaternary nitrogen of the quinolinium moiety not only reduces the $pK_a$ of the compound, but also stabilizes the anionic boronate diester complex (represented by D in FIG. 1), which may explain the affinity of sugar for these novel compounds. Importantly, the large decrease in the $pK_a$ of the boronic acid-sugar complex relative to the uncomplexed boronic acid, allows for the quantitative detection of monosaccharides at or below physiological pH because substantial optical changes are observed.

Figure 7:
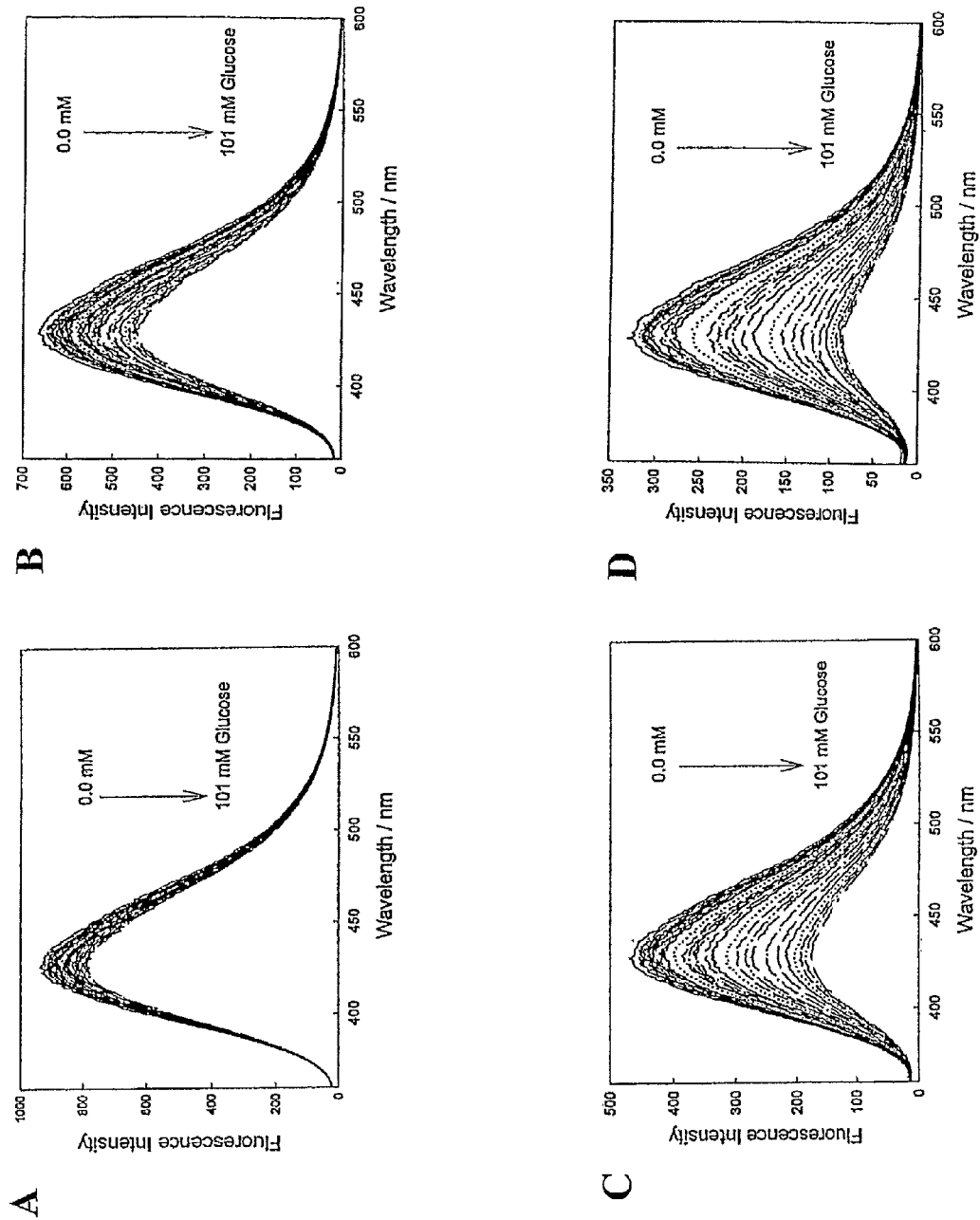
FIG. 7 shows the emission spectra of o-BMQBA in (A) pH 5.0 buffer, (B) pH 6.0 buffer, (C) pH 7.0 buffer, and (D) pH 8.0 buffer at varying glucose concentrations.

The emission spectra of o-BMQBA when both the pH media and glucose concentrations are varied are shown in FIG. 7, wherein FIGS. 7A, 7B, 7C and 7D correspond to pH 5, 6, 7, and 8 buffers, respectively. It can be seen that as the pH is increased from 5 to 8 with an increasing concentration of glucose, there is a quantifiable reduction in fluorescence intensity. This is again attributed to the increased electron density on the boron atom as the pH increases, which results in the partial neutralization of the positively charged quaternary nitrogen of the quinolinium moiety, which has been termed herein "charge neutralization-stabilization mechanism." Just as an increased pH increases the electron density on the boron atom, the binding of glucose at the boron atom also induces charge neutralization-stabilization, as schematically shown below. With stabilization, e.g., binding of glucose to the boronic acid moiety, there is a quantifiable reduction in fluorescence intensity.

Figure 10:
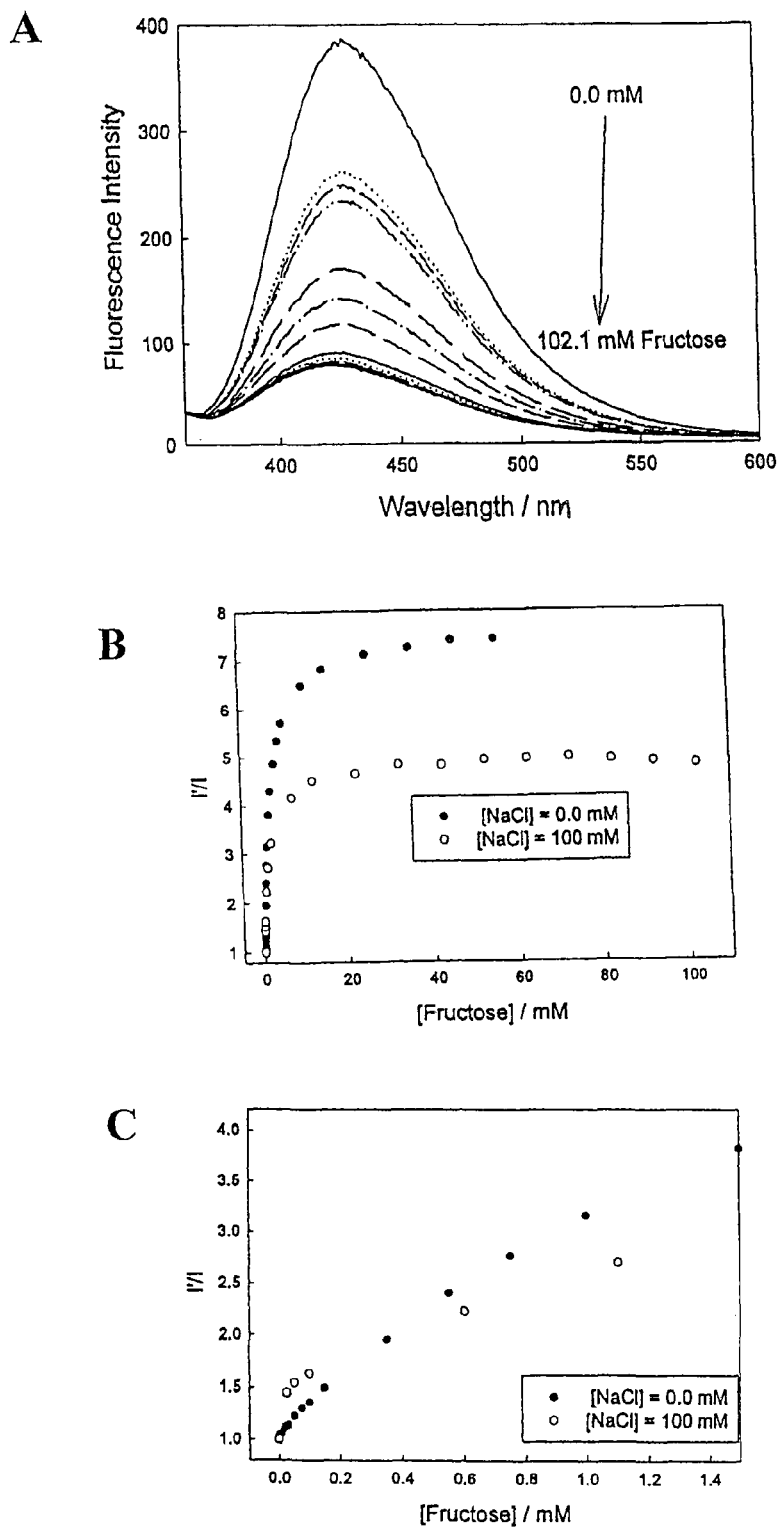
FIG. 10A shows the emission spectra of o-BMQBA in pH 7.5 phosphate buffer having 100 mM NaCl at varying fructose concentrations.
FIG. 10B shows the intensity ratio at $\lambda$=427 nm for o-BMQBA at specified fructose concentrations in the absence and presence of NaCl, where I' is the fluorescence intensity at 0 mM fructose and I is the corresponding intensity at the specified fructose concentration.
FIG. 10C shows the intensity ratio at $\lambda$=427 nm for o-BMQBA at low fructose concentrations in the absence and presence of NaCl, where I' is the fluorescence intensity at 0 mM fructose and I is the corresponding intensity at the specified fructose concentration.
Figure 11:
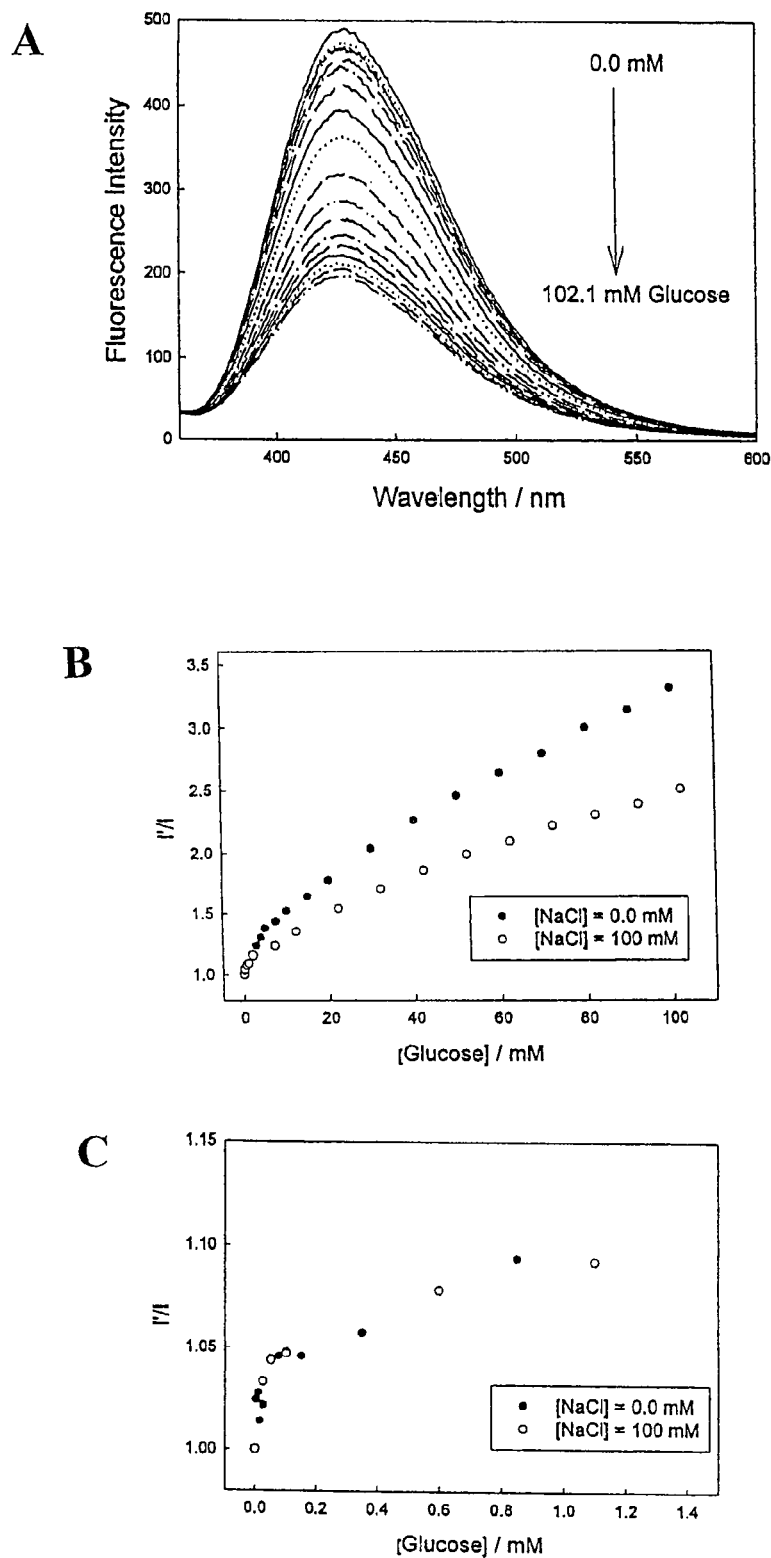
FIG. 11A shows the emission spectra of o-BMQBA in pH 7.5 phosphate buffer having 100 mM NaCl at varying glucose concentrations.
FIG. 11B shows the intensity ratio at $\lambda$=427 nm for o-BMQBA at specified glucose concentrations in the absence and presence of NaCl, where I' is the fluorescence intensity at 0 mM glucose and I is the corresponding intensity at the specified glucose concentration.
FIG. 11C shows the intensity ratio at $\lambda$=427 nm for o-BMQBA at low glucose concentrations in the absence and presence of NaCl, where I' is the fluorescence intensity at 0 mM glucose and I is the corresponding intensity at the specified glucose concentration.

Geddes, C. D., et al., *J. Heterocyclic Chem.*, 36(4), 949-951 (1999); Geddes, C. D., et al., *Anal. Biochem.*, 293(1), 60-66 (2001)), the fluorescence intensity and intensity ratios of o-BMQBA in pH 7.5 buffer having 100 mM NaCl with varying quantities of fructose or glucose was measured and shown in FIGS. 10 and 11, respectively, where I' corresponds to the intensity in the absence of fructose and I corresponds to the intensity at the specified fructose concentration. It can be seen that although chloride quenched the intensity of the emission in the presence of fructose, the intensity ratio change for fructose is still significant, amounting to a 4-fold decrease in fluorescence intensity at 60 mM fructose (see FIG. 10B). The quenching effect was less significant at lower concentrations of fructose (see FIG. 10C) and for glucose concentrations, both high and low (see FIGS. 11B and 11C). This minimal quenching effect for BMQBA is supported by the calculated Stern-Volmer constants, $K_w$, for the BMQBA compounds in water, which were determined to be $44.0\,M^{-1}$, $20.0\,M^{-1}$, $17.0\,M^{-1}$ and $35.0\,M^{-1}$ for o-BMQBA, m-BMQBA, p-BMQBA and BMQ, respectively. These are small quenching constants that are readily accounted for using simple corrections in the fluorescence signal, as readily determined by one skilled in the art of fluorescence.

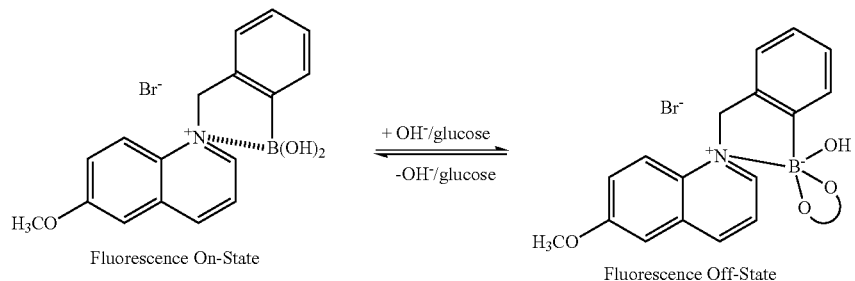

Fluorescence On-State ⇌ Fluorescence Off-State

Figure 8:
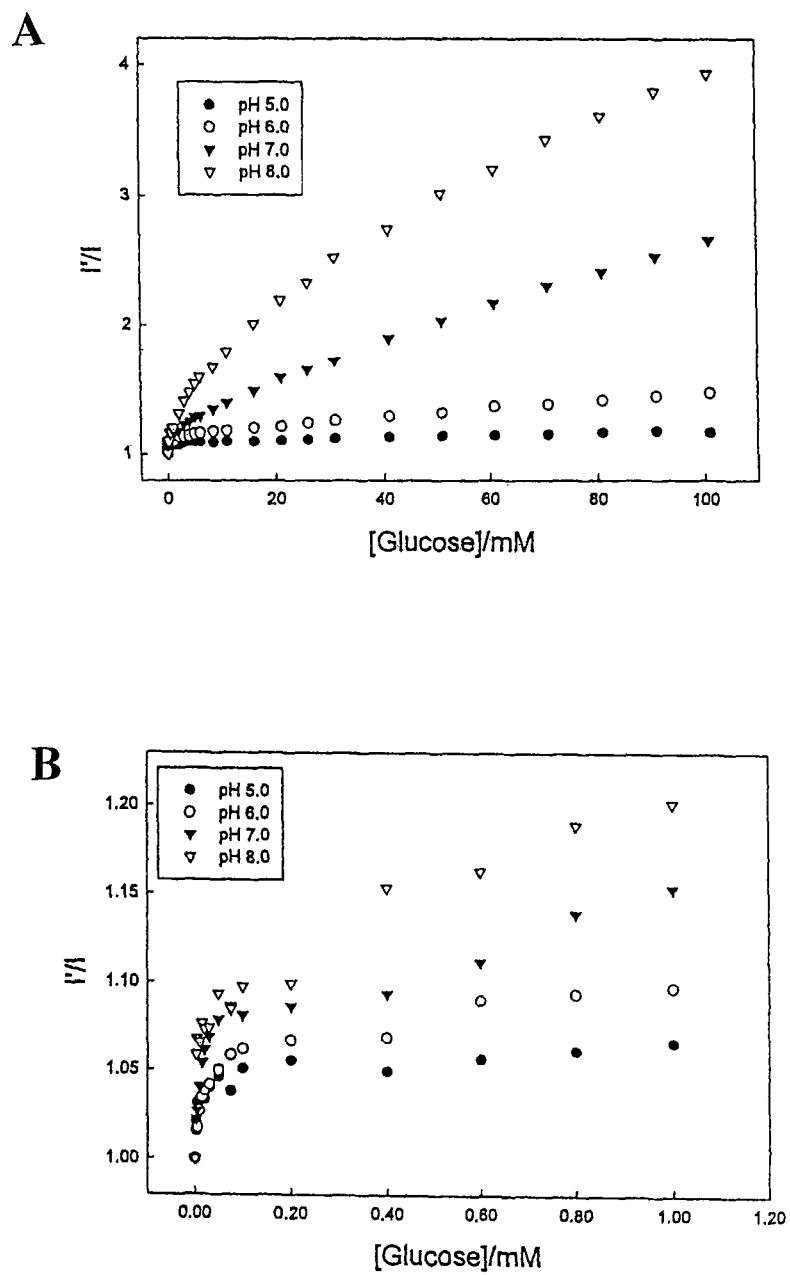
FIG. 8 shows the intensity ratio at $\lambda$=427 nm for o-BMQBA at varying buffered pH values and glucose concentrations at (A) high glucose concentrations and (B) low glucose concentrations (typical of those found in tears).
Figure 9:
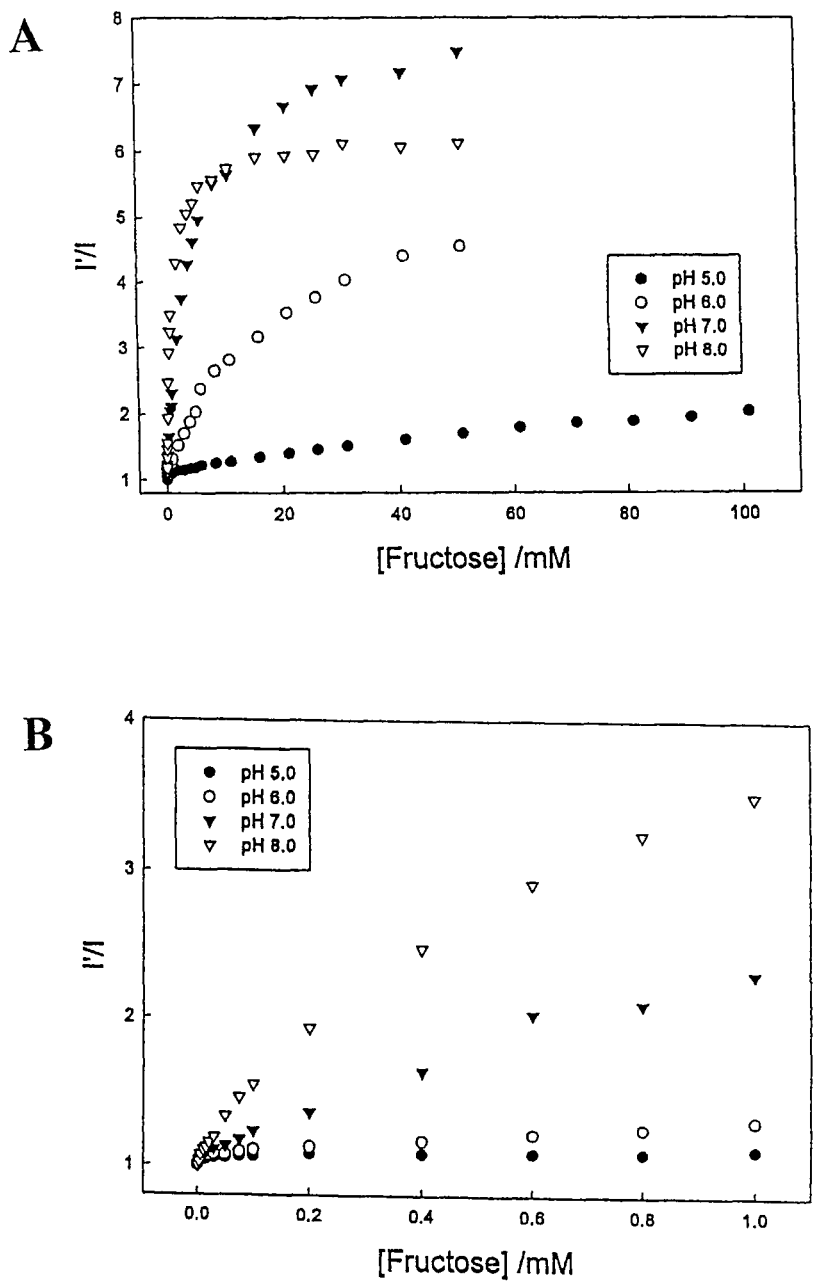
FIG. 9 shows the intensity ratio at $\lambda$=427 nm for o-BMQBA at varying buffered pH values and fructose concentrations at (A) high fructose concentrations and (B) low fructose concentrations.

The intensity ratio for o-BMQBA in buffered media (pH 5-8) at various glucose concentrations is shown in FIG. 8A, wherein I' corresponds to the intensity in the absence of glucose and I corresponds to the intensity at the specified glucose concentration. In addition, the intensity ratio for o-BMQBA in buffered media (pH 5-8) at low glucose concentrations, typical of those found in tears, is shown in FIG. 8B. Correspondingly, the intensity ratio for o-BMQBA in buffered media (pH 5-8) at various fructose concentrations is shown in FIGS. 9A and 9B.

For glucose, in the pH 6 to 7 range, it can be seen that for 60 mM glucose, there is a 1.4→2.1 fold decrease in fluorescence intensity (see FIG. 8A) and about a 10% decrease in fluorescence intensity at 0.60 mM glucose (see FIG. 8B). The latter change is especially important when assessing the concentration of glucose in tears because tear glucose levels are reported to change from ~500 μM to 5 mM for diabetics (Gasser, A. R., et al., *Am. J. Ophthalmology*, 65(3), 414-420 (1968); Das, B. N., et al., *J. Indian Med. Assoc.*, 93(4), 127-128 (1995)). In a corresponding manner, for fructose in the pH 6 to 7 range, there is a 4→6 fold decrease in fluorescence intensity at 50 mM fructose and a 1.3→2.0 fold decrease in intensity at 0.60 mM fructose. These are measurable differences which allow for the quantification of monosaccharide concentrations.

Because physiological fluids contain chloride ions, which are well known quenchers of quinolinium fluorescence (Geddes, C. D., *Meas. Sci. Technol.*, 12 (9), R53-R88 (2001);

Notably, because chloride ions are known in the art to quench the fluorescence intensity of quinolinium derivatized compounds, the heterocyclic compounds can be used to qualitatively and quantitatively determine the presence of chloride ions in a solution. Moreover, because the quenching of fluorescence is not a selective process, any fluorophore quenched by chloride is also quenched by bromide and iodide to an even more substantial extent, allowing for the determination of bromide or iodide concentrations as well. Generally, fluorophores that are quenched by chloride are not quenched by fluoride, which is often attributed to the "heavy-atom effect" (Geddes, C. D., *Meas. Sci. Technol.*, 12, R53 (2001); Lakowicz, J. R., *Principles of Fluorescence Spectroscopy*, 2nd ed., Kluwer/Academic Plenum Publishers, New York, 1997). It is however noted that the inventors have surprisingly discovered that N-(2-boronobenzyl)-6-aminoquinolinium bromide (BAQBA), which has the general structure of B in FIG. 2, is very sensitive to fluoride and is able to detect fluoride concentrations below about 50 mM.

4. Absorption and Emission Studies of BMOQBA in the Presence and Absence of Monosaccharides As introduced above, the measurement of monosaccharides can be based upon measuring any of the changes in fluorescence of the disclosed fluorescent compounds, as readily determined by one skilled in the art. Measurements may be performed with the fluorophore free in solution, contained in a matrix or bound to a substrate or other compounds in solution, e.g., antibodies or proteins.

A representative absorption and emission spectra for o-BMOQBA in water is shown in FIG. 3A, which corresponds to all three isomers and BMOQ. BMOQBA has a strong absorption band at ~345 nm, which can be assigned to n→π* transitions, and an excitation band at ~450 nm, and as such, has a large Stokes shift of about 100 nm, which is ideal for fluorescence sensing. The quantum yield values of the BMOQBA compounds in water relative to N-(3-sulfopropyl)-6-methoxyquinolinium (SPQ) ($\phi_f$=0.53 in water) are shown in Table 2. The lower quantum yields of the BMOQBA molecules relative to BMOQ can possibly be explained by the interaction between the boronate diester (represented by D in FIG. 1) and the positively charged nitrogen center at neutral pH, which is expected to be most prominent for the o-BMOQBA isomer, hence the lowest quantum yield. We can only speculate as to the quantum yield differences between the m-BMOQBA and p-BMOQBA compounds, which may be attributed to through-bond and through-space mechanisms.

TABLE 2

Spectral properties in water, $pK_a$ values in the presence and absence of 100 mM sugar, and dissociation constants of the molecular sensing moieties in pH 7.5 phosphate buffer with glucose and fructose.

|  | o-BMOQBA | m-BMOQBA | p-BMOQBA | BMOQ |
| --- | --- | --- | --- | --- |
| $\lambda_{abs}$ (max)/nm | 318, 346 | 318, 347 | 318, 346 | 318, 347 |
| $\lambda_{em}$ (max)/nm | 450 | 450 | 451 | 453 |
| $\phi_f$ | 0.46 | 0.51 | 0.49 | 0.54 |
| $\tau_f$/ns (mean lifetime) | 26.7 | 25.9 | 24.9 | 27.3 |
| $pK_a$ (buffer) | 7.90 | 7.70 | 7.90 | — |
| $pK_a$ (buffer + glucose) | 6.62 | 6.90 | 6.90 | — |
| $pK_a$ (buffer + fructose) | 4.80 | 5.00 | 5.45 | — |
| $K_d$/mM (glucose) | 49.5 | 1000 | 430 | — |
| $K_d$/mM (fructose) | 0.65 | 1.8 | 9.1 | — |

Figure 12:
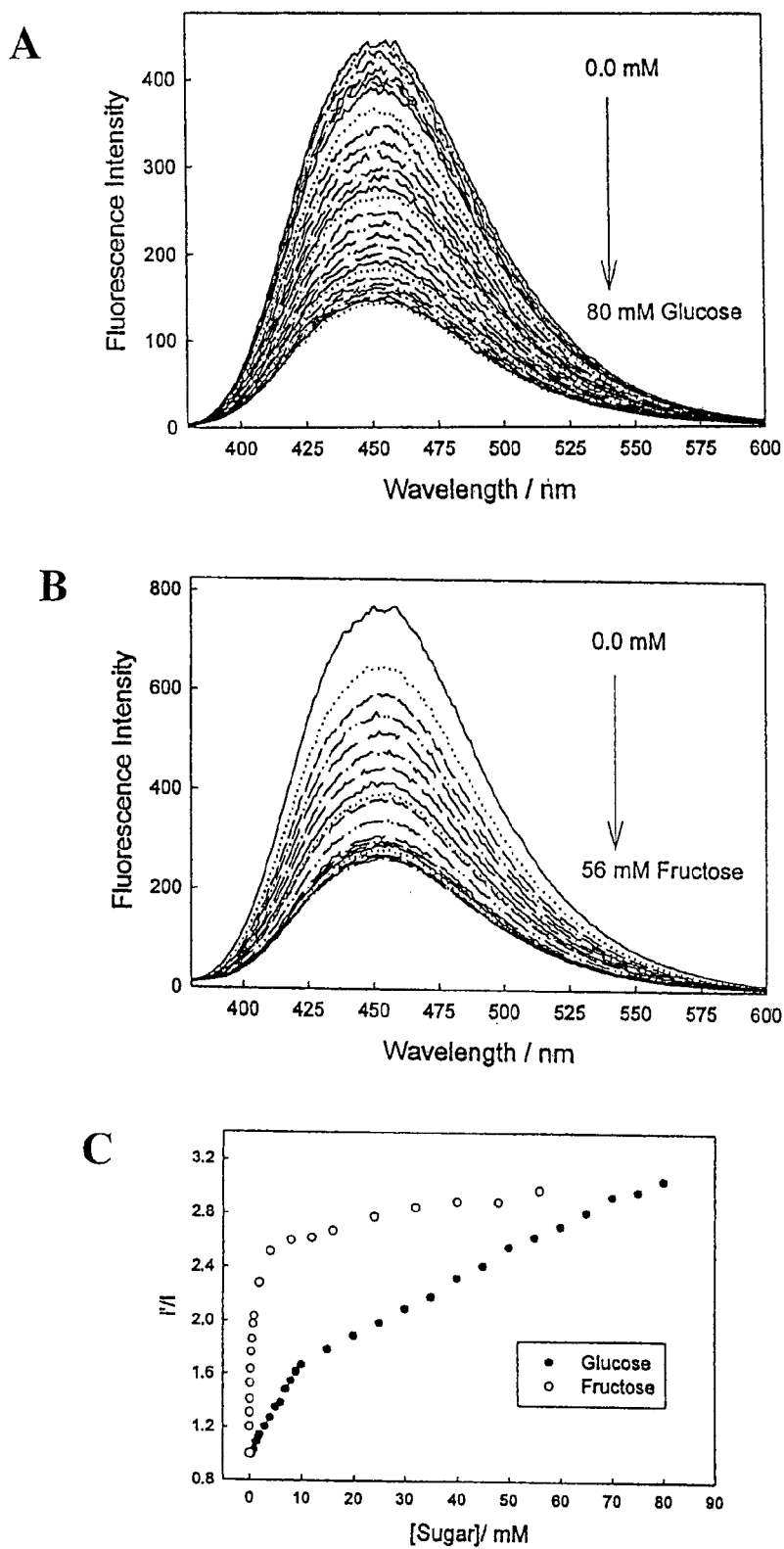
FIG. 12 shows the emission spectra ($\lambda_{ex}$=345 nm) of o-BMOQBA in pH 7.5 phosphate buffer with (A) glucose, (B) fructose and (C) the intensity ratio at $\lambda$=450 nm in the absence, I', and presence, I, of the sugar, respectively.

The emission spectra of o-BMOQBA in the presence of varying concentrations of glucose and fructose are shown in FIG. 12A and FIG. 12B, respectively. It can be seen that the fluorescence intensity of o-BMOQBA in pH 7.5 phosphate buffer is inversely proportional to the glucose and fructose concentrations. Both m-BMOQBA and p-BMOQBA showed similar responses towards glucose, fructose and other monosaccharides. A plot of the intensity ratio, I'/I, at λ=450 nm, where I' and I represent the fluorescence intensities in the absence and presence of sugar, respectively, is shown in FIG. 12C. As expected, BMOQBA shows a higher affinity for fructose than for glucose (James, T. D., et al., *Agnew. Chem. Int. Ed. Engl.*, 33, 2207 (1994); James, T. D., et al., *J. Am. Chem. Soc.*, 117, 8982 (1995); Bielecki, M., et al., *J. Chem. Soc. Perkin Trans.*, 2, 449 (1999); Dicesare, N., et al., *Anal. Biochem.*, 294, 154-160 (2001); Dicesare, N., et al., *J. Photochem. Photobiol. A*, 143, 39-47 (2001); Dicesare, N., et al., *Org. Lett.*, 3(24), 3891-3893 (2001); Dicesare, N., et al., *Tetrahedron Lett.*, 43, 2615-2618 (2002); Dicesare, N., et al., *J. Phys. Chem. A*, 105, 6834-6840 (2001)). Referring to FIG. 12C, there is a 2.8-fold change in intensity by the addition of 60 mM sugar. Interestingly, useful intensity changes are shown in the 2 mM→40 mM range, which corresponds to the glucose concentration of a healthy person to the upper limit experienced by a diabetic (DiCesare, N., et al., *J. Bio. Med. Opt.*, 7(4), 538-545 (2002)).

Figure 13:
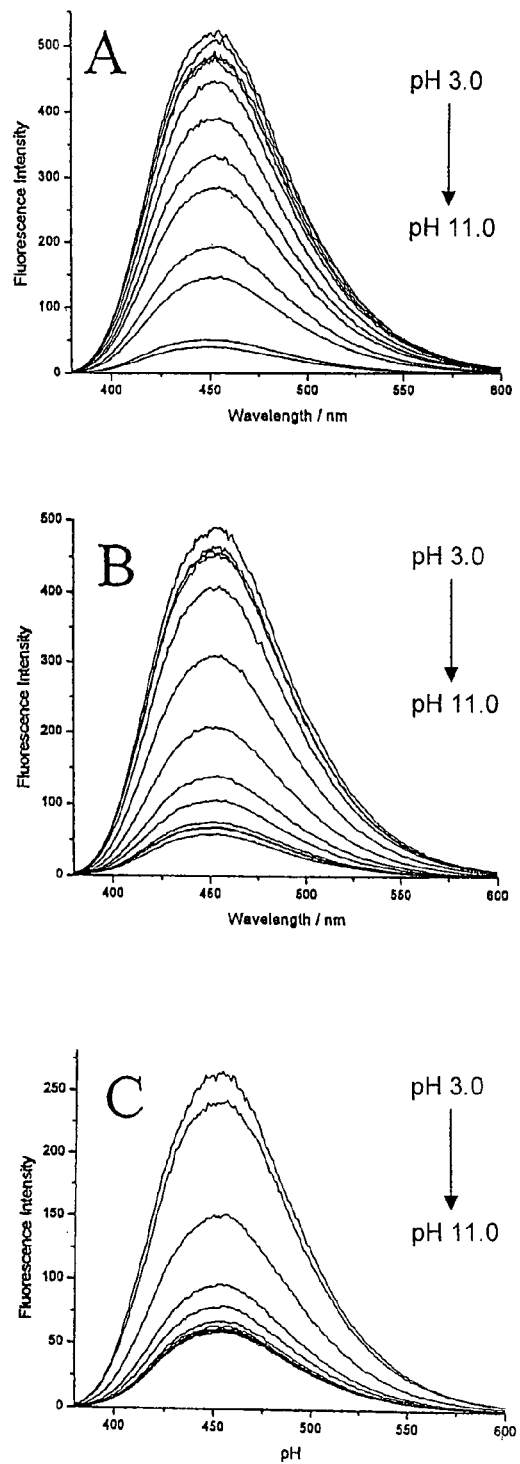
FIG. 13 shows the emission spectra ($\lambda_{ex}$=345 nm) of o-BMOQBA in pH media with (A) buffer, (B) 100 mM glucose, and (C) 100 mM fructose.
Figure 14:
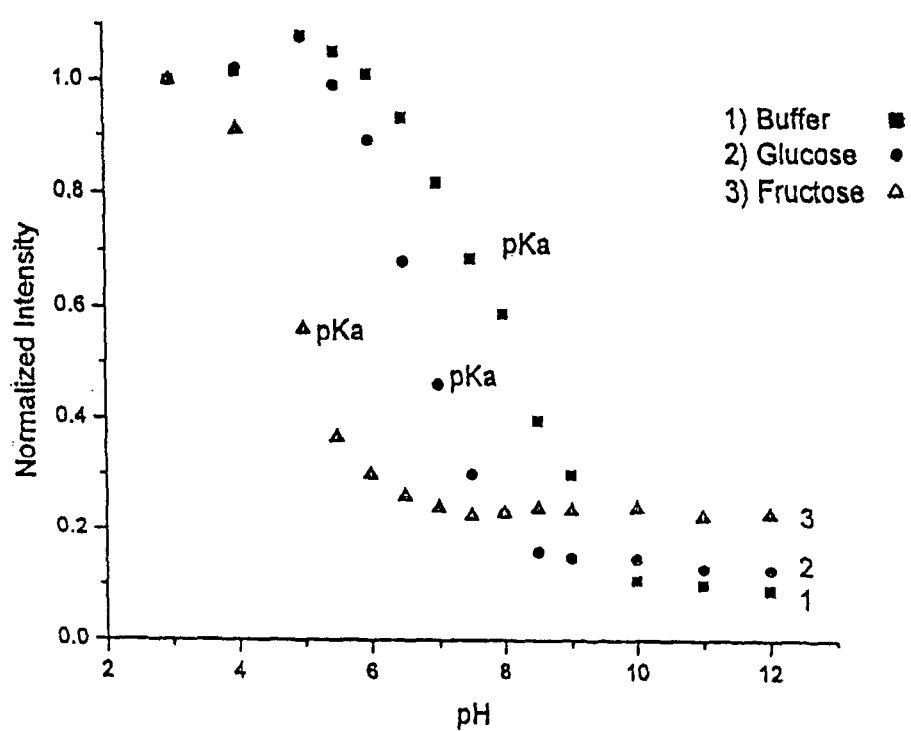
FIG. 14 shows the normalized intensity ratio at $\lambda$=450 nm ($\lambda_{ex}$=345 nm) for o-BMOQBA at specified pH values, wherein the normalized intensity is the fluorescence intensity at the specified pH, I, relative to the intensity at pH 3.0, $I_o$, (in the absence of a sugar and in the presence of 100 mM of glucose or fructose).

The emission spectra of o-BMOQBA at varying pH values in the absence of sugar (FIG. 13A) and in the presence of 100 mM glucose and 100 mM fructose (FIGS. 13B and 13C, respectively), show that the fluorescence intensity of o-BMOQBA decreases with increasing pH (3→11), both with and without sugar. Notably, BMOQ shows no corresponding change in intensity with pH change. A normalized plot of intensity at 450 nm as a function of pH is shown in FIG. 14, wherein normalized intensity is the emission intensity at the specified pH, I, relative to the initial emission intensity at pH 3.0, $I_o$. As discussed with reference to o-BMQBA, the change in the geometry of the boron atom may explain the fluorescence spectral changes of the molecular sensing moieties.

The $pK_a$ values obtained from the normalized intensity plot of FIG. 14 are presented in Table 2. Comparing the $pK_a$ values of previously reported boronic acid compounds relative to the novel BMOQBA isomers, these $pK_a$ values are relatively low. As discussed with reference to o-BMQBA, the lower $pK_a$ values can be attributed to the increased Lewis acidity of the boronate diester complex (represented by D in FIG. 1). Importantly, the large decrease in the $pK_a$ of the boronic acid-sugar complex relative to the uncomplexed boronic acid, allows for the quantitative detection of monosaccharides at or below physiological pH because substantial optical changes are observed.

Figure 15:
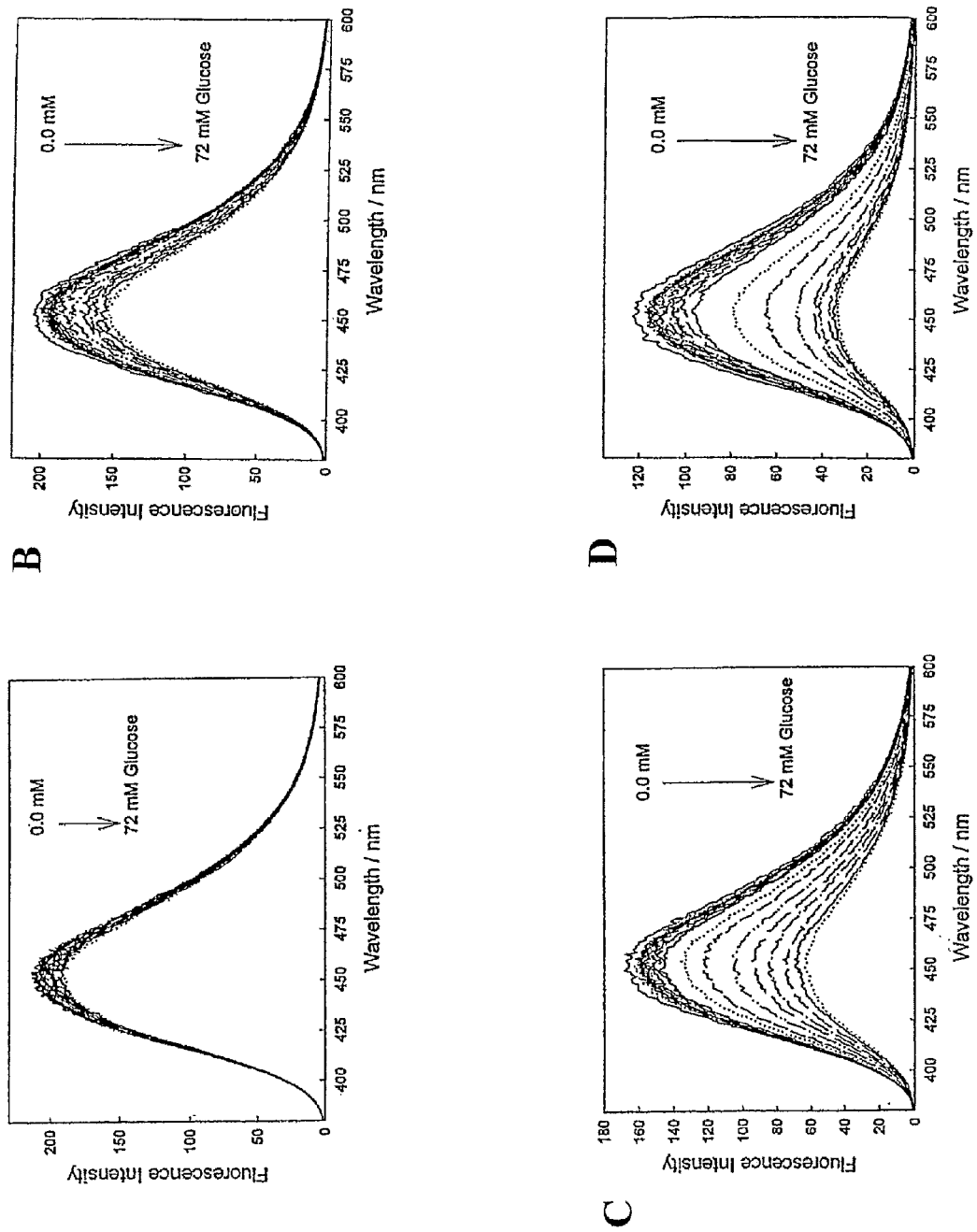
FIG. 15 shows the emission spectra ($\lambda_{ex}$=345 nm) of o-BMOQBA in (A) pH 5.0 buffer, (B) pH 6.0 buffer, (C) pH 7.0 buffer, and (D) pH 8.0 buffer at varying glucose concentrations.

The emission spectra of o-BMOQBA when both the pH media and glucose concentrations are varied are shown in FIG. 15, wherein FIGS. 15A, 15B, 15C and 15D correspond to pH 5, 6, 7, and 8 buffers, respectively. As discussed with reference to o-BMQBA, decreasing intensity with increasing pH is attributed to the "charge neutralization-stabilization mechanism." With stabilization, e.g., binding of glucose to the boronic acid moiety, there is a quantifiable reduction in the fluorescence intensity.

Figure 16:
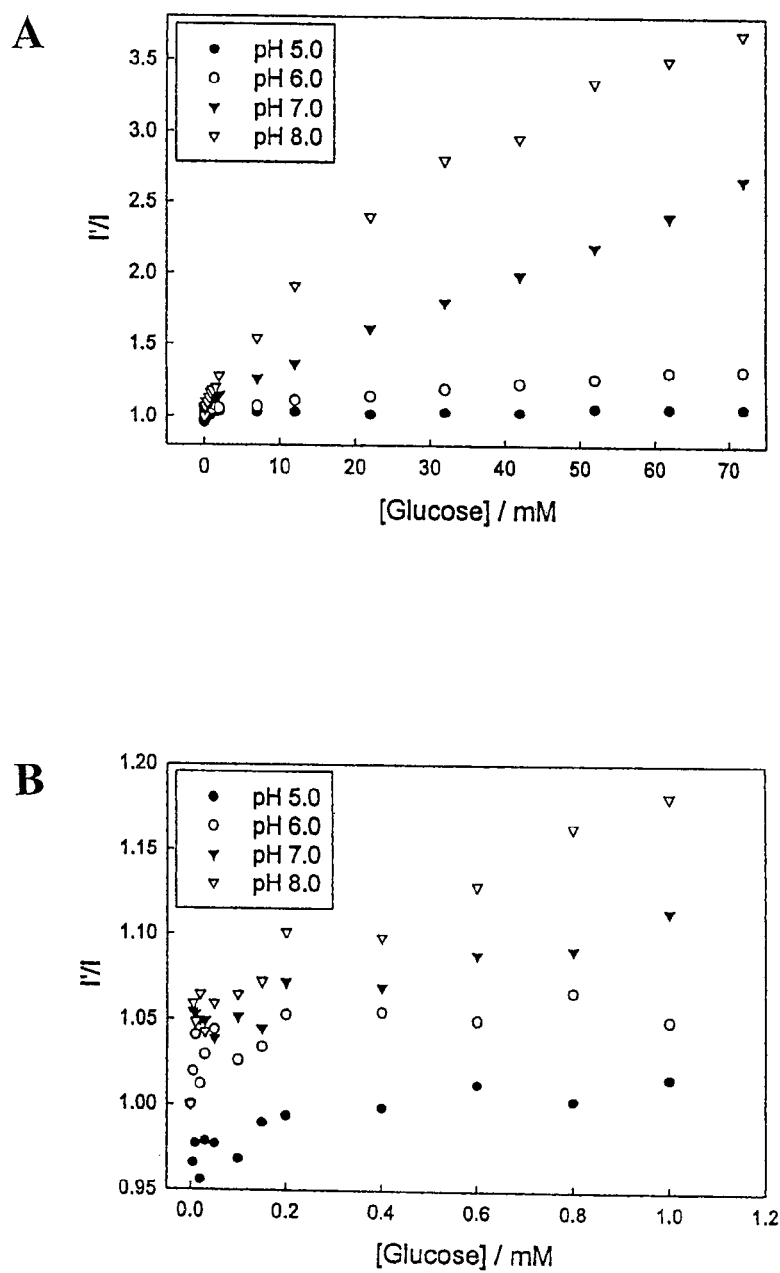
FIG. 16 shows the intensity ratio at $\lambda$=450 nm ($\lambda_{ex}$=345 nm) for o-BMOQBA at varying buffered pH values and glucose concentrations at (A) high glucose concentrations and (B) low glucose concentrations (typical of those found in tears).
Figure 17:
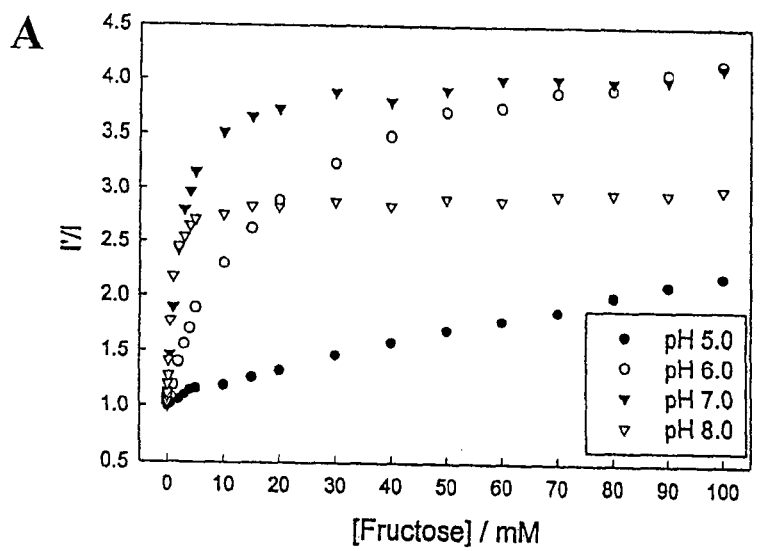
FIG. 17 shows the intensity ratio at $\lambda$=450 nm ($\lambda_{ex}$=345 nm) for o-BMOQBA at varying buffered pH values and fructose concentrations at (A) high fructose concentrations and (B) low fructose concentrations.
Figure 17:
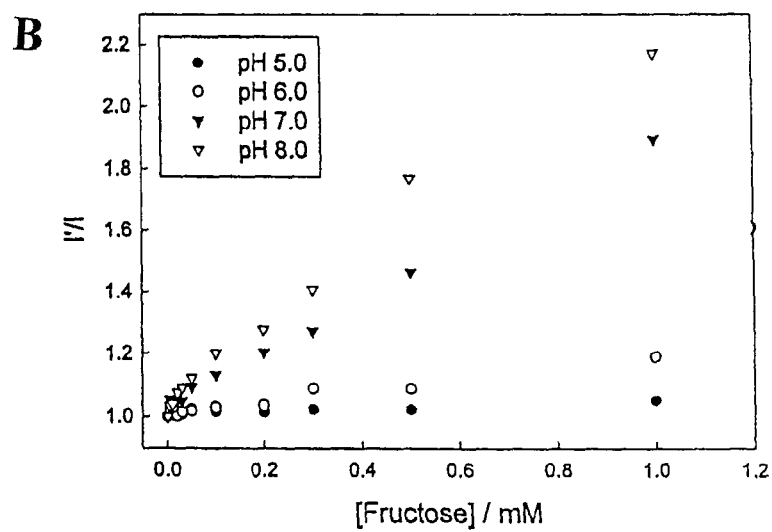

The intensity ratio at λ=450 nm for o-BMOQBA in buffered media (pH 5-8) at various glucose concentrations is shown in FIG. 16A, wherein I' corresponds to the intensity in the absence of glucose and I corresponds to the intensity at the specified glucose concentration. In addition, the intensity ratio for o-BMOQBA in buffered media (pH 5-8) at low glucose concentrations, typical of those found in tears, is shown in FIG. 16B. Correspondingly, the intensity ratio for o-BMOQBA in buffered media (pH 5-8) at various fructose concentrations is shown in FIGS. 17A and 17B.

It can be seen that for 60 mM glucose, in the pH 6 to 7 range, there is a 1.3→2.5 fold decrease in fluorescence intensity (see FIG. 16A) and about a 5-10% decrease in fluorescence intensity at 0.60 mM glucose (see FIG. 16B). In a corresponding manner, for fructose in the pH 6 to 7 range, there is a 2.7→3.7 fold decrease in fluorescence intensity at 60 mM fructose and a 10-40% decrease in intensity at 0.50 mM fructose. These are measurable differences that allow for the quantification of monosaccharide concentrations.

Figure 18:
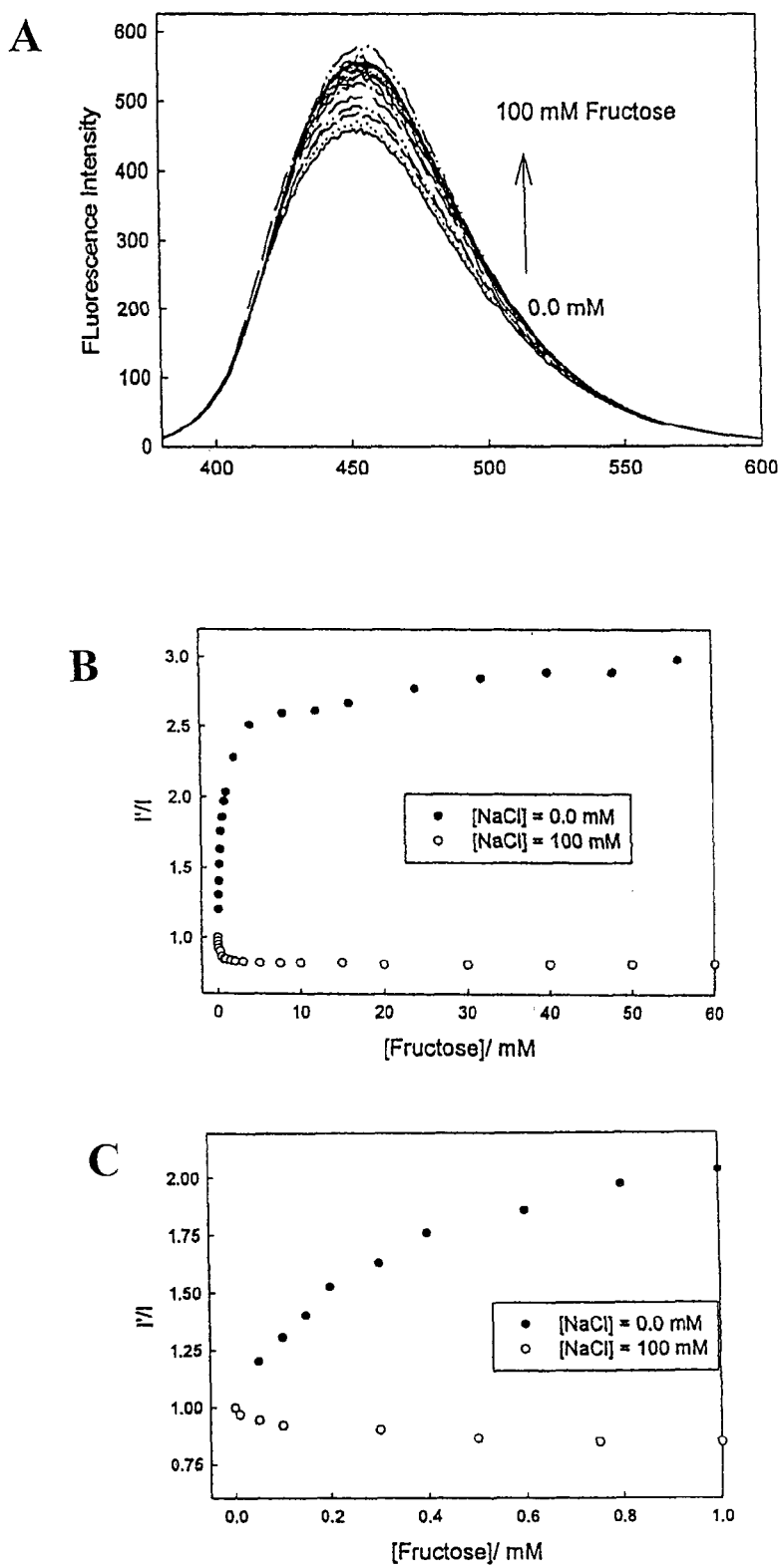
FIG. 18A shows the emission spectra ($\lambda_{ex}$=345 nm) of o-BMOQBA in pH 7.5 phosphate buffer having 100 mM NaCl at various fructose concentrations.
FIG. 18B shows the intensity ratio at $\lambda$=450 nm ($\lambda_{ex}$=345 nm) for o-BMOQBA at specified fructose concentrations in the absence and presence of NaCl, where I' is the fluorescence intensity at 0 mM fructose and I is the corresponding intensity at the specified fructose concentration.
FIG. 18C shows the intensity ratio at $\lambda$=450 nm ($\lambda_{ex}$=345 nm) for o-BMOQBA at low fructose concentrations in the absence and presence of NaCl, where I' is the fluorescence intensity at 0 mM fructose and I is the corresponding intensity at the specified fructose concentration.
Figure 19:
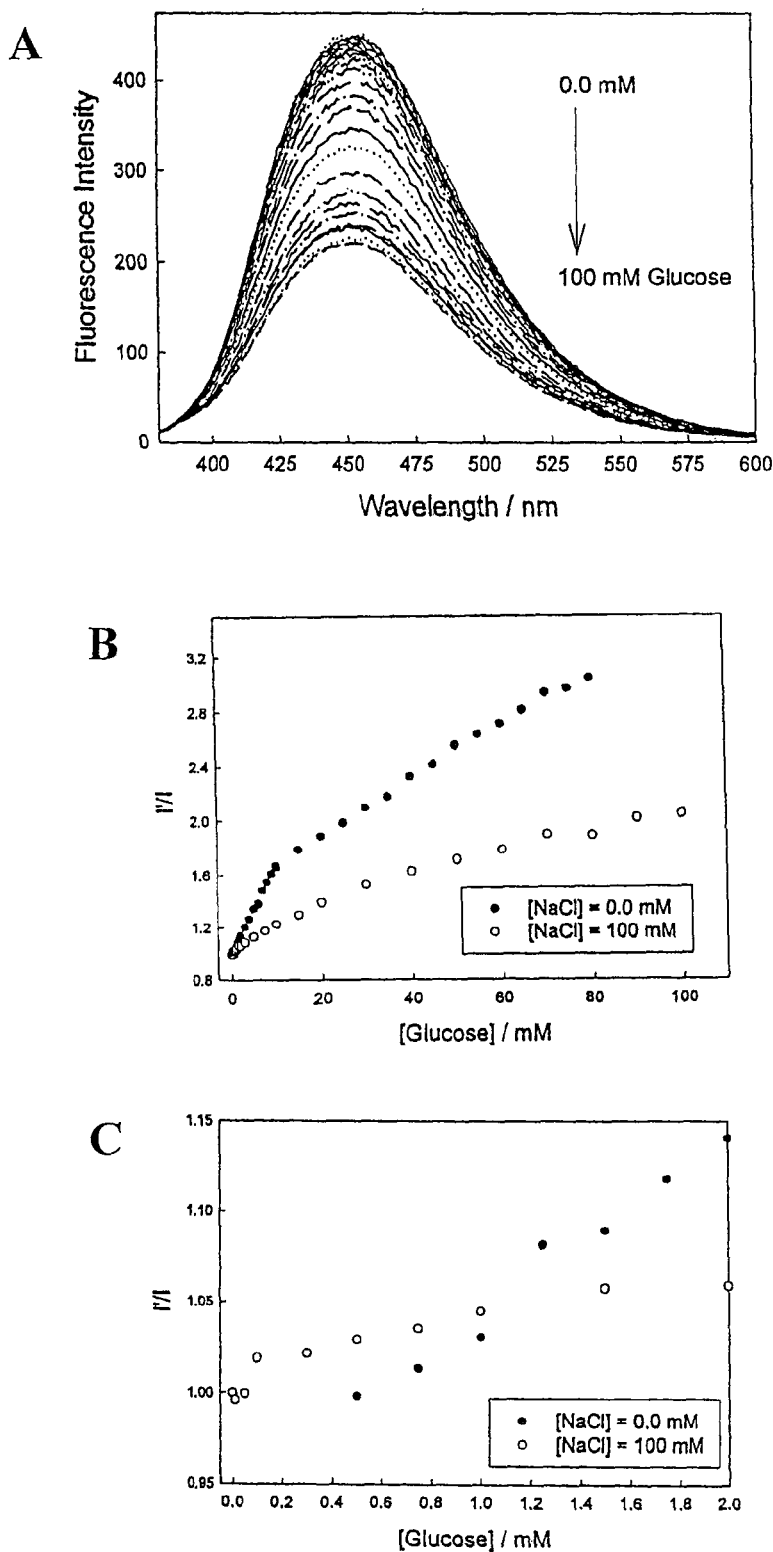
FIG. 19A shows the emission spectra ($\lambda_{ex}$=345 nm) of o-BMOQBA in pH 7.5 phosphate buffer having 100 mM NaCl at various glucose concentrations.
FIG. 19B shows the intensity ratio at $\lambda$=450 nm ($\lambda_{ex}$=345 nm) for o-BMOQBA at specified glucose concentrations in the absence and presence of NaCl, where I' is the fluorescence intensity at 0 mM glucose and I is the corresponding intensity at the specified glucose concentration.
FIG. 19C shows the intensity ratio at $\lambda$=450 nm ($\lambda_{ex}$=345 nm) for o-BMOQBA at low glucose concentrations in the absence and presence of NaCl, where I' is the fluorescence intensity at 0 mM glucose and I is the corresponding intensity at the specified glucose concentration.

As presented with reference to o-BMQBA, the quenching of the fluorescence intensity of o-BMOQBA by chloride was tested. The fluorescence intensity and intensity ratios of o-BMOQBA in pH 7.5 buffer having 100 mM NaCl with fructose and glucose was measured and shown in FIGS. 18 and 19, respectively, where I' corresponds to the intensity in the absence of fructose and I corresponds to the intensity at the specified fructose concentration. With regards to glucose, the presence of chloride quenched the intensity of the emission, as expected (Jayaraman, S., et al., *Biophys. Chem.*, 85, 49-57 (2000)). The calculated Stern-Volmer constants, $K_{SV}$, for the BMOQBA compounds in water were determined to be 170 $M^{-1}$, 182 $M^{-1}$, 177 $M^{-1}$ and 222 $M^{-1}$ for o-BMOQBA, m-BMOQBA, p-BMOQBA and BMOQ, respectively, which is indicative of modest quenching of the BMOQBA molecules by the chloride ion.

Importantly, monosaccharide levels are still determinable over the high background chloride levels present in the blood and other physiological fluids. Moreover, the control compounds, e.g., BMQ and BMOQ, which do not bind monosaccharides because of the lack of a boronic acid moiety, are equally sensitive to chloride ions. As such, it is envisioned that an alternative embodiment of this invention utilizes both the novel phenyl boronic acid probes and the novel control compounds, to monitor monosaccharide and chloride levels, respectively, simultaneously.

Figure 20:
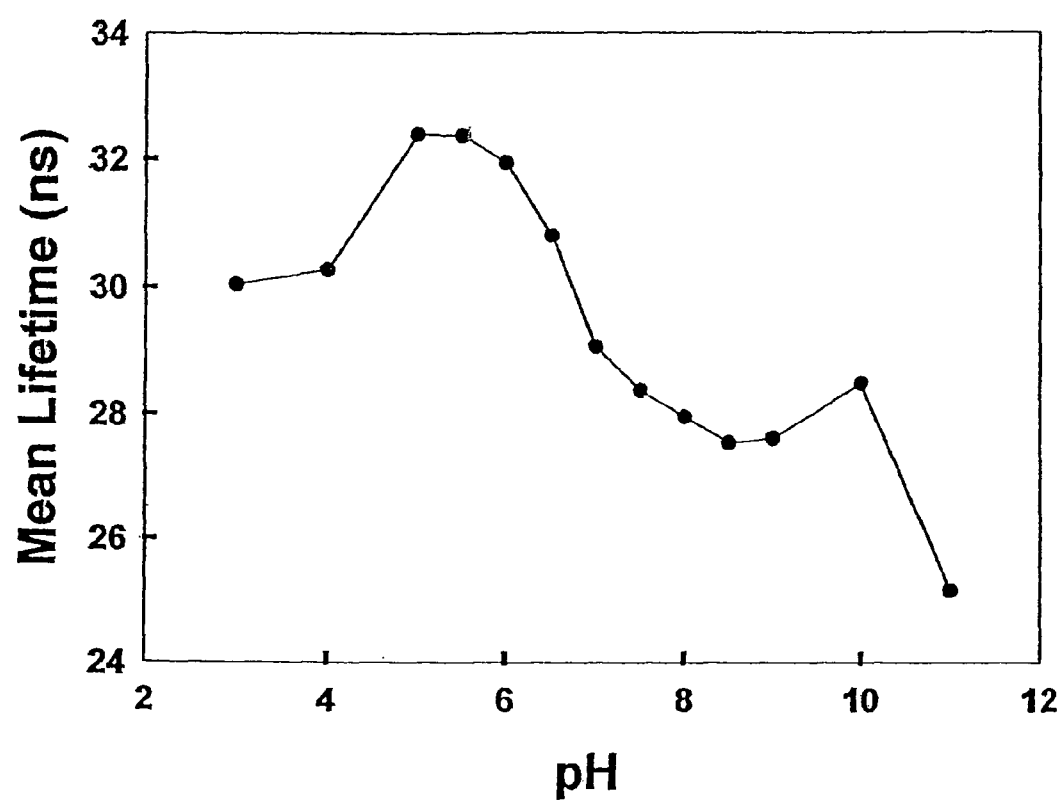
FIG. 20 shows the mean lifetime of o-BMOQBA at different buffered pH values.

Notably, the BMOQBA molecular sensing moieties were found to have monoexponential lifetimes (~24.9 ns→26.7 ns), as compared to the BMQBA molecular sensing moieties which were biexponential in water (2.10 ns→4.01 ns). Notably, the lifetimes of BMOQ and BMQ are 27.3 ns and 2.59 ns, respectively. These lifetimes directly correlate with the quantum yields for the respective novel compounds. As previously discussed with regards to the lower quantum yield, the lower lifetime of the BMQBA molecular sensing moiety may be attributed to a photo-induced electron transfer mechanism, wherein the phenyl ring of the BMQBA acts as an electron donor and the quaternary nitrogen heterocyclic center as an electron acceptor. In addition, the $B(OH)_3^-$ (represented by B in FIG. 1) present at or above neutral pH further reduces the lifetime of the boronic acid molecular sensing moieties (see FIG. 20, where the lifetime of o-BMOQBA decreases with increasing pH).

5. Absorption and Emission Studies of Contact Lenses Containing BMQBA in the Absence and Presence of Monosaccharides The ophthalmic sensor device of the invention comprises a contact lens made from any known suitable lens-forming materials. For example, a lens-forming material can be a prepolymer, a mixture of prepolymers, a mixture of monomers, or a mixture of one or more prepolymers and one or more monomers and/or macromers. A lens-forming material can further include other components, such as a photoinitiator, a visibility tinting agent, UV-blocking agent, photosensitizers, and the like. It should be understood that any silicone-containing prepolymers or any silicone-free prepolymers can be used in the present invention.

A contact lens of the invention can be used for non-invasive monitoring of glucose levels in tears. Glucose levels in tears can be converted into blood glucose levels based on correlations between tear glucose levels and blood glucose levels (Süllmann, *Handbuch der Physiologischen Chemie*, Vol. II/a, p. 867, Springer, Berlin, 1956; Graymore, *The Eye*, Vol. I, p. 348, Davson, ed., Academic Press, NY, 1962; De Berardinis et al, *Exp. Eye Res.*, 4, 179 (1965); Pohjola, *Acta Ophthalmologica Suppl.*, 88, (1966); Reim et al., *Ophthalmologica*, 154, 39-50 (1967); Kinsey & Reddy, in Prince, ed., *The Rabbit and Eye Research*, C. C. Thomas, Springfield, Ill., 1964, p. 218).

The ophthalmic sensor device of the present invention can be an implantable ophthalmic device. Moreover, because the glucose levels in tears may be substantially lower than blood glucose levels, using an implantable sensor device, one can monitor periodically or on demand glucose levels in aqueous humor or interstitial fluid where glucose levels can be much higher than the glucose levels in tears.

In the present case, daily-disposable contact lenses were used, supplied by CIBA Vision (Atlanta, Ga., USA), which were stirred in 500 mL water at 20° C. for 24 hours before post-doping. The contact lenses were a PVA type photo cured polymer which swells slightly in water. The hydrophilic character of the lens allows for the diffusion of the aqueous analytes in tears. The lenses were subsequently doped by incubating the lenses in a high concentration of a phenyl boronic acid derivative, e.g., BMQBA, solution for 24 hours before being rinsed with Millipore water. The lenses were used immediately after being doped.

The absorption and emission of the phenyl boronic acid derivative from the contact lens were measured using a quartz lens holder. The quartz lens holder has the dimensions 4×2.5× 0.8 cm, all four sides being of optical quality. The contact lens were mounted onto a stainless steel mount of dimensions 4×2×0.4 cm, which fits tightly into the quartz lens holder. A circular hole in the center of the mount with a 2.5 cm inner diameter, has a raised quartz lip which enables the lens to be mounted thereon. The mount and holder readily allow for ~1.5 cm$^3$ of solution to be in contact with the front and back sides of the lens for the sugar sensing experiments. Excitation and emission were measured using a Varian fluorometer with the concave edge of the lens facing towards the excitation source, to reduce scattering of the excitation light. It is noted that measurements performed when the convex edge of the lens faces the excitation source yielded identical results.

Fluorophore leaching experiments were performed at 20° C. using the lens holder, which contains approximately 1.5 cm$^3$ buffer. A Varian fluorometer was used to measure the intensity change as a function of time to determine the percent signal change that corresponds to leaching. It is noted that in the absence of a sample, no intensity fluctuations or drifts were observed, indicating stability of the fluorometer Xe-arc source.

Figure 21:
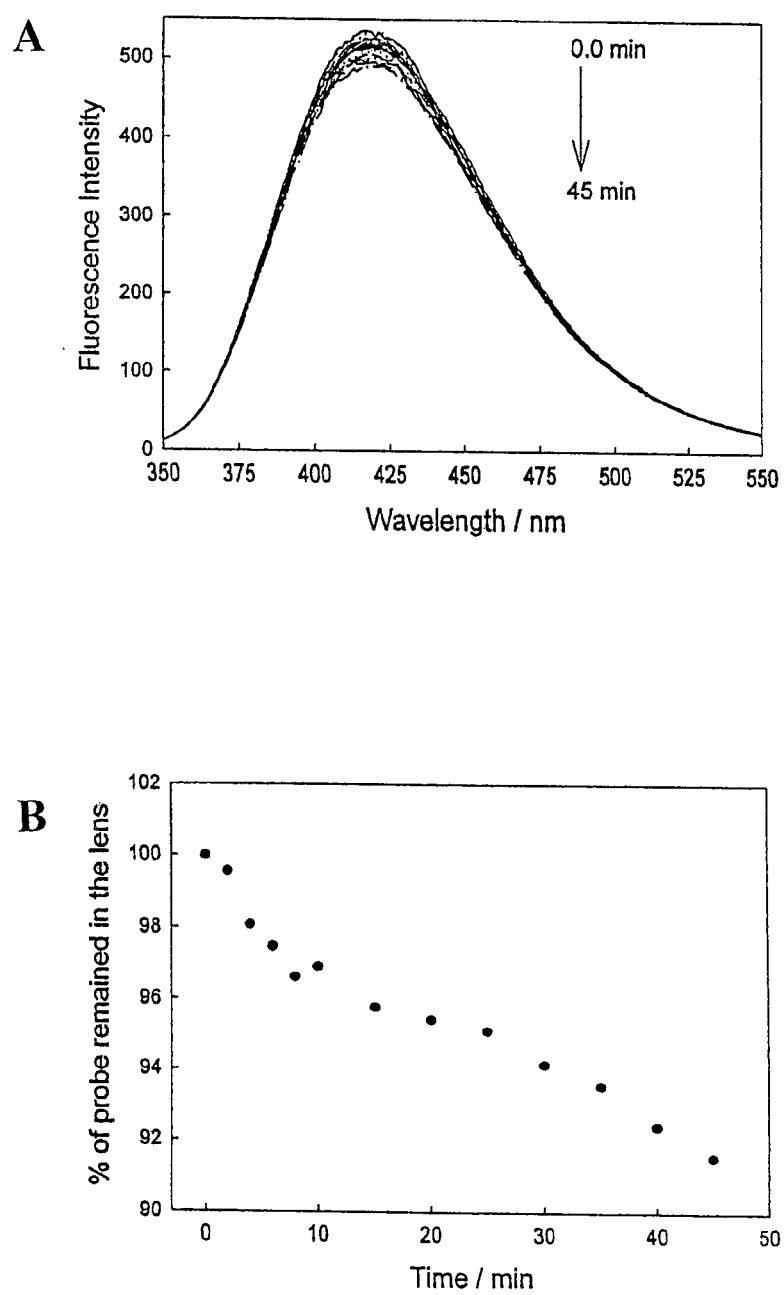
FIG. 21 shows (A) the emission spectra of o-BMQBA leaching from a BMQBA-doped contact lens into a pH 7.5 buffer with time, (B) percent of o-BMQBA remaining in the BMQBA-doped contact lens over time.

FIG. 21A shows the leaching of o-BMQBA from a BMQBA-doped contact lens into pH 7.5 buffer with time. It is noted that due to the very low concentration of fluorophores sensing compounds within the lenses, the amount of unleached fluorophores sensing compounds could not be readily determined. As such, the percent loss of fluorescence intensity from the lens as a function of time was determined (see FIG. 21B). This was performed simply to provide an indication of how long the lenses should be leached before use. Based on FIG. 21B, the lenses were allowed to leach excess molecular sensing compound for 60 minutes before absorption and emission measurements or the addition of sugars to the solutions.

Following leaching, buffered solutions of sugars were added to the lens holder. Because the 90% response time, which is the amount of time needed for the fluorescence signal to change by 90% of the initial value, was approximately 10 minutes, fluorescence spectra were typically taken approximately 15 minutes after each sugar addition to allow the lens to reach equilibrium.

It is noted that the shelf-life of the doped contact lens was tested, and it was determined that lenses that had been doped, leached and stored for several months, both wet and dry, gave identical sugar sensing results, indicating no fluorophore-polymer interactions or fluorophore degradation over this time period.

Figure 22:
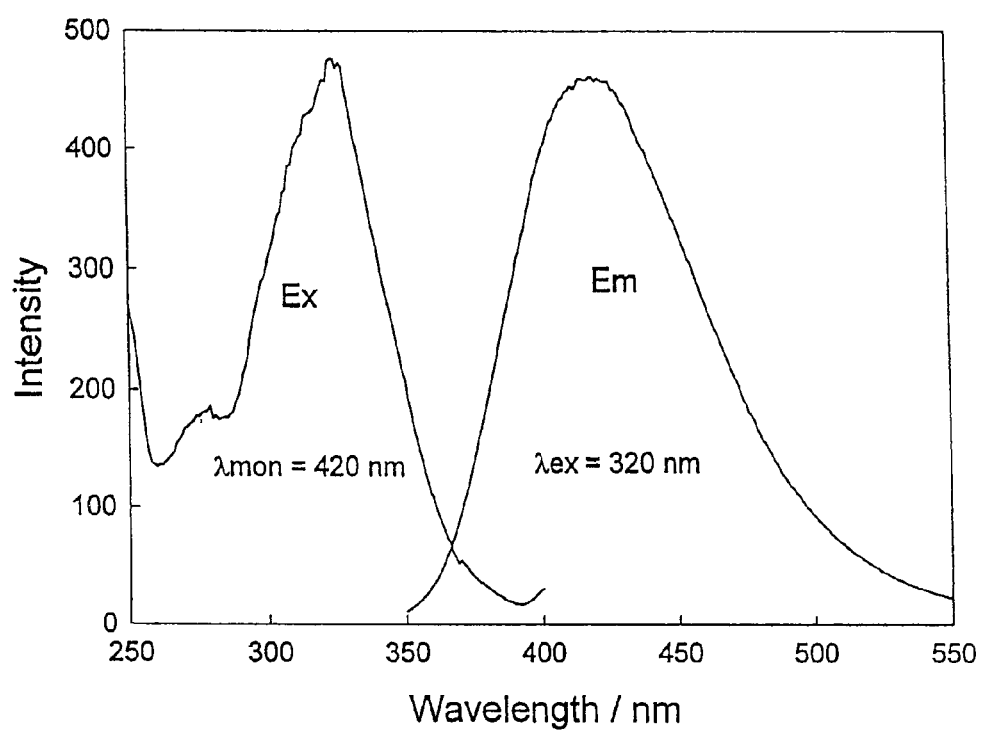
FIG. 22 shows the absorption and emission spectra of a o-BMQBA-doped contact lens in a pH 7.5 buffer.

A representative absorption and emission spectra for a o-BMQBA-doped contact lens in pH 7.5 buffer is shown in FIG. 22, which corresponds to all three isomers and BMQ. BMQBA has a strong absorption band at ~320 nm and an excitation band at ~420 nm, therefore having a large Stokes shift of about 100 nm.

Figure 23:
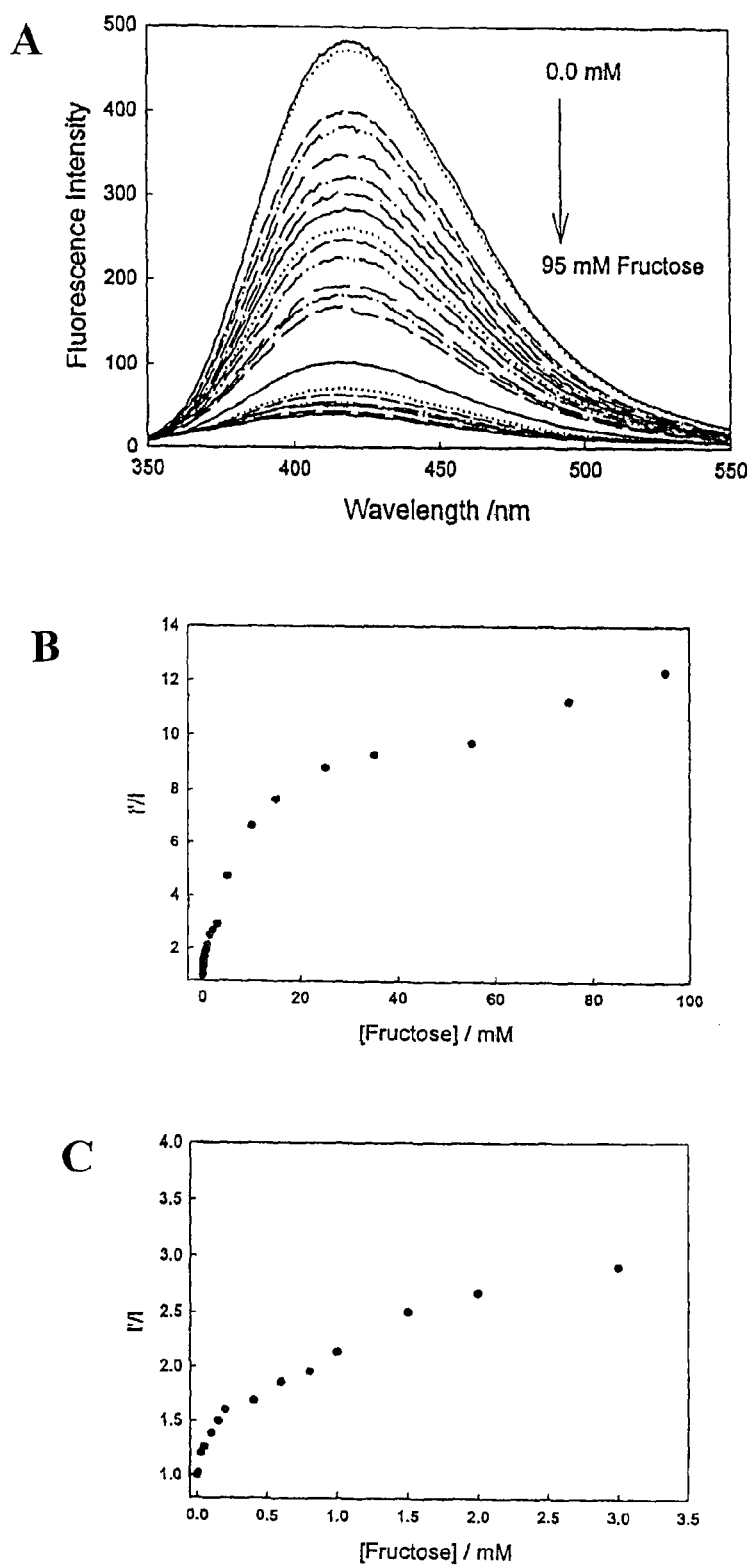
FIG. 23A shows the emission spectra of a o-BMQBA-doped contact lens in pH 7.5 phosphate buffer with increasing concentrations of fructose.
FIG. 23B shows the intensity ratio of a o-BMQBA-doped contact lens in pH 7.5 buffer at $\lambda$=420 nm in the absence, I', and presence, I, of fructose.
FIG. 23C shows the intensity ratio of a o-BMQBA-doped contact lens in pH 7.5 buffer at $\lambda$=420 nm at low fructose concentrations in the absence, I', and presence, I, of the fructose, respectively.
Figure 24:
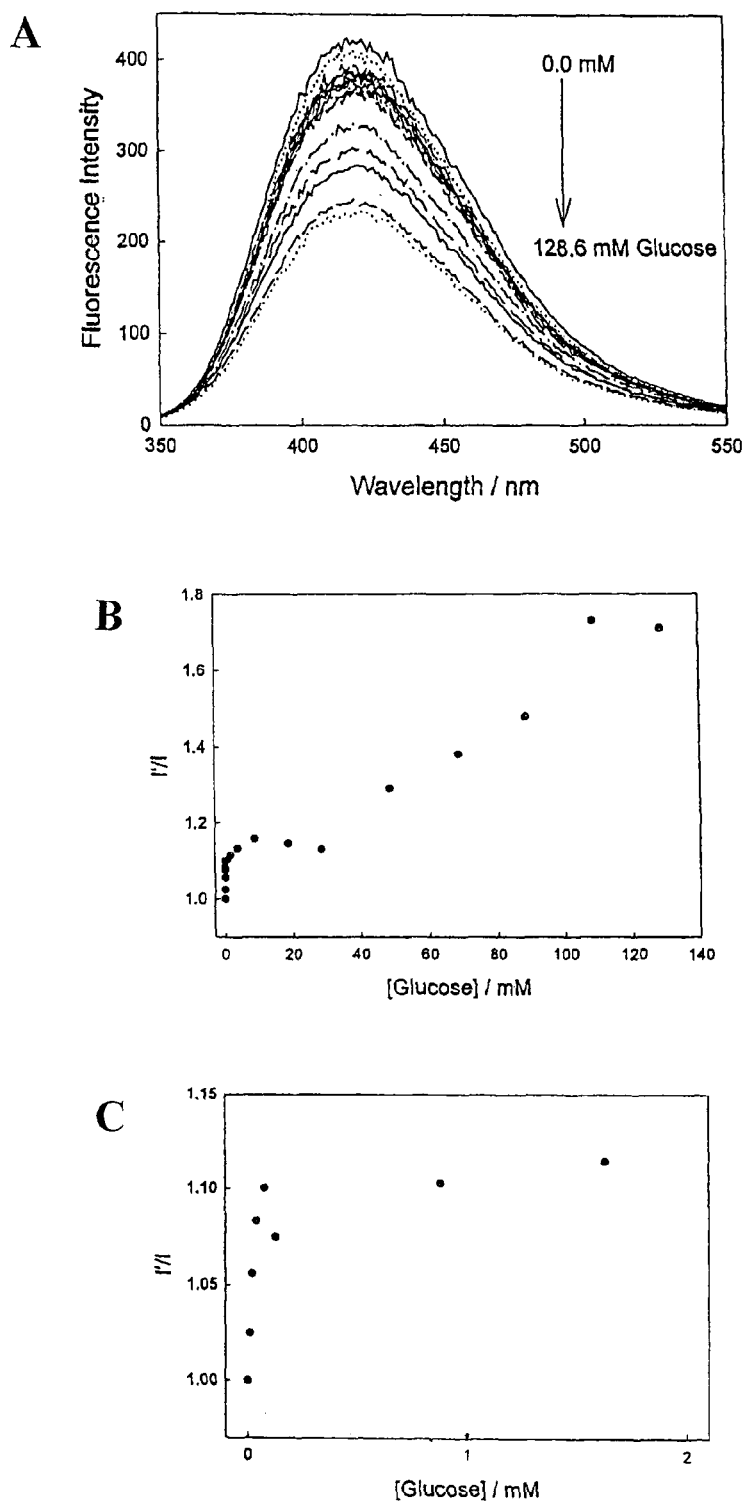
FIG. 24A shows the emission spectra of a o-BMQBA-doped contact lens in pH 7.5 phosphate buffer with increasing concentrations of glucose.
FIG. 24B shows the intensity ratio of a o-BMQBA-doped contact lens in pH 7.5 buffer at $\lambda$=420 nm in the absence, I', and presence, I, of the glucose, respectively.
FIG. 24C shows the intensity ratio of a o-BMQBA-doped contact lens in pH 7.5 buffer at $\lambda$=420 nm at low glucose concentrations in the absence, I', and presence, I, of the glucose, respectively.

FIGS. 23A and 24A show the fluorescence intensity of o-BMQBA-doped contact lenses with increasing concentrations of fructose and glucose, respectively, when the respective monosaccharides are injected into the 1.5 cm$^3$ contact lens volume. Similar to the solution based measurements (see FIGS. 4A and 4B), the molecular sensing moieties show a decrease in fluorescence intensity with increasing fructose and glucose concentration, which was attributed to the complexation of diols with boronic acid and subsequent charge neutralization. Intensity ratio plots, where I' is the intensity in the absence of fructose and I is the intensity at the specified fructose or glucose concentration, are shown in FIG. 23B, 23C or 24B, 24C, respectively. As was observed with the solution measurements, phenyl boronic acid derivatives seem to have a greater affinity for fructose, which is based on the greater response of fructose. Notably, however, when the concentration of sugar is <2 mM, the response to both sugars was comparable (Badugu, R., et al., *J. Fluorescence*, 13, 371-374 (2003)).

Importantly, the doped contact lens is reversibly responsive to the aqueous monosaccharides at physiological tear concentrations, thus allowing the continuous monitoring of tear analytes.

Figure 25:
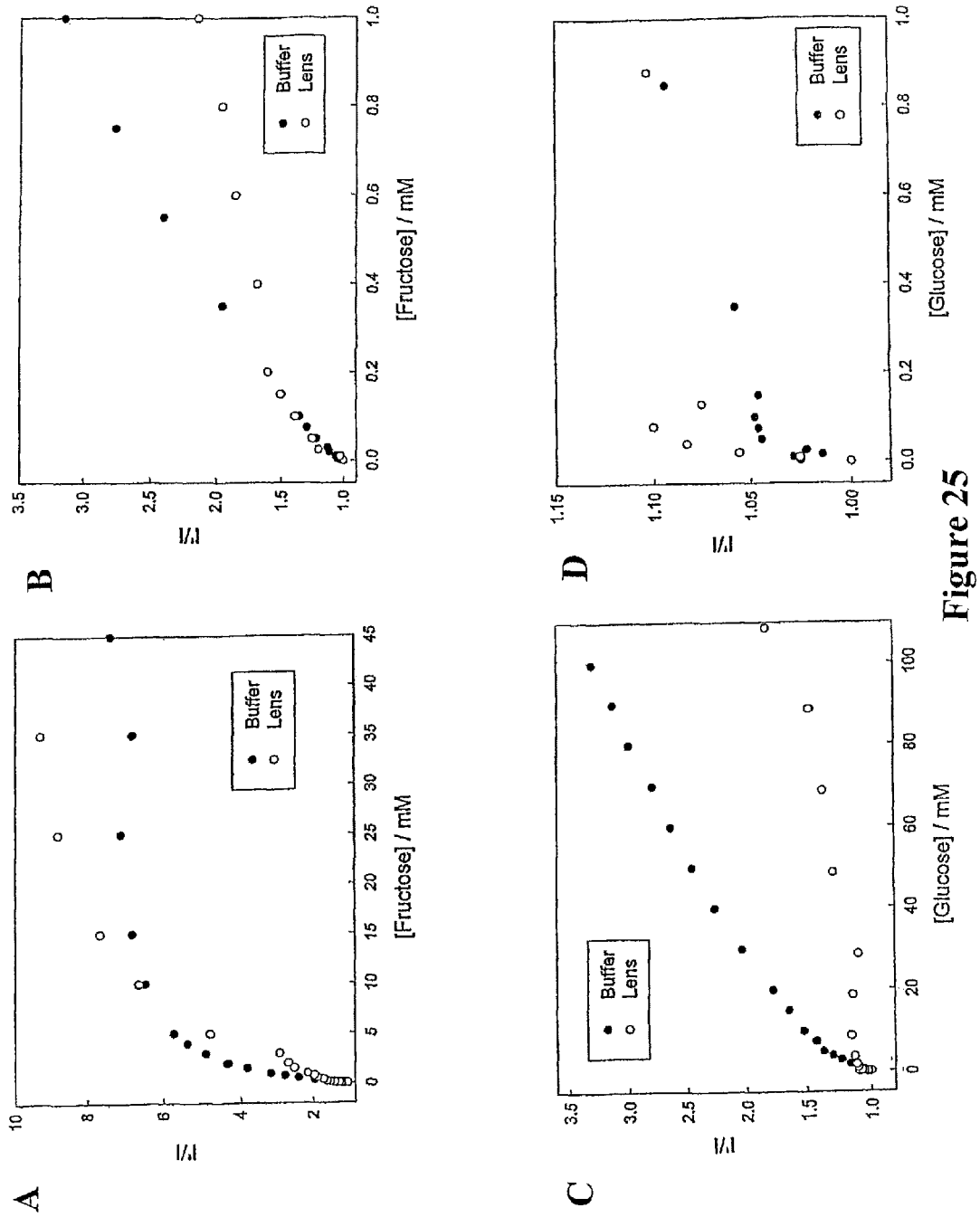
FIG. 25 shows the comparison of the intensity ratios of a o-BMQBA-doped contact lens in pH 7.5 buffer at $\lambda$=420 nm to the solution-based measurements in pH 7.5 buffer at $\lambda$=427 nm for (A) high concentrations of fructose, (B) low concentrations of fructose, (C) high concentrations of glucose, and (D) low concentrations of glucose.

FIG. 25 shows the differences in response of the o-BMQBA-doped contact lenses towards the sugars relative to the solution-based studies. Interestingly, the response in the lens was greater than in the solutions when fructose was added to the lens holder (see FIGS. 25A and 25B), while just the opposite was observed for high concentrations of glucose (FIGS. 25C and 25D). It is speculated that this may be due to greater leaching of the glucose-bound form of the phenyl boronic acid compounds from the contact lens and/or their displaced solubility within the contact lens polymer. Importantly, at low concentrations of glucose, the response in the lens was nearly equivalent to that previously observed with the solution-based studies, amounting to a 5-10% change in intensity at 0.50 mM glucose.

Most boronic acid probes suffer from too low a binding constant to be able to detect and determine tear glucose concentrations, thus making them useless for sensing applications. However, the novel fluorophores disclosed herein have higher binding constants and as such, are able to determine tear glucose concentrations and are unperturbed at low concentrations by the contact lens matrix.

It is noted that it is difficult to assess the effect of the PVA hydroxyl groups of the contact lens polymer on the boronic acid:sugar complexation reaction. However, studies performed with solutions of glycerol indicated that monosaccharides have a greater binding affinity for the novel phenyl boronic acid compounds than glycerol hydroxyl groups. As such, we speculate that the sugars will preferentially bind the boronic acid groups of the BMQBA-doped contact lens.

It is also informative to consider the pH of tears as a potential interferent, given the response of these fluorophores to pH as shown in FIGS. 6 and 14. Unstimulated tear pH levels can vary in the range 7.14-7.82 measured from healthy subjects at different times of the day, with a typical mean value around pH 7.45. However, a more acidic pH of less than 7.3 is found following prolonged lid closure, e.g., after sleep, which is thought to result from carbon dioxide produced by the cornea and trapped in the tear pool under the eyelids. While solutions of these new fluorophores would be susceptible to these changes in pH, we have found that the doped lenses were unbufferable, hence external changes in pH are unlikely to affect the response to analytes.

Figure 26:
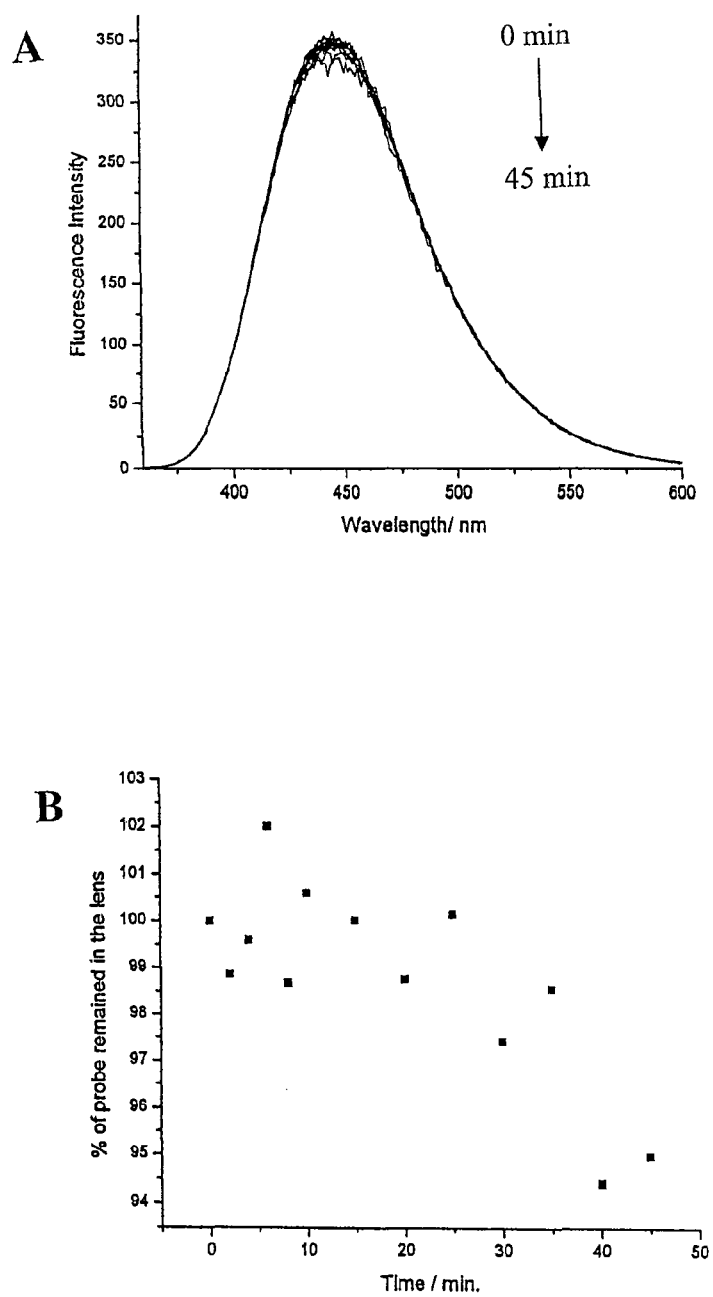
FIG. 26 shows (A) the emission spectra of o-BMOQBA leaching from a BMOQBA-doped contact lens into a pH 7.5 buffer with time, (B) percent of o-BMOQBA remaining in the BMOQBA-doped contact lens over time.

6. Absorption and Emission Studies of Contact Lenses Containing BMOQBA in the Absence and Presence of Monosaccharides FIG. 26 shows the leaching of o-BMOQBA from a BMOQBA-doped contact lens into pH 7.5 buffer with time (see FIG. 26A), and the percent loss of fluorescence intensity from the lens as a function of time (see FIG. 26B). As discussed with reference to BMQBA, this experiment was performed simply to provide an indication of how long the lenses should be leached before use. Based on FIG. 26B, the lenses were allowed to leach excess molecular sensing compound for 60 minutes before absorption and emission measurements or the addition of sugars to the solutions.

Following leaching, buffered solutions of sugars are added to the lens holder. Because the 90% response time, which is the amount of time needed for the fluorescence signal to change by 90% of the initial value, was approximately 10 minutes, fluorescence spectra were typically taken approximately 15 minutes after each sugar addition to allow the lens to reach equilibrium.

Figure 27:
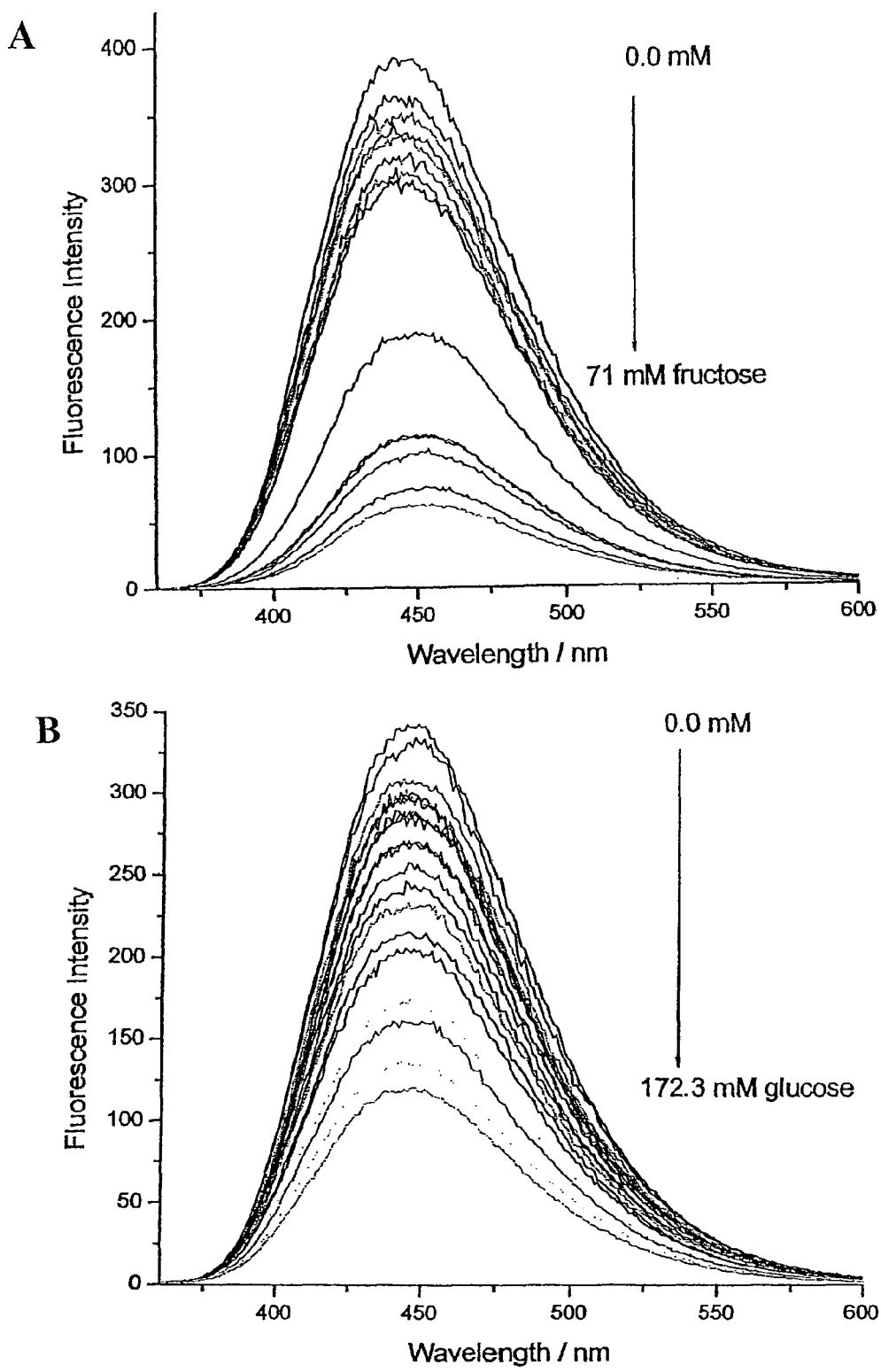
FIG. 27A shows the emission spectra of a o-BMOQBA-doped contact lens in pH 7.5 phosphate buffer with increasing concentrations of fructose.
FIG. 27B shows the emission spectra of a o-BMOQBA-doped contact lens in pH 7.5 phosphate buffer with increasing concentrations of glucose.
Figure 28:
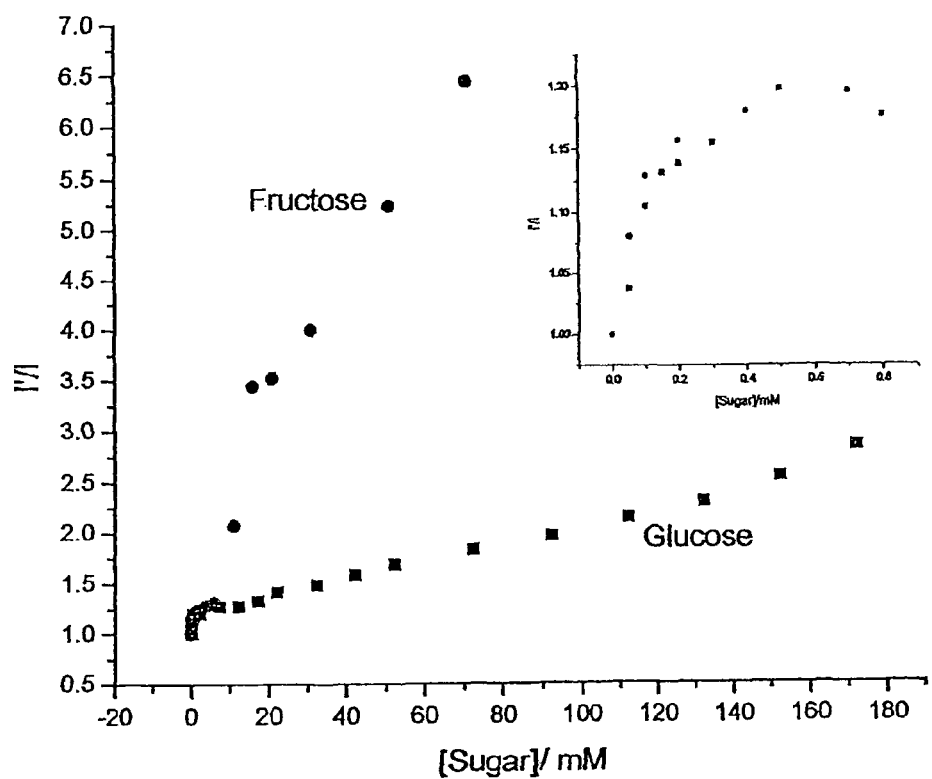
FIG. 28 shows the intensity ratio of a o-BMOQBA-doped contact lens in pH 7.5 buffer at $\lambda$=420 nm in the absence, I', and presence, I, of fructose (●) or glucose (■).

FIGS. 27A and 27B show the fluorescence intensity of a o-BMOQBA-doped contact lenses with increasing concentrations of fructose and glucose, respectively, when the respective monosaccharides are injected into the 1.5 cm$^3$ contact lens volume. Similar to the solution based measurements (see FIGS. 12A and 12B), the molecular sensing moieties show a decrease in fluorescence intensity with increasing fructose and glucose concentration, which we attribute to the complexation of diols with boronic acid and subsequent charge neutralization. An intensity ratio plot, where I' is the intensity in the absence of monosaccharide and I is the intensity at the specified fructose (●) or glucose (■) concentration, is shown in FIG. 28. As was observed with the solution measurements, phenyl boronic acid derivatives seem to have a greater affinity for fructose, which is based on the greater response of fructose. However, referring to the insert of FIG. 28, when the concentration of sugar is <1 mM, the response to both sugars was identical (Badugu, R., et al., *J. Fluorescence*, 13, 371-374 (2003)), with a 20% change in fluorescence signal with the addition of only 0.50 mM sugar.

Figure 29:
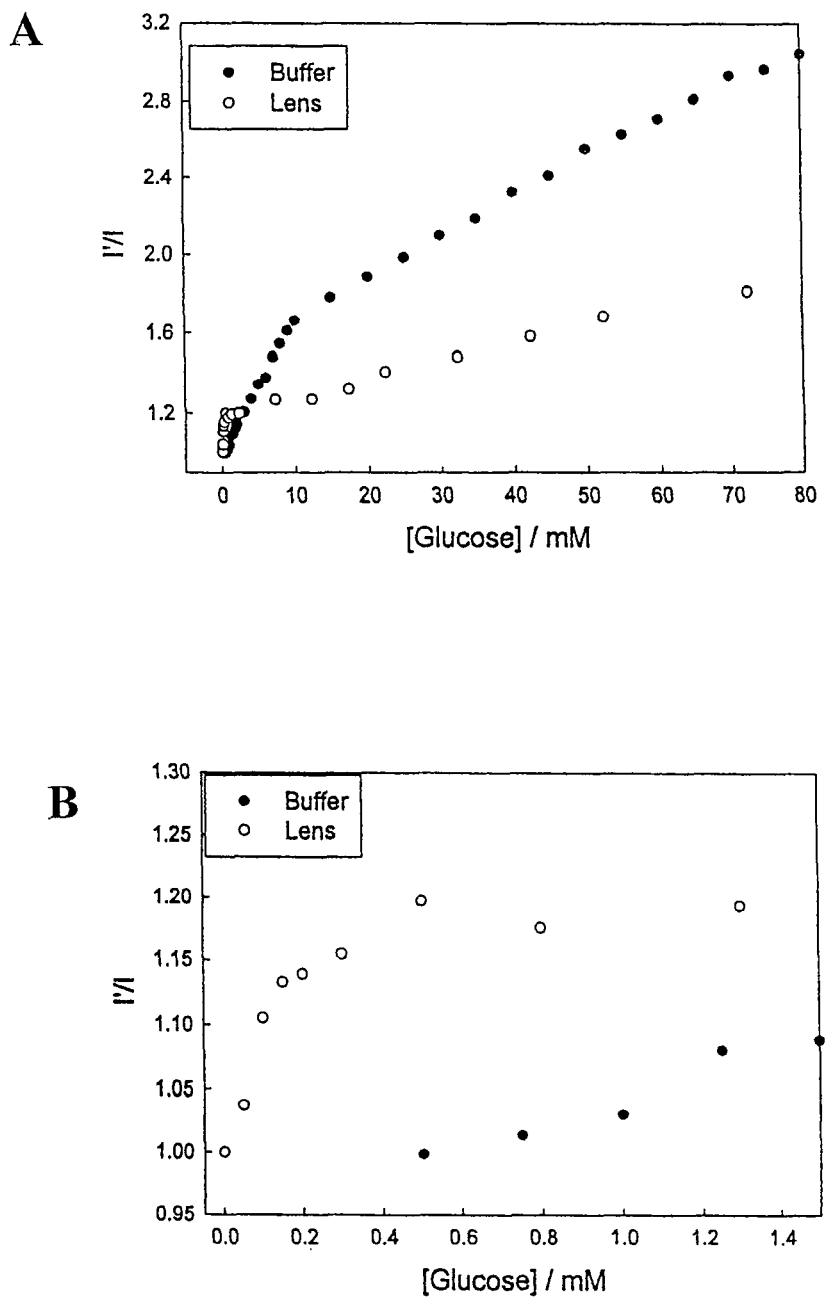
FIG. 29 shows the comparison of the intensity ratios of a o-BMOQBA-doped contact lens in pH 7.5 buffer at $\lambda$=420 nm to the solution-based measurements in pH 7.5 buffer at $\lambda$=427 nm for (A) high concentrations of glucose, and (B) low concentrations of glucose.

FIG. 29 shows the differences in response of the o-BMOQBA-doped contact lenses towards glucose relative to the solution-based studies (both buffered at pH 7.5). Importantly, the response in the lens was greater than in the solutions at the lower concentrations of glucose (see FIG. 29B), which correspond to those concentrations normally observed in tears. It is unknown at this time why at higher concentrations of glucose, the response shifts, whereby the greater response is observed in the solution-based studies. However, this shift is advantageous because the higher concentrations of glucose, such as those observed in blood, can be readily monitored using a solution-based measurement.

Figure 30:
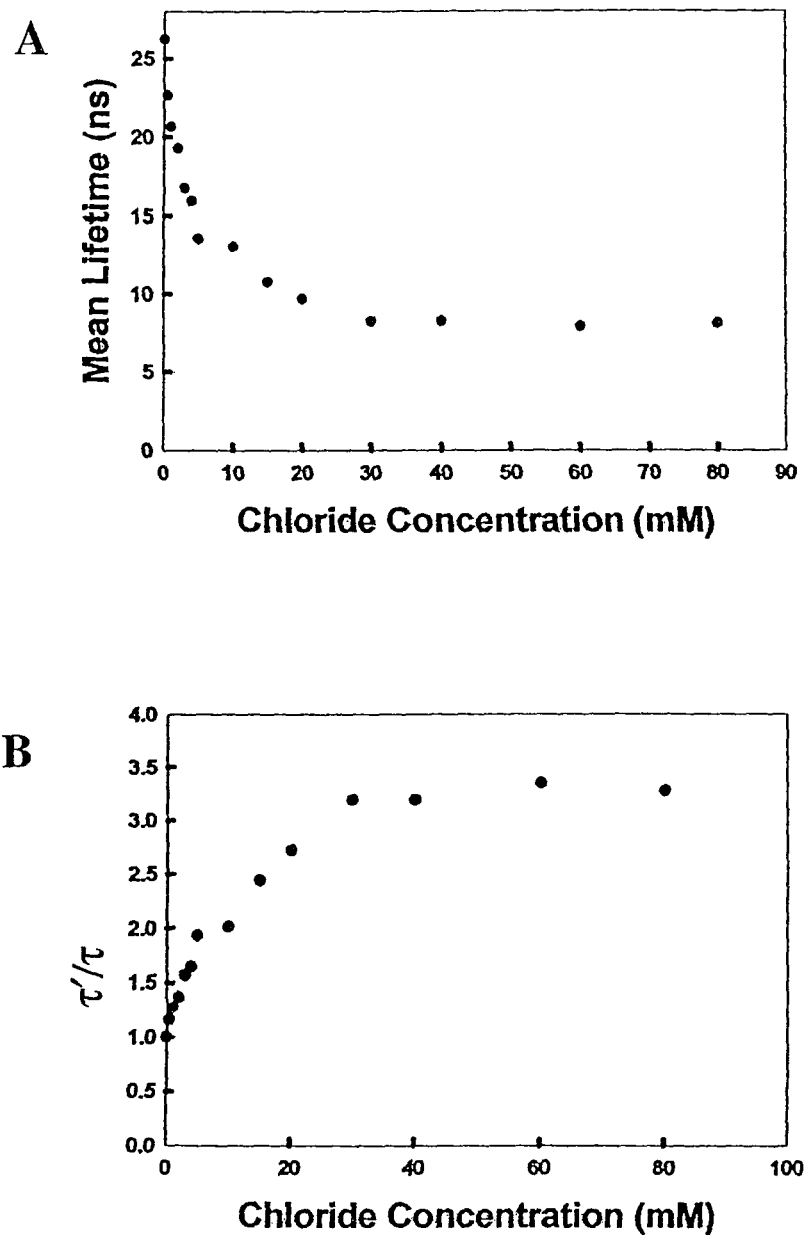
FIG. 30A shows the mean lifetime of the o-BMOQBA-doped contact lens with varying chloride concentrations.
FIG. 30B shows the lifetime ratio of the o-BMOQBA-doped contact lens with varying chloride concentrations, where $\tau'$ represents the lifetime at 0 mM chloride and $\tau$ represents the lifetime at the specified chloride concentration.

FIG. 30 shows the response of the halide sensitive o-BMOQBA fluorophore contained within the contact lens to chloride ions, demonstrating the sensing capability of the fluorophore-doped contact lens to chloride, and hence bromide and iodide ions. Notably, the control compounds, e.g., BMQ and BMOQ, which do not bind monosaccharides because of the lack of a boronic acid moiety, are equally sensitive to chloride ions. As such, it is envisioned that another alternative embodiment of this invention utilizes both the novel phenyl boronic acid probes and the novel control compounds, e.g., by immobilizing one of each of the novel compounds in its own contact lens, to monitor monosaccharide and chloride levels simultaneously. Alternatively, both compounds may be immobilized in the same lens, and the spectral responses are simply resolved by the use of different excitation and emission wavelengths.

Monosaccharide lifetime sensing or ratiometric monosaccharide sensing are envisioned as embodiments employed to determine monosaccharide concentrations using the novel phenyl boronic acid-doped contact lenses.

A further embodiment of this technology is the use of colored contact lenses which change color upon changes to the tear, and hence blood, glucose concentration.

Figure 31:
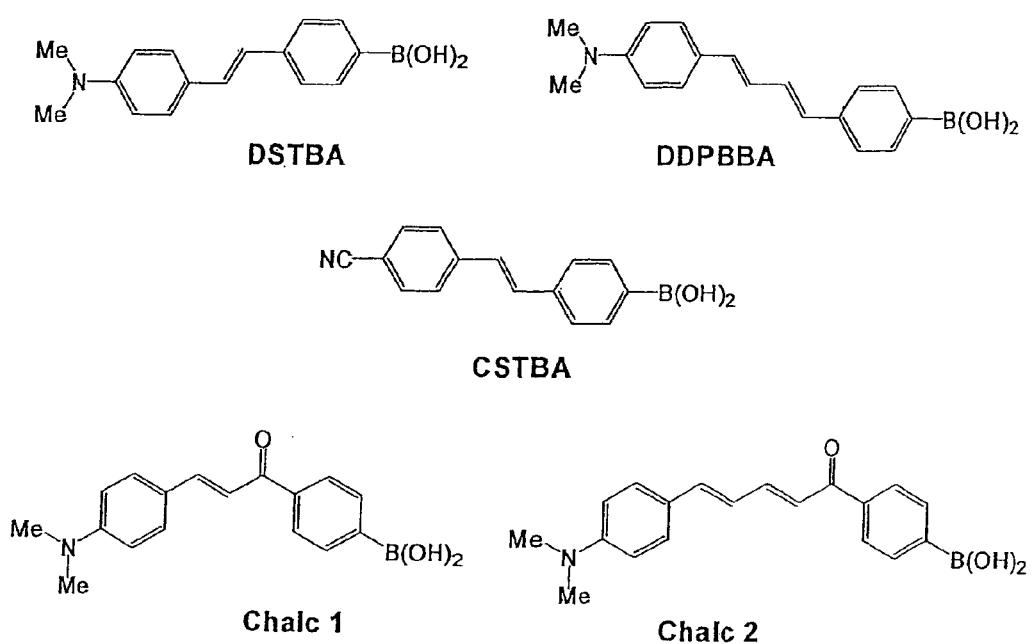
FIG. 31 shows several boronic acid-containing fluorophores including: the stilbenes 4'-dimethylaminostilbene-4-boronic acid (DSTBA) and 4'-cyanostilbene-4-boronic acid (CSTBA); the polyene 1-(p-boronophenyl)-4-(p-dimethylaminophenyl)buta-1,2-diene (DDPBBA); and the chalcones 3-[4'-(dimethylamino)phenyl]-1-(4'-boronophenyl)-prop-2-en-1-one (Chalc 1) and 5-[4'-(dimethylamino)phenyl]-1-(4'-boronophenyl)-pent-2,4-dien-1-one (Chalc 2).

7. Absorption and Emission Studies of Solutions Containing other Boronic Acid Fluorophores (BAFs) in the Absence and Presence of Monosaccharides Stilbene, polyene and chalcone derivatives were tested to determine their suitability as monosaccharide-determining molecular sensing compounds. Referring to FIG. 31, several boronic acid-containing fluorophores (BAFs) including: the stilbenes 4'-dimethylaminostilbene-4-boronic acid (DSTBA) and 4'-cyanostilbene-4-boronic acid (CSTBA); the polyene 1-(p-boronophenyl)-4-(p-dimethylaminophenyl)buta-1,2-diene; and the chalcones 3-[4'-(dimethylamino)phenyl]-1-(4'-boronophenyl)-prop-2-en-1-one (Chalc 1) and 5-[4'-(dimethylamino)phenyl]-1-(4'-boronophenyl)-pent-2,4-dien-1-one (Chalc s) are shown. The preparation of the BAFs was in accordance with previous reports (Dicesare, N., et al., *Tetrahedron Letters*, 43, 2615-2618 (2002); Dicesare, N., et al., *J. Biomed. Optics*, 7(4), 538-545 (2002)).

Each BAF was tested to determine the usefulness of these BAFs with regard to tear glucose sensing in a contact lens. Towards that end, both solution-based and doped contact lens-based measurements, the methods of which are described above, were performed and subsequently compared.

Excited-state charge transfer (CT) mechanisms were exploited to induce spectral changes of the BAFs in the presence of monosaccharides. CT may be applied because the boronic acid group (—B(OH)$_2$— electron withdrawing) and an electron donor group are present on the same fluorophore. In the presence of monosaccharides and appropriate pH values, the boronic acid group is present in its anionic form (represented by B or D in FIG. 1), and as such is no longer an electron withdrawing group. Because the charge transfer nature of the excited state has been perturbed by the presence of monosaccharide and/or hydroxide ions, spectral changes can be observed.

The stilbene DSTBA combines the electron withdrawing boronic acid group with the electron donating dimethylamino group. As such, in the presence of monosaccharides, DSTBA is expected to demonstrate a reduced CT. In contrast, CSTBA, which has two electron withdrawing groups—boronic acid and cyano—is expected to demonstrate an increased CT in the presence of monosaccharides.

Figure 32:
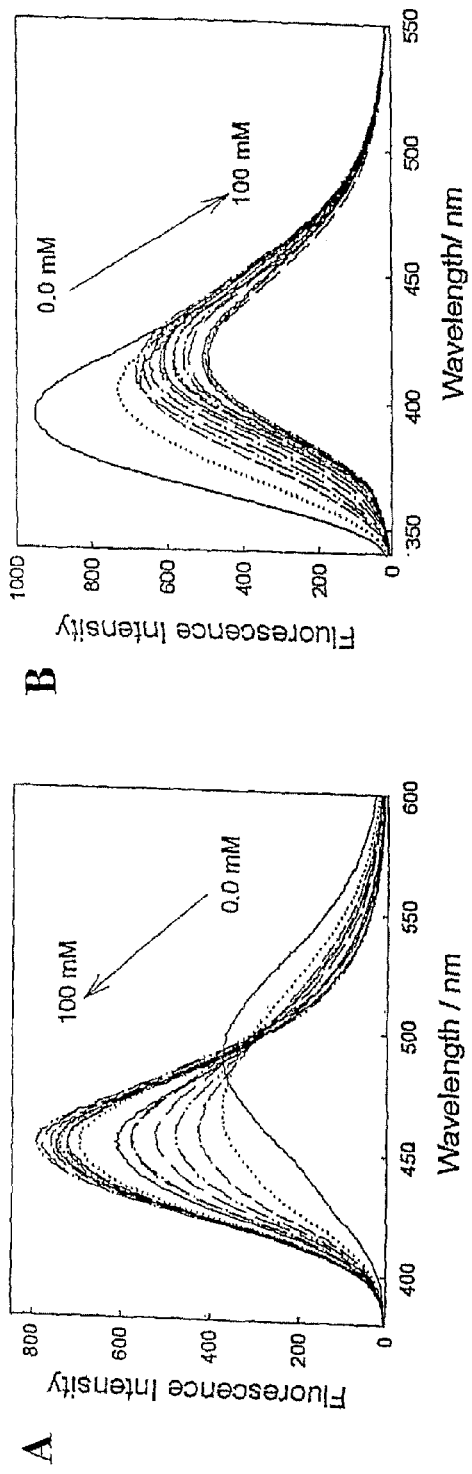
FIG. 32A shows the emission spectra ($\lambda_{ex}$=340 nm) of DSTBA in pH 8.0 buffer/methanol (2:1) with increasing concentrations of fructose.
FIG. 32B shows the emission spectra ($\lambda_{ex}$=320 nm) of CSTBA in pH 8.0 buffer/methanol (2:1) with increasing concentrations of fructose.
FIG. 32C shows the ratiometric response of DSTBA to both fructose and glucose.
FIG. 32D shows the ratiometric response of CSTBA to both fructose and glucose.
Figure 32:
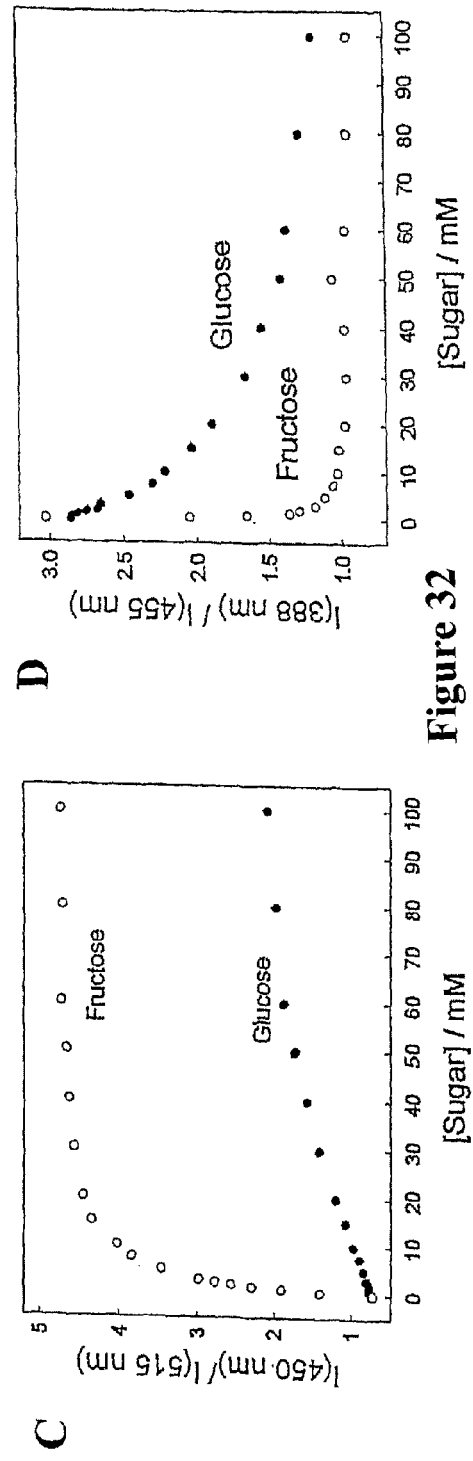

FIG. 32A shows the effect of increasing concentrations of fructose on the emission spectra of DSTBA in pH 8.0 buffer/methanol (2:1). It can be seen that as the concentration of fructose increases, the emission spectra undergo a blue shift of about 30 nm (over a fructose concentration range of 0 mM→100 mM) and an increase in fluorescence intensity. The blue shift and the change in intensity is attributed to the reduction of electron withdrawing capability of the boronic acid moiety with increasing monosaccharide complexation.

Ratiometrically, DSTBA demonstrates significant changes with increasing fructose and glucose concentrations (see FIG. 32C). For example, at 60 mM sugar, fructose shows a 4.5-fold change in intensity, while glucose shows a very respectable 2-fold change in intensity.

In contrast, the stilbene CSTBA, which includes two electron withdrawing groups, demonstrated an emission spectra red shift of about 25 nm with increasing fructose concentration (see FIG. 32B, which shows the effect of increasing concentrations of fructose on the emission spectra of CSTBA in pH 8.0 buffer/methanol (2:1)), and a decrease in emission intensity, which is opposite of that observed with DSTBA. It is speculated that the red shift is due to an excited CT state caused by the ionization of the boronate group with increasing sugar concentrations, said boronate group acting as an electron donor group to the cyano groups electron withdrawing capability.

Ratiometrically, CSTBA demonstrates significant changes with increasing fructose and glucose concentrations (see FIG. 32D), most notably for fructose.

Figure 33:
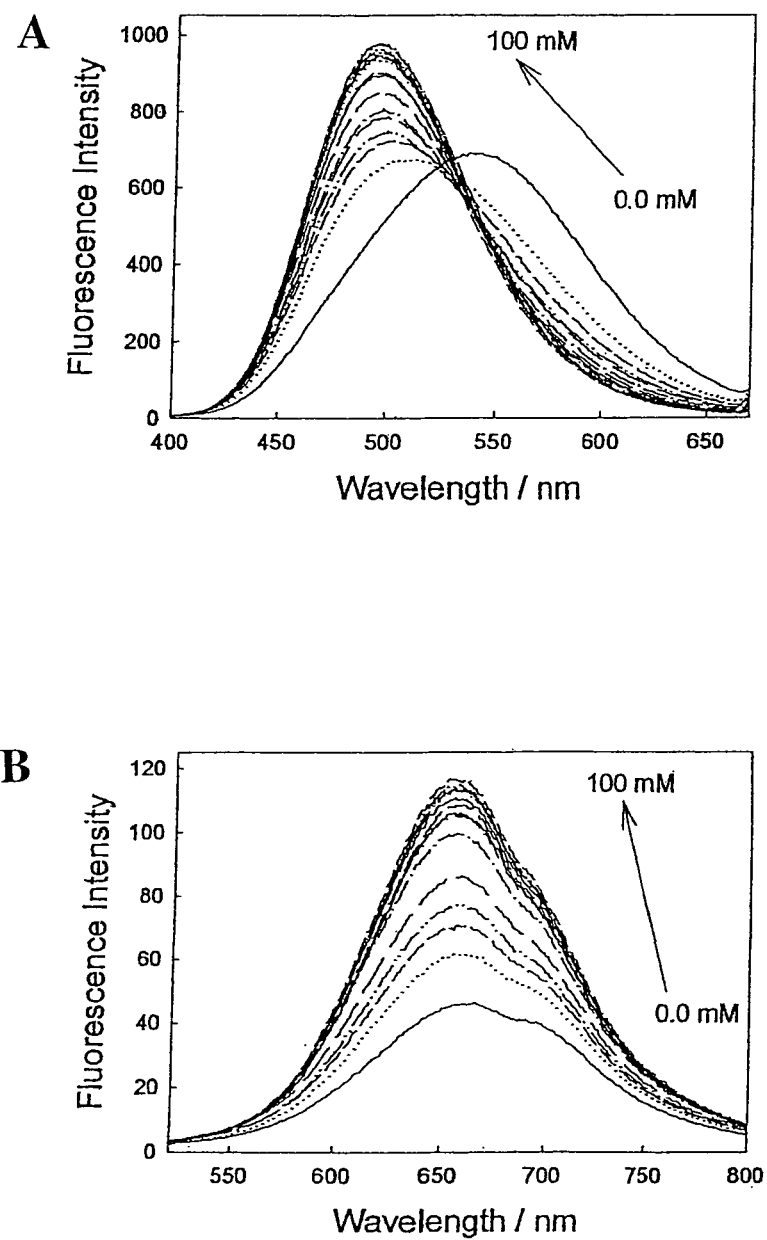
FIG. 33A shows the emission spectra ($\lambda_{ex}$=340 nm) of DDPBBA in pH 8.0 buffer/methanol (2:1) with increasing concentrations of fructose.
FIG. 33B shows the emission spectra ($\lambda_{ex}$=430 nm) of Chalc 2 in pH 8.0 buffer/methanol (2:1) with increasing concentrations of fructose.

FIG. 33A shows the effect of increasing concentrations of fructose on the emission spectra of the polyene DDPBBA in pH 8.0 buffer/methanol (2:1). Like DSTBA, which also has an electron donating group (NMe$_2$), a blue shift was observed with increasing concentrations of sugar as well an increase in emission intensity.

Compounds that emit longer wavelength emission are particularly attractive because (a) it reduces the detection of any lens or eye autofluorescence as well as scatter, and (b) it allows one to use cheaper wavelength excitation sources, such as lasers and LEDs. Towards that end, the feasibility of using Chalc 1 and Chalc 2 fluorophores, was investigated using compounds that were previously synthesized (Dicesare, N., et al., *Tetrahedron Letters*, 43, 2615-2618 (2002); Dicesare, N., et al., *J. Biomed. Optics*, 7(4), 538-545 (2002)). With chalcone derivatives the charge transfer occurs between the dimethylamino group (electron donating) and the carbonyl group (electron withdrawing). However, any change to the electronic properties of the boron group leads to a change in the electron density of the benzophenone moiety and as such, the charge transfer properties of the excited state of the fluorophore. Referring to FIG. 33B, which shows the effect of increasing concentrations of fructose on the emission spectra ($\lambda_{em}$=665 nm) of Chalc 2 in pH 8.0 buffer/methanol (2:1), it can be seen that the chalcone derivative undergoes a blue shift and an increase in emission intensity with increasing fructose concentrations. Chalc 1 showed a corresponding blue shift and increase in emission intensity with the emission centered around 580 nm.

8. Absorption and Emission Studies of Contact Lenses Containing other Boronic Acid Fluorophores (BAFs) in the Absence and Presence of Monosaccharides As introduced above, prior to the addition of the sugars to the 1.5 cm$^3$ lens holder, the lenses were doped with the appropriate fluorophore, washed and allowed to leach for approximately 1 hour. Fluorescence emissions were taken about 15 min after the addition of each aliquot of sugar to the lens holder to allow the lens to reach equilibrium.

Figure 34:
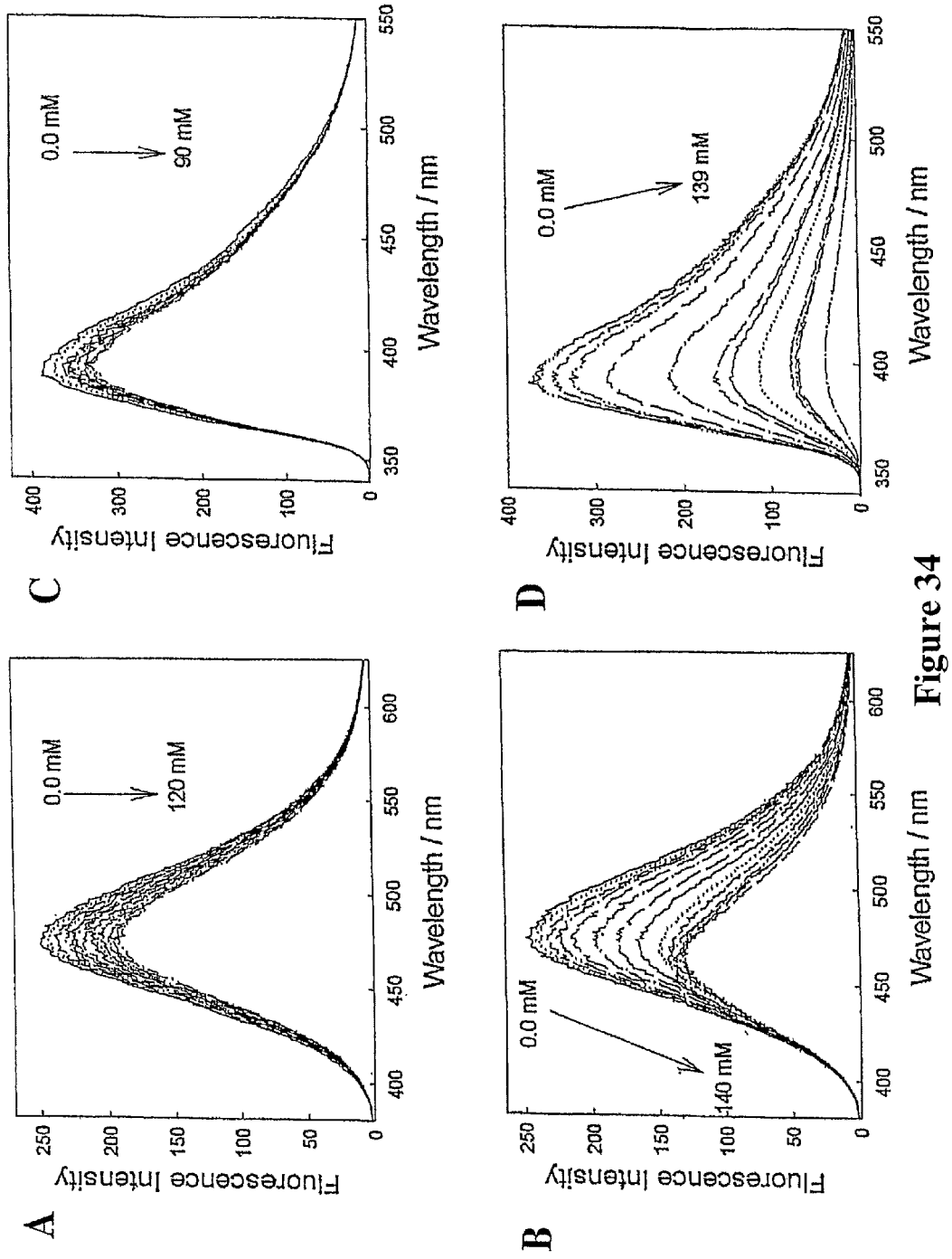
FIG. 34A shows the emission spectra ($\lambda_{ex}$=340 nm) of a DSTBA-doped contact lens in pH 8.0 buffer/methanol (2:1) with increasing concentrations of glucose.
FIG. 34B shows the emission spectra ($\lambda_{ex}$=340 nm) of a DSTBA-doped contact lens in pH 8.0 buffer/methanol (2:1) with increasing concentrations of fructose.
FIG. 34C shows the emission spectra ($\lambda_{ex}$=340 nm) of a CSTBA-doped contact lens in pH 8.0 buffer/methanol (2:1) with increasing concentrations of glucose.
FIG. 34D shows the emission spectra ($\lambda_{ex}$=340 nm) of a CSTBA-doped contact lens in pH 8.0 buffer/methanol (2:1) with increasing concentrations of fructose.

FIGS. 34A and 34B show the emission spectra of a DSTBA-doped contact lens in pH 8.0 buffer/methanol (2:1) with increasing concentrations of glucose and fructose, respectively. As expected the intensity change in the presence of fructose was greater. However, comparing the emission response in the presence of fructose of DSTBA in the doped contact lens (see FIG. 34B) with those of the solution-based studies discussed above (see FIG. 32A), it can be seen that the responses were converse to one another, wherein the intensity of the emission increased with increasing fructose concentration in the solution-based experiment but decreased in the corresponding doped contact lens experiment.

Similarly, FIGS. 34C and 34D show the emission spectra of a CSTBA-doped contact lens in pH 8.0 buffer/methanol (2:1) with increasing concentrations of glucose and fructose, respectively. Comparing the fructose experiment performed in solution (see FIG. 32B) with those of the doped contact lens (see FIG. 34D), it can be seen that the intensity similarly decreased with increasing fructose concentration. However, the significant red shift observed in the solution-based studies was not observed in the doped contact lens studies, suggesting that the electron-donating capability of the anionic boronate groups decreased.

Figure 35:
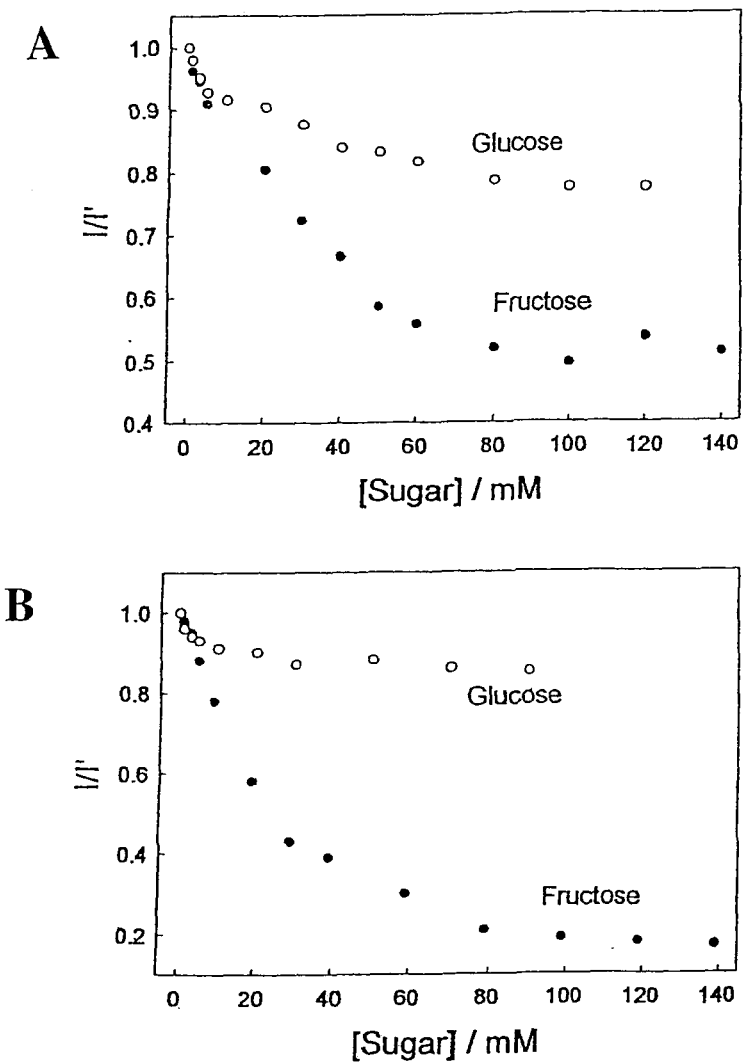
FIG. 35 shows the intensity ratio of a (A) DSTBA-doped contact lens and (B) CSTBA-doped contact lens in pH 8.0 buffer/methanol (2:1) in the absence, I', and presence, I, of sugar.

FIG. 35 shows the simple intensity ratio of a (A) DSTBA-doped contact lens and (B) CSTBA-doped contact lens in pH 8.0 buffer/methanol (2:1) in the absence, I', and presence, I, of sugar. Interestingly, there is a more significant response to fructose in the CSTBA-doped contact lens (see FIG. 35B) than in the DSTBA-doped contact lens (see FIG. 35A). Regarding glucose, at concentrations of about 10 mM, there is a 10% fluorescence change in the DSTBA-doped contact lens, which is promising.

Figure 36:
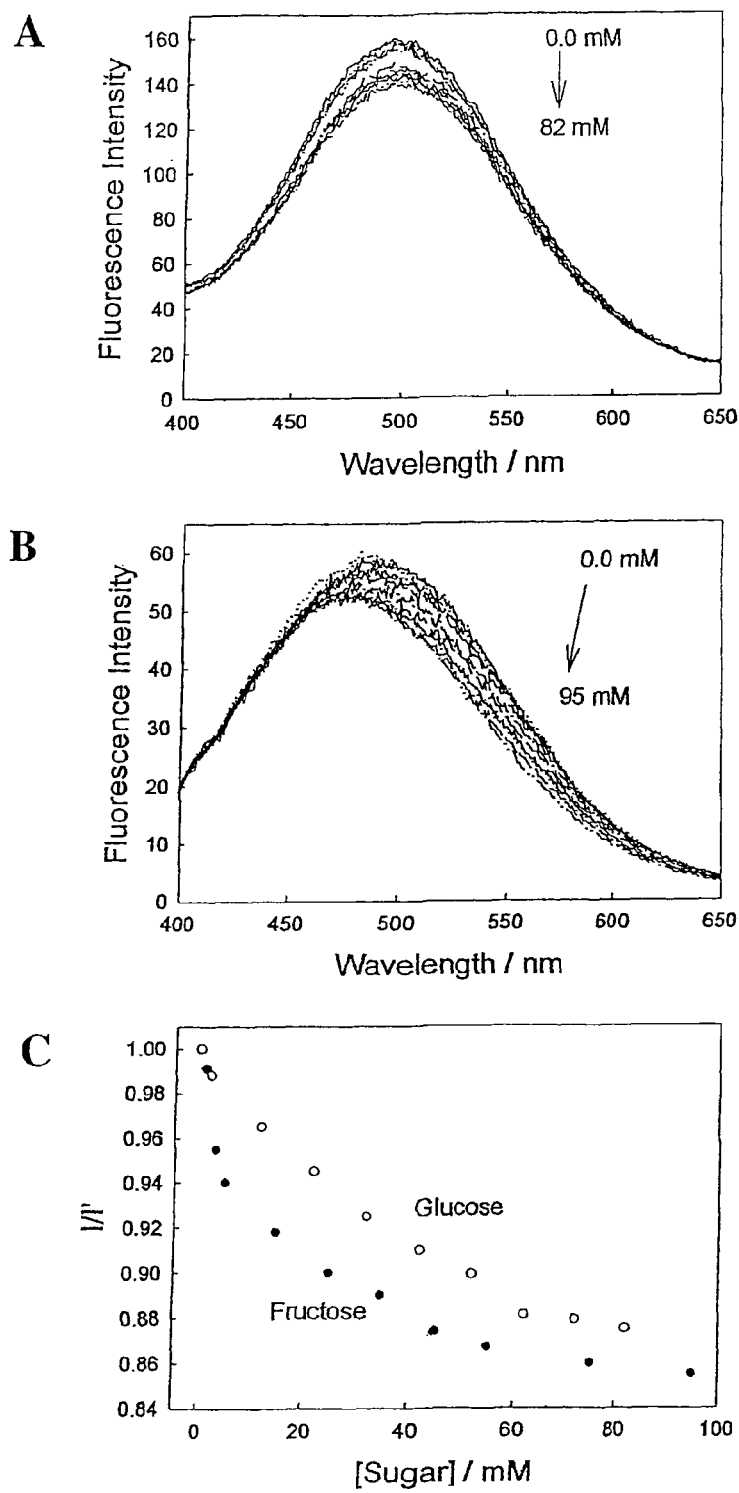
FIG. 36A shows the emission spectra ($\lambda_{ex}$=340 nm) of a DDPBBA-doped contact lens in pH 8.0 buffer/methanol (2:1) with increasing concentrations of glucose.
FIG. 36B shows the emission spectra ($\lambda_{ex}$=340 nm) of a DDPBBA-doped contact lens in pH 8.0 buffer/methanol (2:1) with increasing concentrations of fructose.
FIG. 36C shows the intensity ratio of a DDPBBA-doped contact lens in pH 8.0 buffer/methanol (2:1) in the absence, I', and presence, I, of sugar.

Comparing the emission spectra of DDPBBA-doped contact lenses in the presence of fructose (see FIG. 36B) with those observed in the solution-based experiments (see FIG. 33A), it can be seen that though the blue shift similarly occurred in both with increasing fructose concentrations, the change in fluorescence intensity with increasing fructose concentrations was opposite, decreasing in the case of the DDPBBA-doped contact lens. It is noted that although this was similarly observed with respect of DSTBA, DSTBA displayed a more significant response to sugar (compare FIGS. 34B and 36B).

Figure 37:
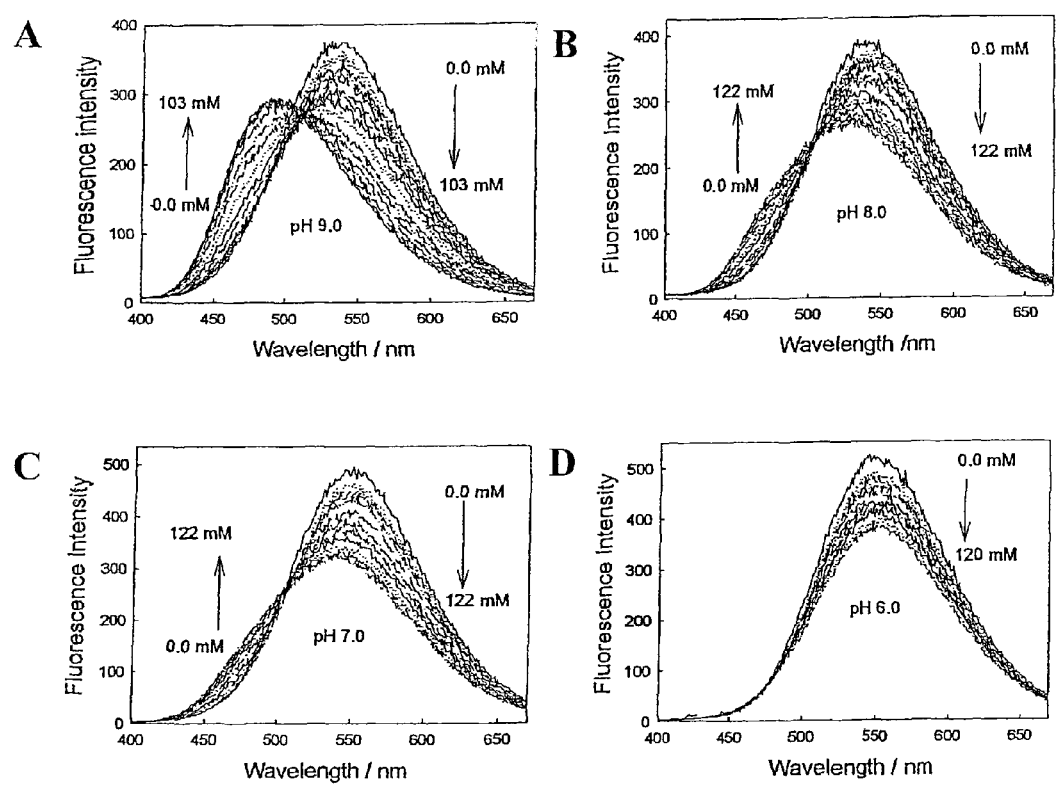
FIG. 37 shows the emission spectra of DDPBBA-doped contact lenses in pH media (buffer/methanol (2:1)) at (A) pH 9.0, (B) pH 8.0, (C) pH 7.0, and (D) pH 6.0.

In light of the fact that the response to the sugars in the doped lenses was opposite to that observed in solution, a series of emission experiments were performed using a DDPBBA solution in different pH media in the presence of increasing glucose concentrations. As the solution pH increases, the emission spectra of DDPBBA display a blue shift, which can be attributed to a change in acidity from the uncomplexed form at low pH values (represented by A in FIG. 1) to the complexed form at higher pH values (represented by B in FIG. 1). Interestingly, the spectral response of the DDPBBA-doped contact lens in the presence of glucose (see FIG. 36A) was similar to that observed in the pH 6.0 media (see FIG. 37D). It is speculated that at the lower pH, such as that of the contact lens, the formation of the boronic acid diester (represented by C in FIG. 1) does not result in a full perturbation of the DDPBBA fluorophore, hence DDPBBA is not suitable as a wavelength ratiometric probe in the contact lens. It is noted that the DDPBBA fluorophore is ideal for solution sugar sensing in the pH 6.5-8.5 range, which is ideal to determine blood glucose levels.

Notably, BAF's such as DDPBBA are not fully perturbated at pH 6.0, and as such DDPBBA molecular sensing compounds are not able to sense glucose levels in tears as effectively as the novel quaternary nitrogen compounds discussed herein which was the impetus for the discovery of the novel quaternary nitrogen containing boronic acid compounds, including, but not limited to, BMQBA and BMOQBA, which display lower $pK_a$ values and as such, are more sensitive to tear glucose levels.

Figure 38:
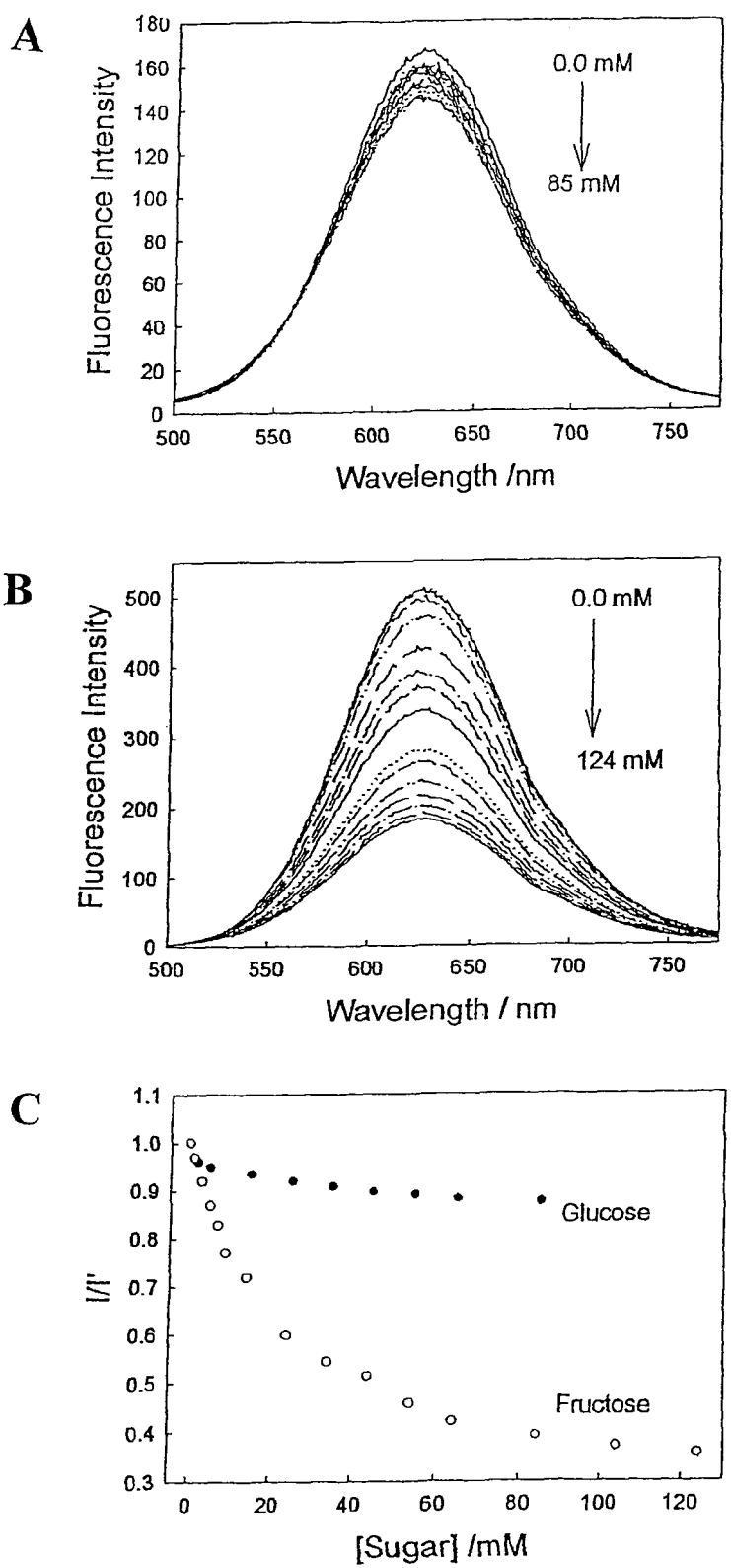
FIG. 38A shows the emission spectra ($\lambda_{ex}$=460 nm) of a Chalc 2-doped contact lens in pH 8.0 buffer/methanol (2:1) with increasing concentrations of glucose.
FIG. 38B shows the emission spectra ($\lambda_{ex}$=460 nm) of a Chalc 2-doped contact lens in pH 8.0 buffer/methanol (2:1) with increasing concentrations of fructose.
FIG. 38C shows the intensity ratio of a Chalc 2-doped contact lens in pH 8.0 buffer/methanol (2:1) in the absence, I', and presence, I, of sugar.

FIGS. 38A and 38B show the emission spectra ($\lambda_{em}$=560 nm) of a Chalc 2-doped contact lens in pH 8.0 buffer/methanol (2:1) with increasing concentrations of (A) glucose and (B) fructose, respectively. It is noted that the Chalc 1-doped contact lens displayed similar results to the Chalc 2-doped contact lens, with the emission centered at λ=630 nm. Like DDPBBA and DSTBA, the emission intensity of the doped contact lens and the solution-based studies for both Chalc 1 and Chalc 2 were opposite, decreasing in the case of the former. A simple intensity ratio of a Chalc 2-doped contact lens in pH 8.0 buffer/methanol (2:1) in the absence, I', and presence, I, of sugar is shown in FIG. 38C. Interestingly, the solution response for Chalc 2 in the presence of 100 mM fructose at pH 8.0 produces a 3-fold increase in fluorescence emission (see FIG. 33B), as compared to the approximately 2.6-fold reduction for the same fructose concentration in the contact lens.

9. Compounds (L), (M) and (N) as Glucose-Sensing Molecules for Covalent Binding to Contact Lenses Compounds (L), (M), (N) and (O), previously described herein, were synthesized. Compound (O) was utilized as a control compound, devoid of boronic acid functionality and therefore unable to bind and sense glucose, to assess the di-boronic acid compounds (L) and (M) and the mono-boronic acid compound (N).

The di-boronic acid compounds (L) and (M) were utilized with the intention of achieving glucose specificity in contact lenses, with molecules in which the spacing distance between the boronic acid groups was determined to be specific for interaction with glucose. Molecules having glucose specificity in the presence of other sugars or carbohydrates are particularly preferred compounds, as being free of interference for such glucose sensing.

FIGS. 39-42 show the response of the di-boronic acid probes, compound (L), denoted p-DBQBA, and compound (M), denoted o-DBQBA, towards glucose. The probes were immobilized in a contact lens by covalent bonding through the reactive alkenyl functionality of such compounds.

Figure 39:
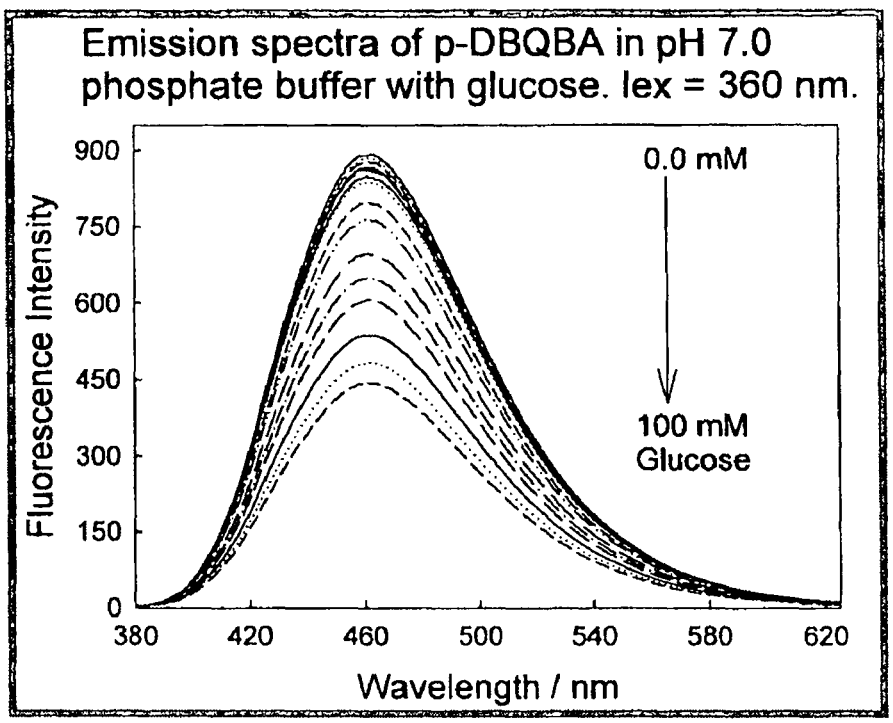
FIG. 39 shows the emission spectra (($\lambda_{ex}$=360 nm) of compound (L) in pH 7.0 buffer with glucose.
Figure 40:
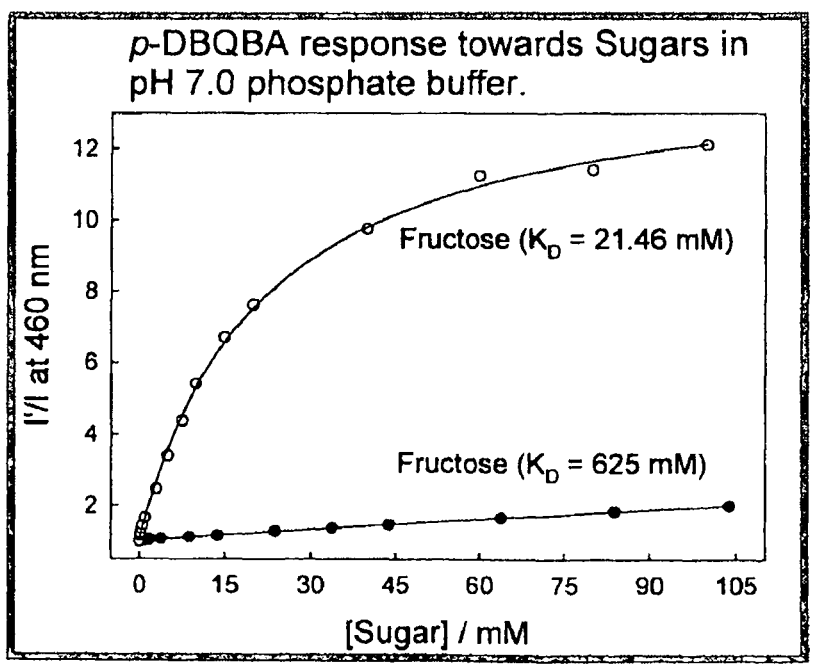
FIG. 40 shows the intensity ratio for response of compound (L) towards sugars in pH 7.0 phosphate buffer.

FIG. 39 shows the emission spectra ($\lambda_{ex}$=360 nm) of compound (L) in pH 7.0 buffer with glucose. FIG. 40 shows the intensity ratio for response of compound (L) towards sugars in pH 7.0 phosphate buffer.

Figure 41:
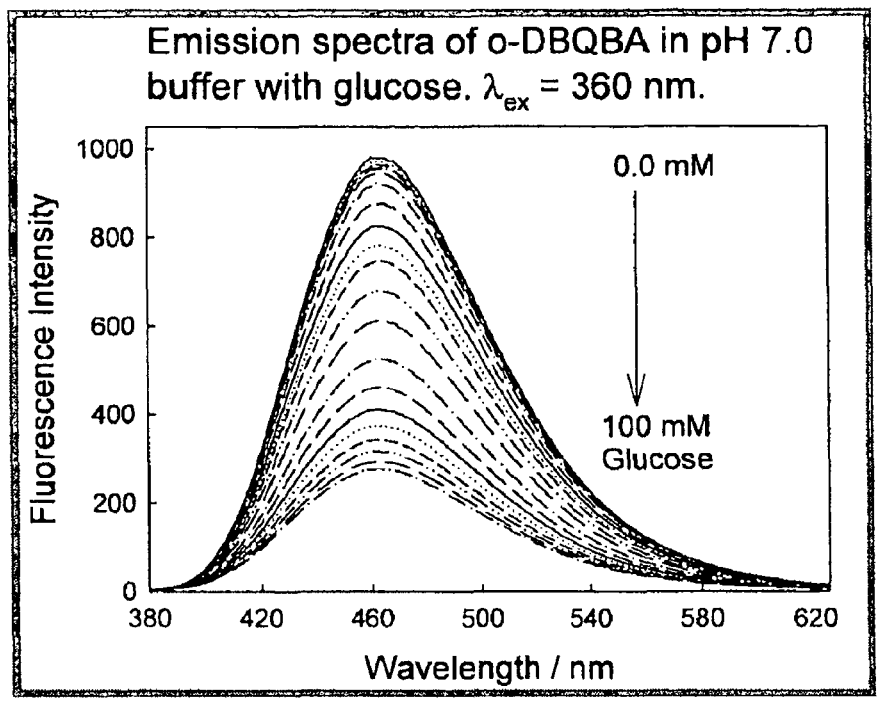
FIG. 41 shows the emission spectra (($\lambda_{ex}$=360 nm) of compound (M) in pH 7.0 buffer with glucose.
Figure 42:
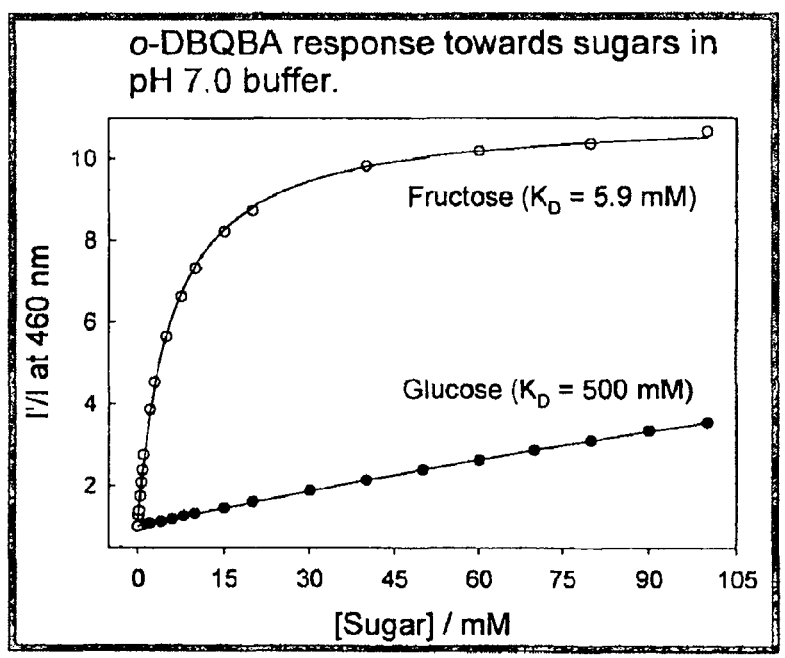
FIG. 42 shows the intensity ratio for response of compound (M) towards sugars in pH 7.0 buffer.

FIG. 41 shows the emission spectra ($\lambda_{ex}$=360 nm) of compound (M) in pH 7.0 buffer with glucose. FIG. 42 shows the intensity ratio for response of compound (M) towards sugars in pH 7.0 buffer.

Interestingly, the glucose binding constants of these probes was about 2-3 times lower as compared to o-N-(boronobenzyl)-6-methoxyquinolinium bromide, which had a Kd of about 180 mM. This was attributed to steric hindrance effects and the lower diffusion rate of glucose in the lens as compared to free solution, as well as the matrix effect in the lens, in which some probe molecules are inaccessible to glucose after covalent attachment.

Figure 43:
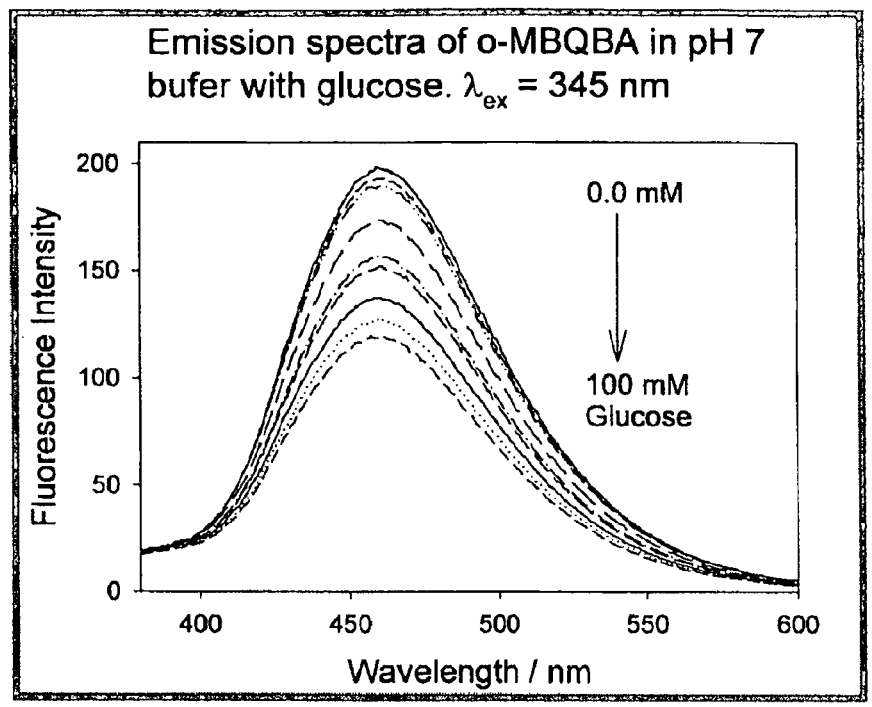
FIG. 43 shows the emission spectra (($\lambda_{ex}$=345 nm) of compound (N) in pH 7.0 buffer with glucose.
Figure 44:
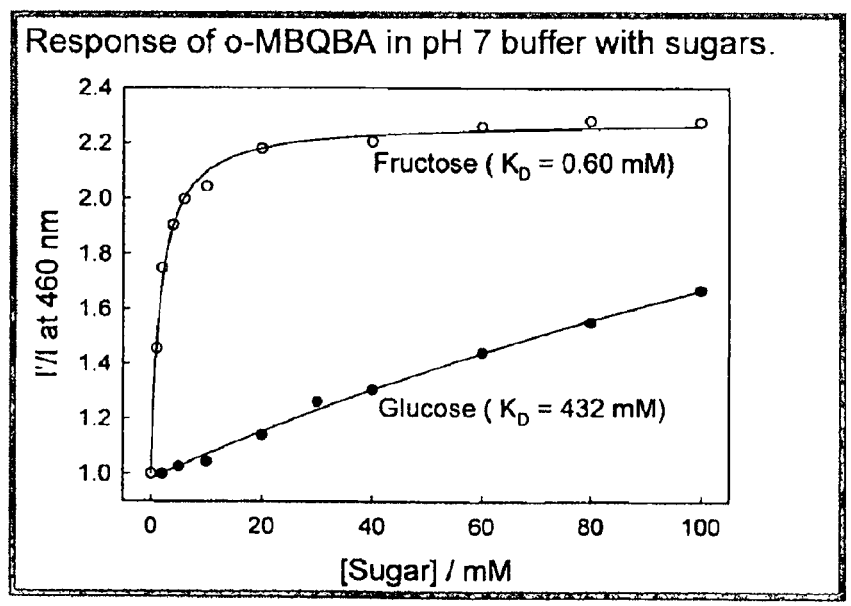
FIG. 44 shows the intensity ratio for response of compound (L) towards sugars in pH 7.0 buffer.

To further assess this response behavior, compound (N), denoted o-MBQBA, having only a single boronic acid group, was evaluated, yielding the results shown in FIGS. 43 and 44.

FIG. 43 shows the emission spectra (($\lambda_{ex}$=345 nm) of compound (N) in pH 7.0 buffer with glucose. FIG. 44 shows the intensity ratio for response of compound (N) towards sugars in pH 7.0 buffer.

When the glucose response is compared for both ortho compounds (M) and (N) when bound into the contact lens, the mono-boronic acid probe (compound (N)) exhibited slightly better response, suggesting that binding of glucose to both boronic acid groups in the di-boronic acid species did not occur with the same probability and that after binding, steric hindrance effects impeded further glucose binding.

All of the boronic acid-functionalized compounds (L)-(N) thus demonstrated glucose sensing capability for physiological tear levels in the mildly acid and modestly polar medium of the contact lens.

While the invention has been described herein with reference to various specific embodiments, it will be appreciated that the invention is not thus limited, and extends to and encompasses various other modifications and embodiments, as will be appreciated by those ordinarily skilled in the art.

That which is claimed is:

1. A fluorescence compound selected from the group consisting of:

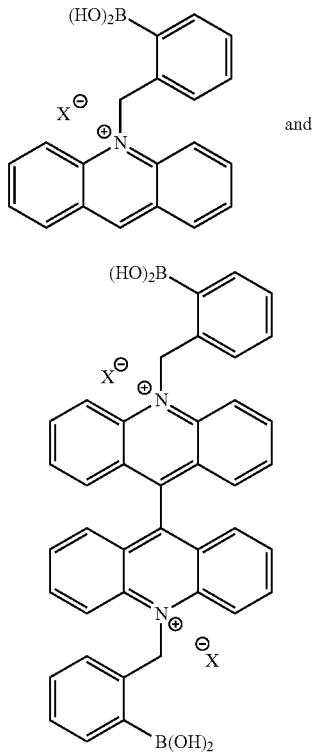

wherein X is chloride, bromide or iodide.

2. The compound of claim 1, wherein the fluorescence intensity of the compound changes in the presence of analytes.

3. The compound of claim 2, wherein the analyte comprise a species selected from the group consisting of glucose, fructose, chloride and iodide.

4. The compound of claim 1, wherein the fluorescence intensity of the compound decreases in the presence of glucose.

5. A method of measuring the concentration of an analyte in a physiological fluid, said method comprising:
(a) contacting a fluorescence compound selected from the group consisting of:

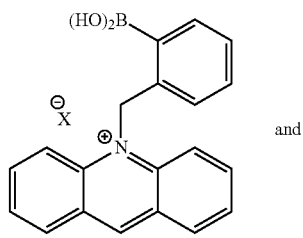

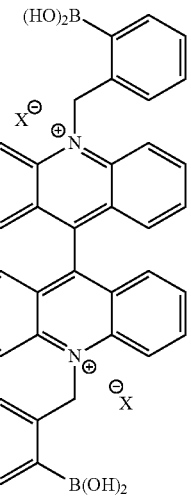

wherein X is chloride, bromide or iodide,
with the physiological fluid for sufficient time to at least partially interact or react with the analyte; and
(b) measuring the optical signal of the fluorescence compound in the presence of the analyte for a sufficient time to determine the concentration of analyte in the physiological fluid.

6. The method of claim 5, wherein the physiological fluid is blood, tears, interstitial fluid or aqueous humor.

7. An assay kit for measuring the concentration of an analyte in a physiological fluid comprising a container containing a fluorescence compound selected from the group consisting of:

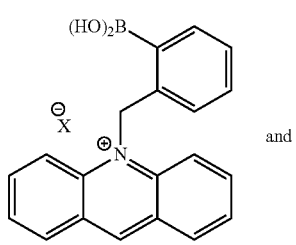

-continued

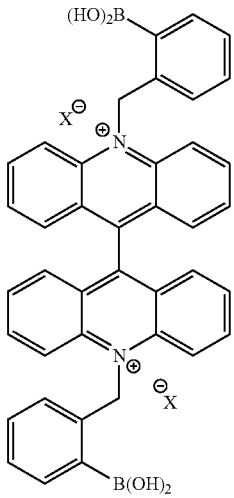
(E)

wherein X is chloride, bromide or iodide.

8. The kit of claim 7, wherein the physiological fluid is blood.

9. An ophthalmic sensor comprising:
a polymer matrix comprising a fluorescence compound contracting at least the outer surface of the polymer matrix, wherein the fluorescence compound interacts or reacts with an analyte to provide an optical signal which is indicative of the analyte concentration in an ocular fluid and wherein the fluorescence compound is at least one member selected from the group consisting of:

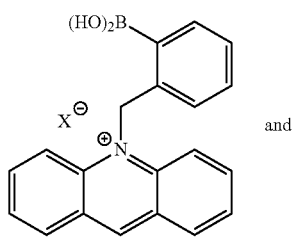 and
(C)

-continued

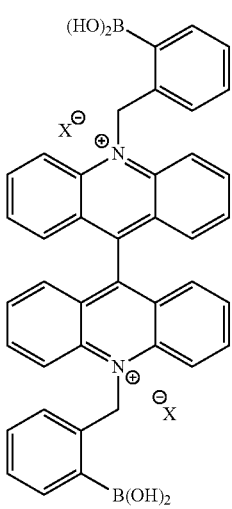
(E)

wherein X is chloride, bromide or iodide.

10. The ophthalmic sensor of claim 9, wherein the ophthalmic device is a contact lens and the fluorescence compound is coated on the surface of the contact lens of impregnated into the polymeric matrix.

11. The ophthalmic sensor of claim 9, wherein the analyte comprises a species selected from the group consisting of glucose, fructose, chloride, and iodide.

12. The ophthalmic sensor of claim 9, wherein the substrate is implantable.

13. The ophtahlmic sensor of claim 9, wherein the optical signal is fluorescence and is measured based on the intensity, lifetime, anisotropy or ratiometric fluorescence platforms.

* * * * *